(12) United States Patent
Hashizume et al.

(10) Patent No.: US 7,279,486 B2
(45) Date of Patent: Oct. 9, 2007

(54) ALPHA ARYL OR HETEROARYL METHYL BETA PIPERIDINO PROPANOIC ACID COMPOUNDS AS ORL1-RECEPTOR ANTAGONISTS

(75) Inventors: Yoshinobu Hashizume, Aichi-Ken (JP); Masako Hirota, Aichi-Ken (JP); Sachiko Mihara, Aichi-Ken (JP); Hiroshi Nakamura, Aichi-Ken (JP); Hiroki Koike, Aichi-Ken (JP); Yukari Matsumoto, Aichi-Ken (JP)

(73) Assignee: Pfizer Inc., New York, NY (US)

( * ) Notice: Subject to any disclaimer, the term of this patent is extended or adjusted under 35 U.S.C. 154(b) by 393 days.

(21) Appl. No.: 11/092,503

(22) Filed: Mar. 29, 2005

(65) Prior Publication Data
US 2005/0277659 A1  Dec. 15, 2005

Related U.S. Application Data

(60) Provisional application No. 60/557,598, filed on Mar. 29, 2004.

(51) Int. Cl.
*A61K 31/438* (2006.01)
*C07D 491/107* (2006.01)

(52) U.S. Cl. .................. 514/278; 546/17; 546/14
(58) Field of Classification Search ........... 514/278; 546/17, 14
See application file for complete search history.

(56) References Cited

U.S. PATENT DOCUMENTS

| 5,206,240 | A | 4/1993 | Baldwin et al. | |
| 6,869,960 | B2 * | 3/2005 | Ito et al. ................ | 514/278 |

FOREIGN PATENT DOCUMENTS

| EP | 0431943 A2 | 6/1991 |
| WO | WO94/29309 | 12/1994 |
| WO | WO98/25605 | 6/1998 |
| WO | WO02/26714 A1 | 4/2002 |
| WO | WO02/085354 A1 | 11/2002 |
| WO | WO03/000677 A1 | 1/2003 |
| WO | WO03/064425 A1 | 8/2003 |
| WO | WO2004/002987 A1 | 1/2004 |
| WO | WO2004/041279 A1 | 5/2004 |
| WO | WO2004/058727 A1 | 7/2004 |

\* cited by examiner

*Primary Examiner*—Charanjit S. Aulakh
(74) *Attorney, Agent, or Firm*—Gregg C. Benson; Frank W. Forman

(57) ABSTRACT

This invention provides the compounds of formula (I):

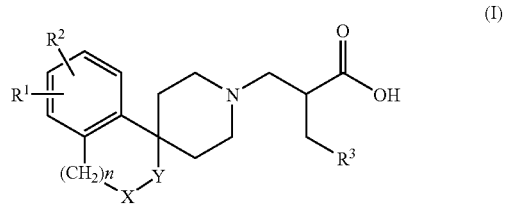

or a pharmaceutically acceptable ester of such compound, or a pharmaceutically acceptable salt thereof, wherein $R^1$ and $R^2$ independently represent a hydrogen atom or the like; $R^3$ represents an aryl group having from 6 to 10 ring atoms or the like; X represents an oxygen atom, or the like; Y represents an oxygen atom or the like; and n represents an integer 0, 1 or 2.

These compounds have ORL1-receptor antagonist activity; and therefore, are useful to treat diseases or conditions such as pain, various CNS diseases etc.

9 Claims, No Drawings

ALPHA ARYL OR HETEROARYL METHYL BETA PIPERIDINO PROPANOIC ACID COMPOUNDS AS ORL1-RECEPTOR ANTAGONISTS

This application claims benefit of provisional application 60/557,598 filed on Mar. 29, 2004.

TECHNICAL FIELD

This invention relates to alpha aryl or heteroaryl methyl beta piperidino propanoic acid compounds and pharmaceutically acceptable esters or pharmaceutically acceptable salts and solvates thereof, and a medical use thereof. Also, this invention relates to a pharmaceutical composition comprising said compound, or its pharmaceutically acceptable ester or pharmaceutically acceptable salt. The compounds of this invention have binding affinity for the ORL-1 receptor. In particular, compounds of this invention have antagonist activity for said receptor. The compounds of this invention are useful in treating or preventing disorders or medical conditions selected from pain, a CNS disorder and the like, which are mediated by overactivation of said receptor.

BACKGROUND ART

Three types of opioid receptors, μ (mu), δ (delta) and κ (kappa) have been identified. These receptors may be indicated with combinations of OP (abbreviation for Opioid Peptides) and numeric subscripts as suggested by the International Union of Pharmacology (IUPHAR). Namely, $OP_1$, $OP_2$ and $OP_3$ respectively correspond to δ-, κ- and μ-receptors. It has been found out that they belong to G-protein-coupled receptors and are distributed in the central nervous system (CNS), peripheries and organs in a mammal. As ligands for the receptors, endogenous and synthetic opioids are known. It is believed that an endogenous opioid peptide produces its effects through an interaction with the major classes of opioid receptors. For example, endorphins have been purified as endogenous opioid peptides and bind to both δ- and μ-receptors. Morphine is a well-known non-peptide opioid analgesic and has binding affinity mainly for the μ-receptor. Opiates have been widely used as pharmacological agents, but drugs such as morphine and heroin induce some side effects such as drug addiction and euphoria.

Meunier et al. reported isolation of a seventeen-amino-acid-long peptide from rat brain as an endogenous ligand for an orphan opioid receptor (Nature, Vol. 337, pp. 532-535, Oct. 12, 1995), and said receptor is now known as "opioid receptor-like 1 (abbreviated as ORL-1 receptor)". In the same report, the endogenous opioid ligand has been introduced as agonist for the ORL-1 receptor and named as "nociceptine (abbreviated as NC)". Also, the same ligand was named as "orphanin FQ (abbreviated as OFQ or oFQ)" by Reinscheid et al. (Science, Vol. 270, pp. 792-794, 1995). This receptor may be indicated as $OP_4$ in line with a recommendation by IUPHAR in 1998 (British Journal of Pharmacology, Vol. 129, pp. 1261-1283, 2000).

International Patent Application Number (WO) 9429309 discloses a variety of spiro-substituted azacycle compounds, which are Neurokinin antagonists useful in the treatment of pain.

Also, International Patent Application Number (WO) 9825605 discloses a variety of spiro-substituted azacycle compounds, which are Chemokine receptor activity modulator antagonists.

Further, International Patent Application Number (WO) 0226714 discloses a variety of spiropiperidino compounds which show a binding affinity to a Nociceptin receptor.

Yet further, International Patent Application Number (WO) 03064425 discloses a variety of spiropiperidino compounds, which are ORL1 antagonists, for example, compound (i) below:

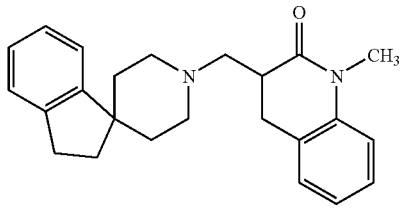

(i)

Compound (i) shows a potent activity in the dofetilide binding assay.

There is a need to provide new ORL1 antagonists that are good drug candidates. In particular, preferred compounds should bind potently to the ORL1 receptor and show functional activity as antagonists whilst showing little affinity for other receptors. They should be well absorbed from the gastrointestinal tract, be metabolically stable and possess favorable pharmacokinetic properties and less drug-drug interaction. They should be non-toxic and demonstrate few side-effects. Furthermore, the ideal drug candidate will exist in a physical form that is stable, non-hygroscopic and easily formulated.

In particular, it would be desirable to provide an ORL1 antagonist with reduced inhibitory activity at HERG potassium channel.

BRIEF DISCLOSURE OF THE INVENTION

It has now surprisingly been found that alpha aryl or heteroaryl methyl beta piperidino propanamide compounds of the present invention are ORL1 antagonists with analgesic activity, particularly when given by systemic administration. Reduced inhibitory activity on the HERG channel has also been observed for selected compounds. Inhibitory activity on the HERG channel was estimated from affinity for HERG type potassium channel by measuring [$^3$H] dofetilide binding, which can predict inhibitory activity on the HERG channel (Eur. J. Pharmacol., 430, pp147-148, 2001). Selected compounds with low [$^3$H] dofetilide binding activity were evaluated in the $I_{HERG}$ assay to check activity at HERG channel. The selected compounds of the present invention showed a reduced QT prolongation.

The present invention provides a compound of the following formula (I):

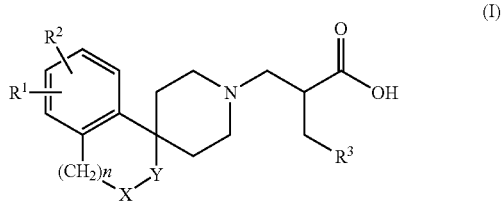

(I)

or a pharmaceutically acceptable ester of such a compound, or a pharmaceutically acceptable salt thereof, wherein $R^1$ and $R^2$ independently represent a hydrogen atom, a halogen atom or an alkyl group having from 1 to 3 carbon atoms;

$R^3$ represents a phenyl group or a heteroaryl group and said heteroaryl group is a 5 or 6 membered hetero aromatic group having either from 1 to 4 ring nitrogen heteroatoms or 1 or 2 nitrogen ring heteroatoms and 1 oxygen or 1 sulfur ring heteroatom;

said phenyl group and heteroaryl group are optionally substituted by 1 to 3 groups selected from a halogen atom, a hydroxy group, an alkyl group having from 1 to 3 carbon atoms, an alkoxy group having from 1 to 3 carbon atoms, an alkoxyalkyl group having a total of from 2 to 6 carbon atoms, a hydroxyalkyl group having from 1 to 3 carbon atoms, an amino group, a mono-or di-alkylamino group each alkyl part having from 1 to 3 carbon atoms, an aminocarbonyl group, a mono- or di-alkylaminocarbonyl group having from 1 to 3 carbon atoms in each alkyl group, an alkanoylamino group having from 2 to 3 carbon atoms and an alkylsulfonylamino group having from 1 to 3 carbon atoms;

—X—Y— represents a group of the formula —N(R$^4$)C(=O)—, —C(=O)N(R$^4$)—, —N(R$^4$)CH$_2$—, —CH$_2$N(R$^4$)—, —N(R$^4$)SO$_2$—, —SO$_2$N(R$^4$)—, —CH$_2$CH$_2$—, —CH=CH—, —CH(CH$_2$OH)CH$_2$—, —CH$_2$CH(CH$_2$OH)—, —CH$_2$CH(OH)—, —CH(OH)CH$_2$—, —C(R$^4$)(R$^5$)—O— or —O—C(R$^4$)(R$^5$)—;

R$^4$ represents a hydrogen atom or an alkyl group having from 1 to 3 carbon atoms; R$^5$ represents a hydrogen atom, an alkyl group having from 1 to 3 carbon atoms or a hydroxyalkyl group having from 1 to 3 carbon atoms; and n represents an integer 0, 1 or 2.

The compounds of the present invention are antagonists of the ORL1 receptor, and have a number of therapeutic applications, particularly in the treatment of pain, sleep disorders, eating disorders including anorexia and bulimia; anxiety and stress conditions; immune system diseases; locomotor disorder; memory loss, cognitive disorders and dementia including senile dementia, Alzheimer's disease, Parkinson's disease or other neurodegenerative pathologies; epilepsy or convulsion and symptoms associated therewith; a central nervous system disorder related to glutamate release action, anti-epileptic action, disruption of spatial memory, serotonin release, anxiolytic action, mesolimbic dopaminergic transmission, rewarding propaerties of drug of abuse, modulation of striatal and glutamate effects on locomotor activity; cardiovascular disorders including hypotension, bradycardia and stroke; renal disorders including water excretion, sodium ion excretion and syndrome of inappropriate secretion of antidiuretic hormone (SIADH); gastrointestinal disorders; airway disorders including adult respiratory distress syndrome (ARDS); autonomic disorders including suppression of micturition reflex; metabolic disorders including obesity; cirrhosis with ascites; sexual dysfunctions; altered pulmonary function including obstructive pulmonary disease, and tolerance to or dependency on a narcotic analgesic or the like.

The compounds of the present invention are useful for the general treatment of pain. Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57: 1-164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765-1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13-44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. back pain, cancer pain have both nociceptive and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13-44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertebral discs or abnormalities of the lumber facet joints, sacroiliac joints, paraspinal muscles or the posterior longitudinal ligament.

Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959-1964). The symptoms of neuropathic pain are difficult to treat, as they are often heterogeneous even between patients with the same disease (Woolf & Decosterd 1999 Pain Supp. 6: S141-S147; Woolf and Mannion 1999 Lancet 353: 1959-1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45-56). Arthritic pain makes up the majority of the inflammatory pain population. Rheumatoid disease is one of the commonest chronic inflammatory conditions in developed countries and rheumatoid arthritis is a common cause of disability. The exact aetiology of RA is unknown, but current hypotheses suggest that both genetic and microbiological factors may be important (Grennan & Jayson 1994 Textbook of Pain 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36: 679-686; McCarthy et al., 1994 Textbook of Pain 387-395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD), Other Types of Pain Include but are not Limited to;

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis.

Central pain or 'thalamic pain' as defined by pain caused by lesion or dysfunction of the nervous system including but not limited to central post-stroke pain, multiple sclerosis, spinal cord injury, Parkinson's disease and epilepsy.

Heart and vascular pain including but not limited to angina, myocardical infarction, mitral stenosis, pericarditis, Raynaud's phenomenon, scleredoma, scleredoma, skeletal muscle ischemia.

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (EBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis.

Head pain including but not limited to migraine, migraine with aura, migraine without aura cluster headache, tension-type headache.

Orofacial pain including but not limited to dental pain, temporomandibular myofascial pain.

Thus, as a yet further aspect of the present invention, there is provided the use of a compound of formula (I), or a pharmaceutically acceptable ester or salt thereof, in the manufacture of a medicament for the treatment of pain.

As an alternative aspect, there is provided a method for the treatment of pain, comprising administration of a therapeutically effective amount of a compound of formula (I), or a pharmaceutically acceptable ester or salt thereof, to a mammal in need of said treatment.

DETAILED DESCRIPTION OF THE INVENTION

As used herein, the term "halogen" means fluoro, chloro, bromo and iodo, preferably fluoro or chloro.

As used herein, the term "alkyl" means straight or branched chain saturated radicals, including, but not limited to methyl, ethyl, n-propyl, isopropyl.

As used herein, the term "alkoxy" means alkyl-O—, including, but not limited to methoxy, ethoxy, n-propoxy, isopropoxy.

As used herein, the term "alkanoyl" means a group having carbonyl such as R'—C(O)— wherein R' is H, $C_{1-5}$ alkyl, phenyl or $C_{3-6}$ cycloalkyl, including, but not limited to formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)—, cyclopentyl-C(O)—, cyclohexyl-C(O)—, and the like.

As used herein, the term "aryl" means a monocyclic or bicyclic aromatic carbocyclic ring of 6 to 10 carbon atoms; including, but not limited to, phenyl or naphthyl, preferably phenyl.

As used herein, the term "cycloalkyl" means a saturated carbocyclic radical ring of 3 to 6 carbon atoms, including, but not limited to, cyclopropyl, cyclobutyl, cyclohexyl, cycloheptyl, cyclooctyl and the like.

As used herein, the term "heteroaryl" means a C-linked, hetero aromatic group having either from 1 to 4 ring nitrogen heteroatoms or 1 or 2 nitrogen ring heteroatoms and 1 oxygen or 1 sulfur ring heteroatom, including, but not limited to, pyrazolyl, furyl, thienyl, oxazolyl, isoxazolyl, tetrazolyl, thiazolyl, isothiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl, quinolyl, isoquinolyl, imidazopyridyl, benzimidazolyl, indolyl, and the like.

As used herein, the term "haloalkyl", as used herein, means an alkyl radical which is substituted by halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

Where the compounds of formula (I) contain hydroxy groups, they may form esters. Examples of such esters include esters with a hydroxy group and esters with a carboxy group. The ester residue may be an ordinary protecting group or a protecting group which can be cleaved in vivo by a biological method such as hydrolysis.

The term "protecting group" means a group, which can be cleaved by a chemical method such as hydrogenolysis, hydrolysis, electrolysis or photolysis.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

In a preferred aspect (A), the invention provides a compound of the formula (I), or a pharmaceutically acceptable ester or salt thereof, wherein $R^1$ and $R^2$ independently represent a hydrogen atom or a fluorine atom. More preferably, $R^1$ and $R^2$ represent a hydrogen atom, or $R^1$ represents a hydrogen atom and $R^2$ represents a fluorine atom, and $R^3$, X, Y and n are as defined above.

In a further preferred aspect (B), the invention provides a compound of the formula (1), or a pharmaceutically acceptable ester or salt thereof, wherein $R^1$ and $R^2$ are defined above, either in its broadest aspect or in a preferred, more or most preferred aspect under (A), $R^3$ represents a phenyl group or a heteroaryl group and said heteroaryl group is a 5- to 6-membered hetero aromatic group containing from 1 to 2 nitrogen heteroatoms or 1 or 2 nitrogen heteroatoms and 1 oxygen or 1 sulfur atom; said phenyl group and heteroaryl group are optionally substituted by 1 to 3 groups selected from a halogen atom, a hydroxy group, an alkyl group having from 1 to 3 carbon atoms, an alkyl group having from 1 to 6 carbon atoms interrupted by an oxgen atom, a hydroxyalkyl group having from 1 to 3 carbon atoms, an amino group and an alkylsulfonylamino group having from 1 to 3 carbon atoms. More preferably, $R^3$ represents a phenyl group or a heteroayl group selected from a pyridyl group, a thiazolyl group, a pyrazolyl group and an oxazolyl group; said phenyl group is optionally substituted by 1 to 3 groups selected from a fluorine atom, a chlorine atom, a hydroxy group, a methyl group, a methoxymethyl group, a hydroxymethyl group, an amino group and methanesulfonylamino. Most preferably, $R^3$ represents a pyridyl group, a thiazolyl group and a pyrazolyl group and X, Y and n are as defined above.

In a further preferred aspect (C), the invention provides a compound of the formula (I), or a pharmaceutically acceptable ester or salt thereof, wherein $R^1$ and $R^2$ are defined above, either in its broadest aspect or in a preferred, more or most preferred aspect under (A), or (B), $R^3$ is defined above, either in the broadest aspect or in a preferred or more preferred aspect under (B), —X—Y— represents a group of the formula —N($R^4$)C(=O)—, —C(=O)N($R^4$)—, —N($R^4$)CH$_2$—, —CH$_2$N($R^4$)—, —N($R^4$)SO$_2$—, —SO$_2$N ($R^4$)—, —CH$_2$CH$_2$—, —CH=CH—, —CH(CH$_2$OH) CH$_2$—, —CH$_2$CH(CH$_2$OH)—, —CH$_2$CH(OH)—, —CH (OH)CH$_2$—, —C($R^4$)($R^5$)—O— or —O—C($R^4$)($R^5$)—. More preferably, —X—Y— represents a group of the formula —N(CH$_3$)C(=O)—, —CH$_2$O—, —CH(CH$_3$)O—, C(CH$_3$)$_2$O— or —CH$_2$CH$_2$—. n is as defined above.

In a further preferred aspect (D), the invention provides a compound of the formula (I), or a pharmaceutically acceptable ester or salt thereof, wherein $R^1$ and $R^2$ are defined above, either in its broadest aspect or in a preferred, more or most preferred aspect under (A), (B) or (C), $R^3$ is defined above, either in the broadest aspect or in a preferred or more preferred aspect under (B) or (C), —X—Y— is defined above, either in its broadest aspect or in a preferred or more preferred aspect under (C), n represents an integer 0.

Individual preferred $R^1$ through $R^3$ and X, Y and n groups are those defined by the $R^1$ through $R^3$ and X, Y and n groups in the Examples section below.

Particularly preferred compounds of the invention include those in which each variable in Formula (I) is selected from the preferred groups for each variable. Even more preferable compounds of the invention include those where each variable in Formula (I) is selected from the more or most preferred groups for each variable.

A specific compound according to the invention is selected from the list consisting of:

2-Benzyl-3-(2,3-dihydro-1'H-spiro[indene-1,4'-piperidin]-1'-yl)propanoic acid trifluoroacetate;

2-(2-Chlorobenzyl)-3-(1'H,3H-spiro[2-benzofuran-1,4'-piperidin]-1'-yl)propanoic acid trifluoroacetate;

2-(5-{[tert-Butyl(dimethyl)silyl]oxy}-2-fluorobenzyl)-3-(1'H,3H-spiro[2-benzofuran-1,4'-piperidin]-1'-yl)propanoic acid trifluoroacetate;

2-(2-Chloro-5-hydroxybenzyl)-3-(1'H,3H-spiro[2-benzofuran-1,4'-piperidin]-1'-yl)propanoic acid;

2-(2-Chlorobenzyl)-3-(1-methyl-2-oxo-1,2-dihydro-1'H-spiro [indole-3,4'-piperidin]-1'-yl)propanoic acid;

2-(2-Chlorobenzyl)-3-(5-fluoro-1-methyl-1,2-dihydro-1'H-spiro[indole-3,4'-piperidin]-1'-yl)propanoic acid;

2-(2-Fluoro-5-hydroxybenzyl)-3-(1-methyl-2-oxo-1,2-dihydro-1'H-spiro[indole-3,4'-piperidin]-1'-yl)propanoic acid;

2-(2-Chlorobenzyl)-3-(6-fluoro-1'H,3H-spiro[2-benzofuran-1,4'-piperidin]-1'-yl)propanoic acid;

2-(2-Chloro-5-hydroxybenzyl)-3-(1-methyl-2-oxo-1,2-dihydro-1'H-spiro[indole-3,4'-piperidin]-1'-yl)propanoic acid;

2-(5-{[tert-Butyl(dimethyl)silyl]oxy}-2-fluorobenzyl)-3-(5-fluoro-1-methyl-1,2-dihydro-1'H-spiro[indole-3,4'-piperidin]-1'-yl)propanoic acid trifluoroacetate;

2-(5-{[tert-Butyl(dimethyl)silyl]oxy}-2-chlorobenzyl)-3-(5-fluoro-1-methyl-1,2-dihydro-1'H-spiro[indole-3,4'-piperidin]-1'-yl)propanoic acid trifluoroacetate;

2-(2-Chloro-5-hydroxybenzyl)-3-(5-fluoro-1-methyl-2-oxo-1,2-dihydro-1'H-spiro[indole-3,4'-piperidin]-1'-yl)propanoic acid;

2-(2-Fluoro-5-hydroxybenzyl)-3-(5-fluoro-1-methyl-2-oxo-1,2-dihydro-1'H-spiro[indole-3,4'-piperidin]-1'-yl)propanoic acid;

2-(2-Chloro-5-hydroxybenzyl)-3-(2-hydroxy-2,3-dihydro-1'H-spiro[indene-1,4'-piperidin]-1'-yl)propanoic acid;

2-(2-chloro-5-hydroxybenzyl)-3-(3-methyl-1'H,3H-spiro[2-benzofuran-1,4'-piperidin]-1'-yl)propanoic acid;

2-(2-Chloro-5-hydroxybenzyl)-3-[3-(hydroxymethyl)-2,3-dihydro-1'H-spiro[indene-1,4'-piperidin]-1'-yl]propanoic acid; 2-(2-chloro-5-hydroxybenzyl)-3-(3-hydroxy-2,3-dihydro-1'H-spiro[indene-1,4'-piperidin]-1'-yl)propanoic acid;

2-(2-Chloro-5-hydroxybenzyl)-3-(5-fluoro-1'H,3H-spiro[2-benzofuran-1,4'-piperidin]-1'-yl)propanoic acid;

3-(3-Methyl-1'H,3H-spiro[2-benzofuran-1,4'-piperidin]-1'-yl)-2-(pyridin-2-ylmethyl)propanoic acid;

3-(3-Methyl-1'H,3H-spiro[2-benzofuran-1,4'-piperidin]-1'-yl)-2-(1,3-thiazol-4-ylmethyl)propanoic acid trifluoroacetate;

3-(3,4-Dihydro-1'H-spiro[isochromene-1,4'-piperidin]-1'-yl)-2-(1,3-thiazol-4-ylmethyl)propanoic acid trifluoroacetate;

3-(5-Fluoro-1-methyl-2-oxo-1,2-dihydro-1'H-spiro[indole-3,4'-piperidin]-1'-yl)-2-(1,3-thiazol-4-ylmethyl)propanoic acid trifluoroacetate;

3-(2,3-Dihydro-1'H-spiro[indene-1,4'-piperidin]-1'-yl)-2-(1,3-thiazol-4-ylmethyl)propanoic acid trifluoroacetate;

3-(2,3-Dihydro-1'H-spiro[indene-1,4'-piperidin]-1'-yl)-2-(1H-pyrazol-1-ylmethyl)propanoic acid;

3-(6-Fluoro-3,4-dihydro-1'H-spiro[isochromene-1,4'-piperidin]-1'-yl)-2-(1H-pyrazol-1-ylmethyl)propanoic acid; and 3-(6-Fluoro-3,4-dihydro-1'H-spiro[isochromene-1,4'-piperidin]-1'-yl)-2-(1,3-thiazol-4-ylmethyl)propanoic acid trifluoroacetate;

or a pharmaceutically acceptable ester thereof.

or a pharmaceutically acceptable salt thereof.

General Synthesis:

The compounds of formula I of the present invention may be prepared according to known preparation methods, or General Procedures or preparation methods illustrated in the following reaction schemes. Unless otherwise indicated $R^1$ through $R^6$ and X, Y, and n in the reaction schemes and discussion that follow are defined as above. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1999);

The following reaction schemes illustrate the preparation of compounds of formula (I).

Scheme 1:

This illustrates the preparation of compounds of formula (I).

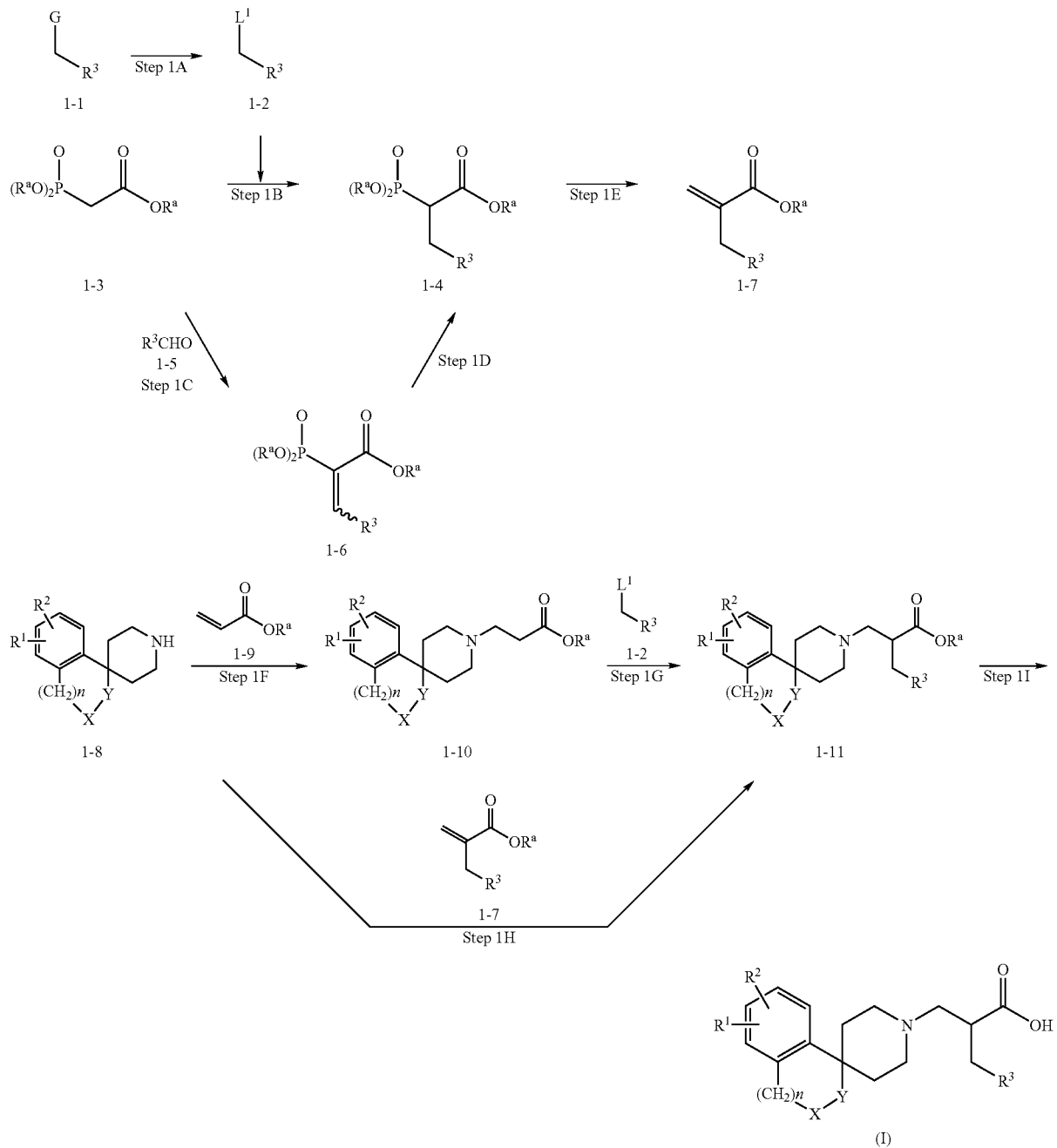

In the above formula, G represents a hydrogen atom or a hydroxy group. $R^a$ represents an alkyl group having from 1 to 4 carbon atoms. $L^1$ represents a leaving group. Examples of suitable leaving groups include: halogen atoms, such as chlorine, bromine and iodine; sulfonic esters such as TfO (triflates), MsO (mesylates), TsO (tosylates); and the like.

Step 1A

In this step, a compound of the formula 1-2 in which $L^1$ represents a halogen atom can be prepared by the halogenating the compound of the formula 1-1 in which G represents a hydrogen atom under halogenation conditions with a halogenating reagent in a reaction-inert solvent.

Examples of suitable solvents include: tetrahydrofuran, 1,4-dioxane, N,N-dimethylformamide, acetonitrile; alcohols, such as methanol or ethanol; halogenated hydrocarbons, such as dichloromethane, 1,2-dichloroethane; chloroform or carbon tetrachloride and acetic acid. Suitable halogenating reagents include, for example, bromine, chlorine, iodine, N-chlorosuccimide, N-bromosuccimide, 1,3-dibromo-5,5-dimethylhydantoin, bis(dimethylacetamide) hydrogen tribromide, tetrabutylammonium tribromide, bromodimethylsulfonium bromide, hydrogen bromide-hydrogen peroxide, nitrodibromoacetonitrile or copper(II) bromide. The reaction can be carried out at a temperature of from 0° C. to 200° C., more preferably from 20° C. to 120° C. Reaction times are, in general, from 5 minutes to 48 hours, more preferably 30 minutes to 24 hours, will usually suffice.

The compound of the formula 1-2 in which $L^1$ represents a halogen atom or a sulfonic ester can also be prepared by the halogenating or sulfonating the compound of the formula 1-1 in which G represents a hydroxy group under conditions known to those skilled in the art.

For example, the hydroxy group of the compound of formula 1-1 may be converted to the halogen atom using a halogenating agent in the presence or absence of a reaction inert solvent. Preferred halogenating agents include: chlorinating agents, such as thionyl chloride, oxalyl chloride, p-toluenesulfonyl chloride, methanesulfonyl chloride, hydrogen chloride, phosphorus trichloride, phosphorus pentachloride, phosphorus oxychloride, or phosphorus reagents such as triphenylphosphine, tributyl phosphine or triphenylphosphite in the presence of halogen source such as carbon tetrachloride, chlorine, N-chlorosuccinimide (NCS); brominating agents, such as hydrogen bromide, N-bromosuccinimide (NBS), phosphorus tribromide, trimethylsilyl bromide or phosphorus reagents such as triphenylphosphine, tributyl phosphine or triphenylphosphite in the presence of halogen source such as carbon tetrabromide, bromine or NBS; and iodinating agents, such as hydroiodic acid, phosphorus triiodide, or phosphorus reagents such as triphenylphosphine, tributyl phosphine or triphenylphosphite in the presence of halogen source such as iodine. Examples of suitable solvents include: aliphatic hydrocarbons, such as hexane, heptane and petroleum ether; aromatic hydrocarbons, such as benzene, toluene, o-dichlorobenzene, nitrobenzene, pyridine, and xylene; halogenated hydrocarbons, such as dichloromethane, chloroform, carbon tetrachloride and 1,2-dichloroethane; and ethers, such as diethyl ether, diisopropyl ether, tetrahydrofuran and 1,4-dioxane. This reaction may be carried out at a temperature in the range from −100° C. to 250° C., more preferably from 0° C. to the reflux temperature for 1 minute to a day, more preferably from 20 minutes to 5 hours.

Alternatively, the hydroxy group of the compound of formula 1-1 may be converted to the sulfonate group using a sulfonating agent in the presence of, or absence of a base. Example of such sulfonating agents includes: p-toluenesulfonyl chloride, p-toluenesulfonic anhydride, methanesulfonyl chloride, methanesulfonic anhydride, trifluoromethanesulfonic anhydride, or the like in the presence or absence of a reaction-inert solvent. Example of such bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of a reaction-inert solvent. Examples of suitable solvents include: aliphatic hydrocarbons, such as hexane, heptane and petroleum ether; aromatic hydrocarbons, such as benzene, toluene, o-dichlorobenzene, nitrobenzene, pyridine, and xylene; halogenated hydrocarbons, such as methylene chloride, chloroform, carbon tetrachloride and 1,2-dichloroethane; and ethers, such as diethyl ether, diisopropyl ether, tetrahydrofuran and 1,4-dioxane; N,N-dimethylformamide, and dimethylsulfoxide. This reaction may be carried out at a temperature in the range from −50° C. to 100° C., more preferably from −10° C. to 50° C. for 1 minute to a day, more preferably from 20 minutes to 5 hours.

Step 1B

In this step, a compound of formula 1-4 can be prepared by the alkylation of a compound of formula 1-3 with the alkylating agent 1-2 in the presence of a base in a reaction-inert solvent. Examples of suitable solvents include: tetrahydrofuran, N,N-dimethylformamide, dimethylsulfoxide, diethylether, toluene, ethylene glycol dimethylether generally or 1,4-dioxane. Examples of suitable bases include: alkyl lithiums, such as n-butyllithium, sec-butyllithium or tert-butyllithium; aryllithiums, such as phenyllithium or lithium naphtilide; methalamide such as sodium amide or lithium diisopropylamide; and alkali metal, such as potassium hydride or sodium hydride. This reaction may be carried out at a temperature in the range from −50° C. to 200° C., usually from −10° C. to 100° C. for 5 minutes to 72 hours, usually 30 minutes to 36 hours.

Step 1C

In this step, a compound of formula 1-6 can be prepared by the aldol condensation of a compound of formula 1-3 with an aldehyde compound 1-5 in the presence of a base in a reaction-inert solvent. Examples of suitable solvents include: tetrahydrofuran, N,N-dimethylformamide, dimethylsulfoxide, ether, toluene, ethylene glycol dimethylether or 1,4-dioxane. Examples of suitable bases include: lithium hydroxide, sodium hydroxide, potassium hydroxide, barium hydroxide, sodium carbonate, potassium carbonate, sodium bicarbonate, cesium carbonate, thallium(I) carbonate, sodium ethoxide, potassium tert-butoxide, potassium acetate, cesium fluoride, tetrabutylammonium fluoride, tetrabutylammonium chloride, tetrabutylammonium iodide, pyridine, picoline, 4-(N,N-dimethylamino)pyridine, triethylamine, tributylamine, diisopropylethylamine, N-methylmorphorine and N-methylpiperidine. This reaction may be carried out at a temperature in the range from −50° C. to 250° C., usually from −10° C. to 150° C. for 5 minutes to 72 hours, usually 30 minutes to 24 hours.

Step 1D

In this step, the compound of formula 1-4 can be prepared by the reduction of the olefin compound of formula 1-6 with a reducing agent in an inert solvent. Examples of suitable solvents include: methanol, ethanol, ethyl acetate, tetrahydrofuran (THF) or mixtures thereof. The reduction may be carried out under known hydrogenation conditions in the presence of a metal catalyst, e.g. nickel catalysts such as Raney nickel, palladium catalysts such as Pd—C, platinum catalysts such as $PtO_2$, or ruthenium catalysts such as $RuCl_2(Ph_3P)_3$ under hydrogen atmosphere or in the presence of hydrogen sources such as hydrazine or formic acid. If desired, the reaction is carried out under acidic conditions, e.g. in the presence of hydrochloric acid or acetic acid. This reaction may be carried out at a temperature in the range from –50° C. to 200° C., usually from –10° C. to 100° C. for 5 minutes to 72 hours, usually 30 minutes to 36 hours.

Step 1E

In this step, a compound of formula 1-7 can be prepared by Horner-Emmons reaction of the compound of formula 1-4 with formaldehyde or paraformaldehyde in the presence of a base in a reaction-inert solvent. Examples of suitable solvents include: tetrahydrofuran, N,N-dimethylformamide, dimethylsulfoxide, diethylether, toluene, ethylene glycol dimethylether, water or 1,4-dioxane. Examples of suitable bases include: lithium hydroxide, sodium hydroxide, potassium hydroxide, barium hydroxide, sodium carbonate, potassium carbonate, sodium bicarbonate, cesium carbonate, thallium(I) carbonate, sodium methoxide, sodium ethoxide, potassium tert-butoxide, potassium hydride or sodium hydride. This reaction may be carried out at a temperature in the range from 0° C. to 200° C., usually from 50° C. to 150° C. for 5 minutes to 72 hours, usually 30 minutes to 50 hours.

Step 1F

In this step, a compound of formula 1-10 can be prepared by Michael reaction of a compound of formula 1-8 with an enone compound of formula 1-9 in the presence of a base in a reaction-inert solvent. Examples of suitable solvents include: acetonitrile, tetrahydrofuran, N,N-dimethylformamide, dimethylsulfoxide, ether, toluene, ethylene glycol dimethylether, water or 1,4-dioxane. Examples of suitable bases include: triethylamine, tributylamine, diisopropylethylamine, pyridine, picoline, N-methylmorphorine and N-methylpiperidine, sodium carbonate, potassium carbonate, sodium bicarbonate, cesium carbonate. This reaction may be carried out at a temperature in the range from 0° C. to 200° C., usually from 25° C. to 100° C. for 5 minutes to 60 hours, usually 30 minutes to 30 hours.

Step 1G

In this step, a compound of formula 1-11 can be prepared by the alkylation of a compound of formula 1-10 with the alkylating agent 1-2 in the presence of a base in a reaction-inert solvent. Examples of suitable solvents include: tetrahydrofuran, diethylether, toluene, ethylene glycol dimethylether generally or 1,4-dioxane. Examples of suitable bases include: lithium bis(trimethylsilyl)amide, sodium bis(trimethylsilyl)amide, pottasium bis(trimethylsilyl)amide, methalamide such as sodium amide or lithium diisopropylamide; and alkali metal, such as potassium hydride or sodium hydride. If desired, this reaction may be carried out in the presence or absence of an additive such as N,N'-dimethylpropyleneurea (DMPU), hexamethylphosphoramide (HMPA), N,N,N',N'-tetramethylethylenediamine (TMEDA). This reaction may be carried out at a temperature in the range from –100° C. to 200° C., usually from –80° C. to 100° C. for 5 minutes to 72 hours, usually 30 minutes to 36 hours.

Step 1H

In this step, the compound of formula 1-11 can be prepared by Michael reaction of the compound of formula 1-8 with the enone compound of formula 1-7 in the presence or absence of a base in a reaction-inert solvent. Examples of suitable solvents include: methanol, ethanol, tetrahydrofuran, N,N-dimethylformamide, dimethylsulfoxide, diethylether, toluene, ethylene glycol dimethylether, water or 1,4-dioxane. Examples of suitable bases include: triethylamine, tributylamine, diisopropylethylamine, pyridine, picoline, N-methylmorphorine and N-methylpiperidine. This reaction may be carried out at a temperature in the range from 0° C. to 200° C., usually from 25° C. to 100° C. for 1 hour to 2 weeks, usually 5 hours to 10 days.

Step 1I

In this step, an acid compound of formula 1-12 may be prepared by hydrolysis of the ester compound of formula 1-11 in a solvent.

The hydrolysis may be carried out by conventional procedures. In a typical procedure, the hydrolysis carried out under the basic condition, e.g. in the presence of sodium hydroxide, potassium hydroxide or lithium hydroxide. Suitable solvents include, for example, alcohols such as methanol, ethanol, propanol, butanol, 2-methoxyethanol, and ethylene glycol; ethers such as tetrahydrofuran (THF), 1,2-dimethoxyethane (DME), and 1,4-dioxane; amides such as N,N-dimethylformamide (DMF) and hexamethylphospholictriamide; and sulfoxides such as dimethyl sulfoxide (DMSO). This reaction may be carried out at a temperature in the range from –20° C. to 100° C., usually from 20° C. to 75° C. for 30 minutes to 48 hours, usually 60 minutes to 30 hours.

The hydrolysis may also be carried out under the acidic condition, e.g. in the presence of hydrogen halides, such as hydrogen chloride and hydrogen bromide; sulfonic acids, such as p-toluenesulfonic acid and benzenesulfonic acid; pyridium p-toluenesulfonate; and carboxylic acid, such as acetic acid and trifluoroacetic acid. Suitable solvents include, for example, alcohols such as methanol, ethanol, propanol, butanol, 2-methoxyethanol, and ethylene glycol; ethers such as tetrahydrofuran (THF), 1,2-dimethoxyethane (DME), and 1,4-dioxane; halogenated hydrocarbons, such as dichloromethane, 1,2-dichloroethane, amides such as N,N-dimethylformamide (DMF) and hexamethylphospholictriamide; and sulfoxides such as dimethyl sulfoxide (DMSO). This reaction may be carried out at a temperature in the range from –20° C. to 100° C., usually from 0° C. to 65° C. for 30 minutes to 24 hours, usually 60 minutes to 10 hours.

Scheme 2

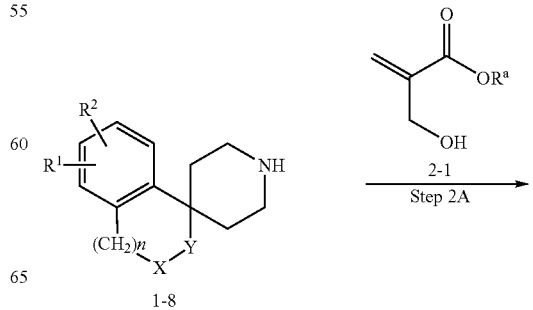

1-8

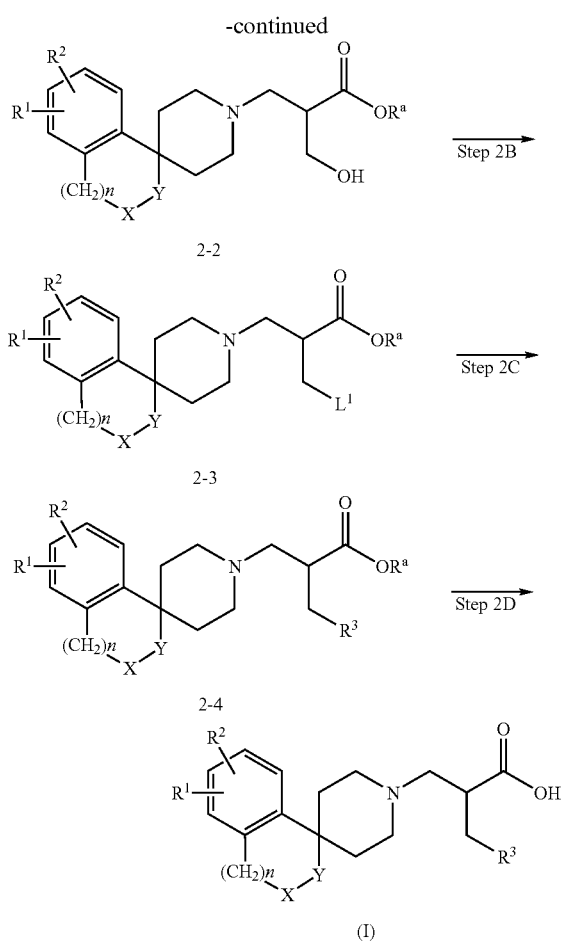

In the above formula, $R^a$ and $L^1$ are defined above.

Step 2A

In this step, a compound of formula 2-2 may be prepared by Michael reaction of the compound of formula 1-8 with an enone compound of formula 2-1. This reaction is essentially the same as and may be carried out in the same manner as and using the same reagents and reaction conditions as Step 1H in Scheme 1.

Step 2B

In this step, the compound of formula 2-3 may be converted to a compound with a leaving group $L^1$ of formula 2-2 under conditions known to those skilled in the art. This reaction is essentially the same as and may be carried out in the same manner as and using the same reagents and reaction conditions as Step 1A in Scheme 1.

Step 2C

In this step, a compound of formula 2-4 can be prepared by replacement of the leaving group of the compound of formula 2-3 with the compound of formula $R^3H$ in the presence of a base in a reaction-inert solvent. Examples of suitable solvents include: acetonitrile, tetrahydrofuran, N,N-dimethylformamide, dimethylsulfoxide, ether, toluene, ethylene glycol dimethylether or 1,4-dioxane. Examples of suitable bases include: lithium hydroxide, sodium hydroxide, potassium hydroxide, barium hydroxide, sodium carbonate, potassium carbonate, sodium bicarbonate, cesium carbonate, thallium(I) carbonate, sodium ethoxide, potassium tert-butoxide, potassium acetate, cesium fluoride, tetrabutylammonium fluoride, tetrabutylammonium chloride, tetrabutylammonium iodide, pyridine, picoline, 4-(N,N-dimethylamino)pyridine, triethyl amine, tributyl amine, diisopropylethylamine, N-methylmorphorine and N-methylpiperidine. This reaction may be carried out at a temperature in the range from 0° C. to 250° C., usually from −10° C. to 150° C. for 5 minutes to 72 hours, usually 30 minutes to 36 hours.

Step 2D

In this step, a compound of formula (I) may be prepared by hydrolysis of the compound of formula 2-4. This reaction is essentially the same as and may be carried out in the same manner as and using the same reagents and reaction conditions as Step 1I in Scheme 1.

In the above Schemes from 1 to 3, examples of suitable solvents include a mixture of any two or more of those solvents described in each step.

The starting materials in the aforementioned general syntheses are commercially available or may be obtained by conventional methods known to those skilled in the art.

The compounds of formula (I), and the intermediates above-mentioned preparation methods can be isolated and purified by conventional procedures, such as recrystallization or chromatographic purification.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

Method for Assessing Biological Activities:

The compounds of Formula (I) have been found to possess affinity for ORL1-receptors and ORL-1 receptor antagonist activity. Thus, these compounds are useful as an analgesic, anti-inflammatory, diuretic, anesthetic, neuroprotective, anti-hypertensive and anti-anxiety agent, and the like, in mammalian subjects, especially humans in need of such agents. The affinity, antagonist activities and analgesic activity can be demonstrated by the following tests respectively.

Affinity for ORL1-Receptors:

ORL1-Receptor Binding Assay:

The human ORL1 receptor transfected HEK-293 cell membranes (PerkinElmer) were incubated for 45 min at room temperature with 0.4 nM [$^3$H]nociceptin, 1.0 mg of wheat germ agglutinin(WGA)-coated SPA beads and various concentrations of test compounds in a final volume of 200 μL of 50 mM HEPES buffer pH 7.4 containing 10 mM $MgCl_2$ and 1 mM EDTA. Non-specific binding (NSB) was determined by the addition of 1 μM unlabeled nociceptin. After the reaction, the assay plate was centrifuged at 1,000 rpm for 1 min and then the radioactivity was measured by WALLAC 1450 MicroBeta Trilux.

μ-Receptor Binding Assay:

The human Mu receptor transfected CHO-K1 cell membranes (PerkinElmer) were incubated for 45 min at room temperature with 1.0 nM[$^3$H]DAMGO, 1.0 mg of WGA-coated SPA beads and various concentrations of test compounds in a final volume of 200 μl of 50 mM Tris-HCl buffer pH 7.4 containing 5 mM $MgCl_2$. NSB was determined by the addition of 1 μM unlabeled DAMGO. After the reaction, the assay plate was centrifuged at 1,000 rpm for 1 min and then the radioactivity was measured by WALLAC 1450 MicroBata Trilux.

Each percent NSB thus obtained was graphed as a function of compound concentration. A sigmoidal curve was used to determine 50% bindings (i.e., $IC_{50}$ values).

In this testing, the preferred compounds prepared in the working examples appearing hereafter demonstrated higher binding affinity for ORL1-receptors than for mu-receptors.

$IC_{50}$ (ORL1-receptors) nM/$IC_{50}$ (mu-receptors) nM<1.0.

ORL1 Receptor Functional Assay:

The human ORL1 receptor transfected HEK-293 cell membranes were incubated with 400 pM [$^{35}$S]GTPγS, 10 nM nociceptin and various concentrations of test compounds in assay buffer (20 mM HEPES, 100 mM NaCl, 5 mM $MgCl_2$, 1 mM EDTA, 5 μM GDP, 1 mM DTT, pH 7.4) containing 1.5 mg of WGA-coated SPA beads for 90 min at room temperature in a final volume of 200 μL. Basal binding was assessed in the absence of nociceptin and NSB was defined by the addition of unlabelled 10 μM GTPγS. Membrane-bound radioactivity was detected by a Wallac 1450 MicroBeta liquid scintillation counter.

Analgesic Tests:

Tail Flick Test in Mice:

The latency time to withdrawal of the tail from radiant heat stimulation is recorded before and after administration of test compounds. Cut-off time is set to 8 sec.

Acetic Acid Writhing Test in Mice:

Acetic acid saline solution of 0.7% (v/v) is injected intraperitoneally (0.16 mL/10 g body weight) to mice. Test compounds are administered before acetic acid injection. As soon as acetic acid injection, animals are placed in a 1 L beaker and writhing is recorded for 15 min.

Formalin Licking Test in Mice:

Formalin-induced hind paw licking is initiated by a 20 μL subcutaneous injection of a 2% formalin solution into a hind paw of mice. Test compounds are administered prior to formalin injection. Total licking time is recorded for 45 min after formalin injection.

Carrageenan-Induced Mechanical Hyperalgesia Test in Rats:

The response to mechanical nociceptive stimulus is measured using an algesiometer (Ugo Basile, Italy). The pressure is loaded to the paw until rats withdrawal the hind paw. Lambda-Carrageenan saline solution of 1% (w/v) is injected subcutaneously into the hind paw and the withdrawal response is measured before and after the injection. Test compounds are administered at appropriate time point.

Carrageenan-Induced Thermal Hyperalgesia Test in Rats:

The response to thermal nociceptive stimulus is measured using a plantar test apparatus (Ugo Basile, Italy). The radiant heat stimuli is applied to the paw until rats withdrawal the hind paw. Lambda-Carrageenan saline solution of 2% (w/v) is injected subcutaneously into the hind paw and the withdrawal response is measured before and after the injection. This testing method is described in K. Hargreaves, et al., Pain 32:77-88, 1988.

Chronic Contriction Injury Model (CCI Model):

Chronic contriction injury is made according to Bennett's method (Bennett and Xie, Pain 33:87-107, 1988). Tactile allodynia in rats is assessed using the von Frey hairs (Stoelting, Ill.) before and after administration with test compounds.

Partial Sciatic Nerve Ligation Model (PSL):

This test may be conducted according to similar procedures described by Z. Seltzer, et al. (Pain, 43:205-218, 1990) (Title: A novel behavioral model of neuropathic pain disorders produced in rats by partial sciatic nerve injury).

Dofetilide Binding Assay:

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000 g for 20 min at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 sec. The membrane homogenate was aliquoted and stored at −80° C. until use. Analiquot was used for protein concentration determination using a Protein Assay Rapid Kit and ARVO SX plate reader (Wallac). All the manipulation, stock solution and equipment were kept on ice at all the time. For saturation assays, experiments were conducted in a total volume of 200 μL. Saturation was determined by incubating 20 μL of [$^3$H]-dofetilide and 160 μl of membrane homogenates (20-30 μg protein per well) for 60 min at room temperature in the absence or presence of 10 μM dofetilide at final concentrations (20 μL) for total or nonspecific binding, respectively. All incubations were terminated by rapid vacuum filtration over PEI soaked glass fiber filter papers using Skatron cell harvester followed by two washes with 50 mM Tris buffer (pH 7.5 at 25° C.). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.5 at 25° C.) containing 1 mM $MgCl_2$, 10 mM KCl so that the final DMSO concentration became equal to 1%. Compounds were dispensed in triplicate in assay plates (4 μL). Total binding and nonspecific binding wells were set up in 6 wells as vehicle and 10 μM dofetilideat final concentration, respectively. The radio ligand was prepared at 5.6× final concentration and this solution was added to each well (36 μL). The assay was initiated by addition of YSi poly-L-lysine SPA beads (50 μL, 1 mg/well) and membranes (110 μL, 20 μg/well). Incubation was continued for 60 min at room temperature. Plates were incubated for a further 3 hours at room temperature for beads to settle. Receptor-bound radio activity was quantified by counting Wallac MicroBeta plate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical journal, 74, pp230-241). Before the day of experimentation, the cells were harvested from culture flasks and plated onto glass coverslips in a standard MEM medium with 10% FCS. The plated cells were stored in an incubator at 37° C. maintained in an atmosphere of 95%$O_2$/5%$CO_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MΩ and seal resistances >1 GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient for cell dialysis with pipette solution (>5 min), a standard voltage protocol was applied to the cell to evoke membrane currents. The voltage protocol is as follows. The membrane was depolarized from a holding potential of −80 mV to +20 mV for 1000 ms. This was followed by a descending voltage ramp (rate 0.5 mV $msec^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10-20 min by a peristalic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There reversibility. Finally, the cells was exposed to high dose of dofetilide (5 μM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under control conditions and in the presence of drug. Percent decrease of $I_N$ in each experiment was obtained by the normalized current value using the following formula: $I_N=(1-I_D/I_C)\times100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:
(i) where the compound of formula (I) contains a carboxylic acid functionality (—COOH), an ester thereof, for example, replacement of the hydrogen with $(C_1-C_8)$alkyl;
(ii) where the compound of formula (I) contains an alcohol functionality (—OH), an ether thereof, for example, replacement of the hydrogen with $(C_1-C_6)$alkanoyloxymethyl; and
(iii) where the compound of formula (I) contains a primary or secondary amino functionality (—NH$_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

The term "ester" or "amide" means a protecting group which can be cleaved in vivo by a biological method such as hydrolysis and forms a free acid or a free amine, or salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of groups for forming an ester with a hydroxy group and for forming an amide with a amino group include: (1) aliphatic alkanoyl groups, for example: alkanoyl groups such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups; halogenated alkylcarbonyl groups such as the chloroacetyl, dichloroacetyl, trichloroacetyl, and trifluoroacetyl groups; alkoxyalkanoyl groups such as the methoxyacetyl group; and unsaturated alkanoyl groups such as the acryloyl, propioloyl, methacryloyl, crotonoyl, isocrotonoyl and (E)-2-methyl-2-butenoyl groups; (2) aromatic alkanoyl groups, for example: arylcarbonyl groups such as the benzoyl, a-naphthoyl and β-naphthoyl groups; halogenated arylcarbonyl groups such as the 2-bromobenzoyl and 4-chlorobenzoyol groups; alkylated arylcarbonyl groups such as the 2,4,6-trimethylbenzoyl and 4-toluoyl groups; alkoxylated arylcarbonyl groups such as the 4-anisoyl group; nitrated arylcarbonyl groups such as the 4-nitrobenzoyl and 2-nitrobenzoyl groups; alkoxycarbonylated arylcarbonyl groups such as the 2-(methoxycarbonyl)benzoyl group; and arylated arylcarbonyl groups such as the 4-phenylbenzoyl group; (3) alkoxycarbonyl groups, for example: alkoxycarbonyl groups such as the methoxycarbonyl, ethoxycarbonyl, propoxycarbonyl, butoxycarbonyl, sec-butoxycarbonyl, t-butoxycarbonyl and isobutoxycarbonyl groups; and halogen- or tri(alkyl)silyl-substituted alkoxycarbonyl groups such as the 2,2,2-trichloroethoxycarbonyl and 2-trimethylsilylethoxycarbonyl groups; tetrahydropyranyl or tetrahydrothiopyranyl groups such as: tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups such as: tetrahydrofuran-2-yl and tetrahydrothiofuran-2-yl groups; (5) silyl groups, for example: tri(alkyl)silyl groups such as the trimethylsilyl, triethylsilyl, isopropyldimethylsilyl, t-butyldimethylsilyl, methyldiisopropylsilyl, methyldi-t-butylsilyl and triisopropylsilyl groups; and silyl groups substituted by one or more aryl and alkyl groups such as the diphenylmethylsilyl, diphenylbutylsilyl, diphenylisopropylsilyl and phenyldiisopropylsilyl groups; (6) alkoxymethyl groups, for example: alkoxymethyl groups such as the methoxymethyl, 1,1-dimethyl-1-methoxymethyl, ethoxymethyl, propoxymethyl, isopropoxymethyl, butoxymethyl and t-butoxymethyl groups; alkoxylated alkoxymethyl groups such as the 2-methoxyethoxymethyl group; and halo(alkoxy)methyl groups such as the 2,2,2-trichloroethoxymethyl and bis(2-chloroethoxy)methyl groups; (7) substituted ethyl groups, for example: alkoxylated ethyl groups such as the 1-ethoxyethyl and 1-(isopropoxy)ethyl groups; and halogenated ethyl groups such as the 2,2,2-trichloroethyl group; (8) aralkyl groups, for example: alkyl groups substituted by from 1 to 3 aryl groups such as the benzyl, α-naphthylmethyl, β-naphthylmethyl, diphenylmethyl, triphenylmethyl, α-naphthyldiphenylmethyl and 9-anthrylmethyl groups; alkyl groups substituted by from 1 to 3 substituted aryl groups, where one or more of the aryl groups is substituted by one or more alkyl, alkoxy, nitro, halogen or cyano substituents such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups such as the vinyloxycarbonyl; aryloxycarbonyl groups such as phenoxycaronyl; and aralkyloxycarbonyl groups in which the aryl ring may be substituted by 1 or 2 alkoxy or nitro groups, such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, N.Y., 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

The compounds of the invention may be administered in combination, separately, simultaneously or sequentially, with one or more other pharmacologically active agents. Suitable agents, particularly for the treatment of pain, include:

(i) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(ii) nonsteroidal antiinflammatory drugs (NSAIDs), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and their pharmaceutically acceptable salts;

(iii) barbiturate sedatives, e.g. amobarbital, aprobarbital, butabarbital, butabital, mephobarbital, metharbital, methohexital, pentobarbital, phenobartital, secobarbital, talbutal, theamylal, thiopental and their pharmaceutically acceptable salts;

(iv) benzodiazepines having a sedative action, e.g. chlordiazepoxide, clorazepate, diazepam, flurazepam, lorazepam, oxazepam, temazepam, triazolam and their pharmaceutically acceptable salts, (v) H$_1$ antagonists having a sedative action, e.g. diphenhydramine, pyrilamine, promethazine, chlorpheniramine, chlorcyclizine and their pharmaceutically acceptable salts;

(vi) miscellaneous sedatives such as glutethimide, meprobamate, methaqualone, dichloralphenazone and their pharmaceutically acceptable salts;

(vii) skeletal muscle relaxants, e.g. baclofen, carisoprodol, chlorzoxazone, cyclobenzaprine, methocarbamol, orphrenadine and their pharmaceutically acceptable salts, (viii) alpha-2-delta ligands, e.g. gabapentin and pregabalin;

(ix) alpha-adrenergic active compounds, e.g. doxazosin, tamsulosin, clonidine and 4-amino-6,7-dimethoxy-2-(5-methanesulfonamido-1,2,3,4-tetrahydroisoquinol-2-yl)-5-(2-pyridyl) quinazoline;

(x) tricyclic antidepressants, e.g. desipramine, imipramine, amytriptiline and nortriptiline;

(xi) anticonvulsants, e.g. carbamazepine and valproate;

(xii) serotonin reuptake inhibitors, e.g. fluoxetine, paroxetine, citalopram and sertraline;

(xiii) mixed serotonin-noradrenaline reuptake inhibitors, e.g. milnacipran, venlafaxine and duloxetine;

(xiv) noradrenaline reuptake inhibitors, e.g. reboxetine;

(xv) Tachykinin (NK) antagonists, particularly NK-3, NK-2 and NK-1 antagonists, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S)

(xvi) Muscarinic antagonists, e.g oxybutin, tolterodine, propiverine, tropsium chloride and darifenacin;

(xvii) COX-2 inhibitors, e.g. celecoxib, rofecoxib and valdecoxib;

(xviii) Non-selective COX inhibitors (preferably with GI protection), e.g. nitroflurbiprofen (HCT-1026);
(xix) coal-tar analgesics, in particular, paracetamol;
(xx) neuroleptics, such as droperidol;
(xxi) Vanilloid receptor agonists, e.g. resinferatoxin;
(xxii) Beta-adrenergic compounds such as propranolol;
(xxiii) Local anaesthetics, such as mexiletine;
(xxiv) Corticosteriods, such as dexamethasone
(xxv) serotonin receptor agonists and antagonists;
(xxvi) cholinergic (nicotinic) analgesics; and
(xxvii) miscellaneous analgesic agents, such as Tramadol®.
(xxviii) NMDA receptor antagonists, e.g. dextromethorphan ((+)-3-hydroxy-N-methylmorphinan) and its metabolite dextrorphan ((+)-3-hydroxy-N-methylmorphinan), ketamine, memantine, pyrroloquinoline quinone and cis-4-(phosphonomethyl)-2-piperidinecarboxylic acid and their pharmaceutically acceptable salts;
(xxix) Prostaglandin $EP_4$ receptor agonists and antagonists;
(xxx) PDEV inhibitors, such as sildenafil, vardenafil or taladafil;

Thus, the invention further provides a combination comprising a compound of the invention or a pharmaceutically acceptable salt, solvate or pro-drug thereof, and a compound or class of compounds selected from the group (i)-(xxx), above. There is also provided a pharmaceutical composition composition comprising such a combination, together with a pharmaceutically acceptable excipient, diluent or carrier, particularly for the treatment of a disease for which a ORL1 antagonist is implicated.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid- formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified controlled release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably, to a pH of from 3 to 9), but, for some applications, they may be more suitably formulated as a sterile non-aqueous solution or as powdered a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for use with needle-free injection administration comprise a compound of the invention in powdered form in conjunction with a suitable vehicle such as sterile, pyrogen-free water.

Formulations for parenteral administration may be formulated to be immediate and/or modified controlled release. Modified release formulations include delayed-, sustained-, pulsed-, controlled-, tragetted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose tio include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated— see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified controlled release. Modified release formulations include delayed-, sustained-, pulsed-, controlled-, tragettedtargeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate committing method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified controlled release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 10 mg of the compound of formula (I). The overall daily dose will typically be in the range 1 µg to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified controlled release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified controlled release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range 0.1 mg to 3000 mg, preferably from 1 mg to 500mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC); melting points (mp) given are uncorrected (polymorphism may result in different melting points); the structure and purity of all isolated compounds were assured by at least one of the following techniques: TLC (Merck silica gel 60 $F_{254}$ precoated TLC plates or Merck $NH_2$ gel (an amine coated silica gel) $F_{254s}$ precoated TLC plates), mass spectrometry, nuclear magnetic resonance spectra (NMR) or infrared red absorption spectra (IR). Yields are given for illustrative purposes only. Workup with a cation-exchange column was carried out using SCX cartridge (Varian BondElute), which was preconditioned with methanol. Flash column chromatography was carried out using Merck silica gel 60 (63-200 µm), Wako silica gel 30OHG (40-60 µm), Fuji Silysia NH gel (an amine coated silica gel) (30-50 µm), Biotage KP-SIL (32-63 µm) or Biotage AMINOSILICA (an amine coated silica gel) (40-75 µm). Preparative TLC was carried out using Merck silica gel 60 $F_{254}$ precoated TLC plates (0.5 or 1.0 mm thickness). Low-resolution mass spectral data (EI) were obtained on an Integrity (Waters) mass spectrometer. Low-resolution mass spectral data (ESI) were obtained on a ZMD (Micromass) mass spectrometer. NMR data was determined at 270 MHz (JEOL JNM-LA 270 spectrometer), 300 MHz (JEOL JNM-LA300 spectrometer) or 600 MHz (Bruker AVANCE 600 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; L (liter(s)), mL (milliliter(s)), g (gram(s)), mg (milligram(s)), mol (moles), mmol (millimoles), eq. (equivalent(s)), quant. (quantitative yield).

Example 1

2-Benzyl-3-(2,3-dihydro-1'H-spiro[indene-1,4'-piperidin]-1'-yl)propanoic acid trifluoroacetate

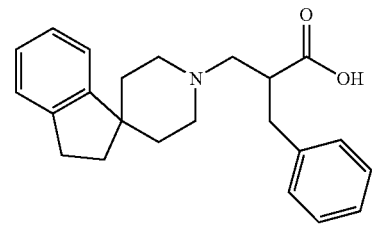

Step 1. tert-Butyl 3-(2,3-dihydro-1'H-spiro[indene-1,4'-piperidin]-1'-yl)propanoate A solution of 2,3-dihydrospiro[indene-1,4'-piperidine] (3.0 g, 13 mmol), tert-butyl acrylate (3.1 g, 24 mmol) and triethylamine (4.5 mL, 32 mmol) in tetrahydrofuran (60 mL) was stirred at 70° C. under nitrogen atmosphere for 1 day. The organic layer was washed with saturated sodium bicarbonate aqueous solution (100 mL). The aqueous layer was extracted with ethyl acetate (150 mL×2). The combined organic layers were washed with brine (50 mL), dried over sodium sulfate, and evaporated. The residue was purified by column chromatography on silica gel eluting with hexane/acetone (4/1) to afford 2.8 g (66%) of the title compound as a yellow oil:

$^1$H-NMR (CDCl$_3$) δ 7.19-7.12 (4H, m), 2.92-2.85 (4H, m), 2.74-2.69 (2H, m), 2.50-2.45 (2H, m), 2.26-2.17 (2H, m), 2.02-1.87 (4H, m), 1.76-1.67 (1H, m), 1.56-1.52 (1H, m), 1.46 (9H, s).

Step 2. tert-Butyl 2-benzyl-3-(2,3-dihydro-1'H-spiro[indene-1,4'-piperidin]-1'-yl)propanoate To a stirred solution of tert-butyl 3-(2,3-dihydro-1'H-spiro[indene-1,4'-piperidin]-1'-yl)propanoate (step 1, 200 mg, 0.63 mmol) in tetrahydrofuran (2 mL) was added dropwise a 1.0 M solution of lithium bis(trimethylsilyl)amide in tetrahydrofuran (0.76 mL, 0.76 mmol) at −78° C. and the mixture was stirred for 30 min at the same temperature. To the mixture was added 1,3-Dimethyl-3,4,5,6-tetrahydro-2(1H)-pyrimidinone (92 µL, 0.76 mmol) at −78° C. and stirred for 30 min at the same temperature. To the resulting mixture was added benzyl bromide (130 mg, 0.76 mmol) and the reaction mixture was stirred at the same temperature for 1 h and then at 0° C. for 1 h. The reaction mixture was quenched by the addition of saturated ammonium chloride aqueous solution. The mixture was extracted with ethyl acetate (20 mL×3), and then the combined organic layers were with brine (50 mL), dried over sodium sulfate, and evaporated. The residue was purified by column chromatography on silica gel eluting with hexane/ethyl acetate (8/1) to afford 88 mg (34%) of the title compound as a colorless oil:

$^1$H-NMR (CDCl$_3$) δ 7.30-7.11 (9H, m), 2.93-2.66 (8H, m), 2.48-2.41 (1H, m), 2.28-2.10 (2H, m), 2.04-1.82 (4H, m), 1.53-1.39 (2H, m), 1.36 (9H, s).

Step 3. 2-Benzyl-3-(2,3-dihydro-1'H-spiro[indene-1,4'-piperidin]-1'-yl)propanoic acid trifluoroacetate To a stirred solution of tert-butyl 2-benzyl-3-(2,3-dihydro-1'H-spiro[indene-1,4'-piperidin]-1'-yl)propanoate (step 2, 88 mg, 0.22 mmol) in dichloromethane (1 mL) was added trifluoroacetic acid (1 mL) and stirred at room temperature for 2 h. The reaction mixture was evaporated to dryness to afford 181 mg (quant.) of the title compound as a yellow oil:

$^1$H-NMR (CDCl$_3$) δ 8.22 (1H, br.s), 7.43-7.04 (9H, m), 3.75-3.25 (5H, m), 3.11-2.74 (6H, m), 2.32-2.13 (2H, m), 2.02-1.97 (2H, m), 1.76-1.71 (2H, m).

Example 2

2-Benzyl-3-(1'H,3H-spiro[2-benzofuran-1,4'-piperidin]-1'-yl)propanoic acid trifluoroacetate

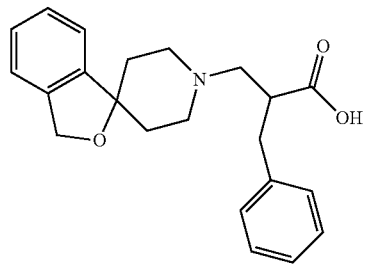

Step 1. tert-Butyl 2-benzyl-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate and benzyl bromide:

$^1$H-NMR (CDCl$_3$) δ 7.32-7.08 (9H, m), 5.06 (2H, s), 2.96-2.69 (6H, m), 2.55-2.31 (3H, m), 2.00-1.84 (2H, m), 1.80-1.68 (2H, m), 1.35 (9H, s); MS (ESI) 408 (M+H)$^+$.

Step 2. 2-Benzyl-3-(1'H,3H-spiro[2-benzofuran-1,4'-piperidin]-1'-yl)propanoic acid trifluoroacetate The title compound was prepared according to the procedure described in step 3 of example 1 from tert-butyl 2-benzyl-3-(1'H,3H-spiro[2-benzofuran-1,4'-piperidin]-1'-yl)propanoate (step 1):

$^1$H-NMR (CDCl$_3$) δ 7.35-7.10 (9H, m), 5.04 (2H, s), 3.70-2.69 (9H, m), 2.50-2.30 (2H, m), 1.90-1.80 (2H, m); MS (ESI) 352 (M+H)$^+$, 350 (M−H)$^-$.

Example 3

2-(3-Methoxybenzyl)-3-(1'H,3H-spiro[2-benzofuran-1,4'-piperidin]-1'-yl)propanoic acid trifluoroacetate

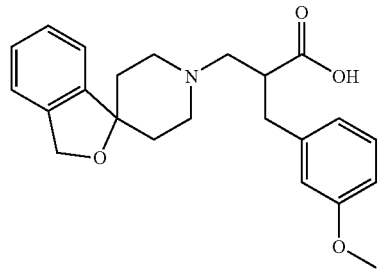

Step 1. tert-Butyl 2-(3-methoxybenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and 1-(bromomethyl)-3-methoxybenzene:

$^1$H-NMR (CDCl$_3$) δ 7.30-7.08 (5H, m), 6.84-6.70 (3H, m), 5.06 (2H, s), 3.79 (3H, s), 2.90-2.68 (6H, m), 2.54-2.32 (3H, m), 1.98-1.84 (2H, m), 1.80-1.68 (2H, m), 1.38 (9H, s); MS (ESI) 438 (M+H)$^+$.

Step 2. 2-(3-Methoxybenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(3-methoxybenzyl)-3-(1'H,3H-spiro[2-benzofuran-1,4'-piperidin]-1'-yl)propanoate (step 1):

$^1$H-NMR (CDCl$_3$) δ 7.35-7.05 (5H, m), 6.84-6.70 (3H, m), 5.04 (2H, s), 3.79 (3H, s), 3.66-3.50 (3H, m), 3.49-3.20 (3H, m), 3.08-3.24 (2H, m), 2.76-2.64 (1H, m), 2.48-2.25 (2H, m), 1.94-1.78 (2H, m); MS (ESI) 382 (M+H)$^+$, 380 (M−H)$^-$.

Example 4

2-Benzyl-3-(5-fluoro-1-methyl-1,2-dihydro-1'H-spiro[indole-3,4'-piperidin]-1'-yl)propanoic acid

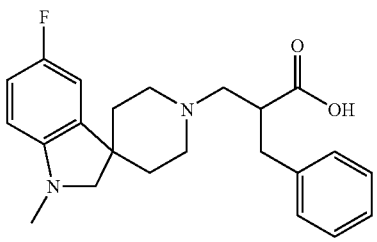

Step 1. Benzyl 5-fluoro-1,2-dihydro-1'H-spiro[indole-3,4'-piperidine]-1'-carboxylate The title compound was prepared according to the procedure described in the literature (*Tetrahedron* 1997, 53, 10983-10992.) from (4-fluorophenyl)hydrazine hydrochloride:
$^1$H-NMR (CDCl$_3$) δ 7.39-7.32 (5H, m), 6.78-6.72 (2H, m), 6.67-6.63 (1H, m), 5.16 (2H, s), 4.16 (2H, br.m), 3.64 (1H, br.m), 3.49 (2H, s), 2.97 (2H, br.m), 1.74 (4H, br.m); MS (ESI) 341 (M+H)$^+$.

Step 2. Benzyl 5-fluoro-1-methyl-1,2-dihydro-1'H-spiro [indole-3,4'-piperidine]-1'-carboxylate To a stirred solution of benzyl 5-fluoro-1,2-dihydro-1'H-spiro[indole-3,4'-piperidine]-1'-carboxylate (step 1, 1.27 g, 3.72 mmol), 37% formaldehyde aqueous solution (1.4 mL, 18.6 mmol), and sodium cyanoborohydride (701 mg, 11.1 mmol) in methanol (30 mL) was added acetic acid (1.06 mL, 18.6 mmol) at room temperature. After being stirred for 20 h, the mixture was quenched by the addition of diluted sodium hydroxide aqueous solution, and then concentrated to give a brown syrup. The crude material was partitioned between ethyl acetate and diluted sodium hydroxide aqueous solution, and then the organic layer was washed with brine, dried over sodium sulfate, and evaporated to afford 1.38 g of the title compounds as a yellow syrup:
$^1$H-NMR (CDCl$_3$) δ 7.39-7.32 (5H, m), 6.93-6.69 (2H, m), 6.40-6.36 (1H, m), 5.16 (2H, s), 4.13 (2H, br.m), 3.23 (2H, s), 3.00 (2H, br.m), 2.73 (3H, s), 1.73 (4H, br.m); MS (ESI) 354 (M+H)$^+$.

Step 3. 5-Fluoro-1-methyl-1,2-dihydrospiro[indole-3,4'-piperidine]

A solution of benzyl 5-fluoro-1-methyl-1,2-dihydro-1'H-spiro[indole-3,4'-piperidine]-1'-carboxylate (step 2, 1.38 g, 3.90 mmol) in trifluoroacetic acid (10 mL) was refluxed for 4.5 h. The reaction mixture was evaporated to give a brown syrup. This crude material was partitioned between dichloromethane and diluted sodium hydroxide aqueous solution, and then the organic layer was dried over sodium sulfate, and evaporated. The residue was purified by column chromatography on an amine coated silica gel (70 g) eluting with dichloromethane, and then dichloromethane/methanol (50/1) to afford 814 mg (95%) of the title compound as a slight brown solid:
MS (ESI) 221 (M+H)$^+$.

Step 4. Ethyl 2-benzyl-3-(5-fluoro-1-methyl-1,2-dihydro-1'H-spiro[indole-3,4'-piperidin]-1'-yl)propanoate A solution of 5-fluoro-1-methyl-1,2-dihydrospiro[indole-3,4'-piperidine] (step 3, 399 mg, 1.81 mmol) and ethyl 2-benzylacrylate (*Tetrahedron Lett.* 1997, 19, 3753-3756, 376 mg, 1.97 mmol) in methanol (19 mL) was stirred at room temperature for 8 days. The reaction mixture was evaporated to give a slight yellow syrup. The residue was purified by column chromatography on silica gel (35 g) eluting with hexane/ethyl acetate (1/1) to afford 421 mg (57%) of the title compound as a colorless syrup:
$^1$H-NMR (CDCl$_3$) δ 7.38-7.17 (5H, m), 6.80-6.72 (2H, m), 6.37-6.32 (1H, m), 4.16-4.04 (2H, m), 3.15 (2H, s), 2.97-2.73 (6H, m), 2.71 (3H, s), 2.47-2.41 (1H, m), 2.20-2.03 (2H, m), 1.86-1.75 (2H, m), 1.68-1.64 (2H, m), 1.15 (3H, t, J=7.2 Hz); MS (ESI) 411 (M+H)$^+$.

Step 5. 2-Benzyl-3-(5-fluoro-1-methyl-1,2-dihydro-1'H-spiro[indole-3,4'-piperidin]-1'-yl)propanoic acid A mixture of ethyl 2-benzyl-3-(5-fluoro-1-methyl-1,2-dihydro-1'H-spiro[indole-3,4'-piperidin]-1'-yl)propanoate (step 4, 421 mg, 1.03 mmol) and lithium hydroxide (131 mg, 16.4 mmol) in tetrahydrofuran/methanol/water (6 mL/2 mL/2 mL) was stirred at room temperature for 22 h. The mixture was poured into tetraborate buffer (pH=9.18, 40 mL) and extracted with 1-butanol/toluene (3/1, 40 mL). The organic layer was dried over sodium sulfate, and evaporated. The residue was was purified by column chromatography on silica gel (35 g) eluting with dichloromethane/methanol (50/1) to afford 282 mg (72%) of the title compound as a colorless solid:
$^1$H-NMR (CDCl$_3$) δ 7.33-7.20 (5H, m), 6.83-6.76 (1H, m), 6.71-6.67 (1H, m), 6.38-6.34 (1H, m), 3.38-3.31 (2H, m), 3.13 (2H, s), 3.01-2.84 (5H, m), 2.69 (3H, s), 2.71-2.45 (5H, m), 2.09-1.98 (2H, m), 1.82-1.75 (2H, m); MS (ESI) 383 (M+H)$^+$, 381 (M−H)$^−$.

Example 5

2-(2-Chlorobenzyl)-3-(1'H,3H-spiro[2-benzofuran-1,4'-piperidin]-1'-yl)propanoic acid trifluoroacetate

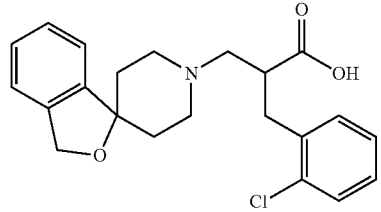

Step 1. tert-Butyl 2-(2-chlorobenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and 1-(bromomethyl)-2-chlorobenzene:
$^1$H-NMR (CDCl$_3$) δ 7.36-7.10 (8H, m), 5.06 (2H, s), 3.10-2.36 (9H, m), 1.95-1.70 (4H, m), 1.35 (9H, s); MS (ESI) 442 (M+H)$^+$.

Step 2. 2-(2-Chlorobenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(2-chlorobenzyl)-3-(1'H,3H-spiro[2-benzofuran-1,4'-piperidin]-1'-yl)propanoate (step 1):

$^1$H-NMR (CDCl$_3$) δ 7.41-7.11 (8H, m), 5.06 (2H, s), 3.75-2.93 (9H, m), 2.58-2.23 (2H, m), 1.97-1.79 (2H, m); MS (ESI) 386 (M+H)$^+$.

Example 6

2-Benzyl-3-(5-fluoro-1-methyl-2-oxo-1,2-dihydro-1'H-spiro[indole-3,4'-piperidin]-1'-yl)propanoic acid

Step 1. tert-Butyl 5-fluoro-2-oxo-1,2-dihydro-1'H-spiro[indole-3,4'-piperidine]-1'-carboxylate To a stirred solution of 5-fluoro-1,3-dihydro-2H-indol-2-one (1.80 g, 11.9 mmol) in tetrahydrofuran (30 mL) was added dropwise a 1 M solution of sodium bis(trimethylsilyl)amide in tetrahydrofuran (35.7 mL, 35.7 mmol) at −78° C. for 15 min and the mixture was stirred for 1.5 h at the same temperature. To the mixture was added dropwise a solution of tert-butyl bis(2-chloroethyl)carbamate (2.88 g, 11.9 mmol) in tetrahydrofuran (10 mL) at −78° C., then this resulting mixture was slowly warmed up to room temperature and stirred for 19 h at the same temperature. The reaction mixture was quenched by the addition of ammonium chloride aqueous solution, and concentrated to give a brown residue. The crude material was partitioned between ethyl acetate and water, and then the organic layer was washed with brine, dried over sodium sulfate, and evaporated. The residue was purified by column chromatography on silica gel (100 g) eluting with hexane/acetone (3/1) to afford 356 mg (15%) of the title compound as a slight brown syrup:

$^1$H-NMR (CDCl$_3$) δ 8.56 (1H, br.s), 7.03-6.83 (3H, m), 3.89-3.69 (4H, m), 1.92-1.72 (4H, m), 1.50 (9H, s); MS (ESI) 319 (M−H)$^-$.

Step 2. tert-Butyl 5-fluoro-1-methyl-2-oxo-1,2-dihydro-1'H-spiro[indole-3,4'-piperidine]-1'-carboxylate To a stirred solution of tert-butyl 5-fluoro-2-oxo-1,2-dihydro-1'H-spiro[indole-3,4'-piperidine]-1'-carboxylate (step 1, 166 mg, 0.518 mmol) in N,N-dimethylformamide (4 mL) was added 70% sodium hydride in mineral oil (27 mg, 0.777 mmol) at 0° C. and the mixture was stirred for 10 min at the same temperature. To the mixture was added methyl iodide (147 mg, 1.04 mmol) at 0° C., then this resulting mixture was slowly warmed up to room temperature and stirred for 18 h at the same temperature. The reaction mixture was diluted with toluene/ethyl acetate (1/3), then washed with water for two times, and then the organic layer was washed with brine, dried over sodium sulfate, and evaporated to afford 130 mg (75%) of the title compound as a slight yellow solid:

$^1$H-NMR (CDCl$_3$) δ 7.05-6.96 (2H, m), 6.79-6.75 (1H, m), 3.90-3.73 (4H, m), 3.19 (3H, s), 1.87-1.68 (4H, m), 1.50 (9H, s).

Step 3. 5-Fluoro-1-methylspiro[indole-3,4'-piperidin]-2(1H)-one

A solution of tert-butyl 5-fluoro-1-methyl-2-oxo-1,2-dihydro-1'H-spiro[indole-3,4'-piperidine]-1'-carboxylate (step 2, 130 mg, 0.389 mmol) in 10% hydrochloric acid methanol solution (5 mL) was stirred for 4 days. The reaction mixture was evaporated to give a yellow syrup. This crude material was partitioned between diethyl ether and 0.4 N sodium hydroxide aqueous solution, and then the organic layer was dried over sodium sulfate, and evaporated to afford 70 mg (77%) of the title compound as a colorless solid:

MS (ESI) 235 (M+H)$^+$.

Step 4. Ethyl 2-benzyl-3-(5-fluoro-1-methyl-2-oxo-1,2-dihydro-1'H-spiro[indole-3,4'-piperidin]-1'-yl)propanoate The title compound was prepared according to the procedure described in step 4 of example 4 from 5-fluoro-1-methylspiro[indole-3,4'-piperidin]-2(1H)-one (step 3) and ethyl 2-benzylacrylate (*Tetrahedron Lett.* 1997, 19, 3753-3756.):

$^1$H-NMR (CDCl$_3$) δ 7.31-7.11 (6H, m), 7.00-6.93 (1H, m), 6.76-6.71 (1H, m), 4.16-4.06 (2H, m), 3.17 (3H, s), 3.01-2.80 (6H, m), 2.74-2.65 (1H, m), 2.61-2.55 (2H, m), 1.98-1.88 (2H, m), 1.76-1.66 (2H, m), 1.17 (3H, t, J=7.3 Hz); MS (ESI) 425 (M+H)$^+$.

Step 5. 2-Benzyl-3-(5-fluoro-1-methyl-2-oxo-1,2-dihydro-1'H-spiro[indole-3,4'-piperidin]-1'-yl)propanoic acid The title compound was prepared according to the procedure described in step 5 of example 4 from ethyl 2-benzyl-3-(5-fluoro-1-methyl-2-oxo-1,2-dihydro-1'H-spiro[indole-3,4'-piperidin]-1'-yl)propanoate (step 4):

MS (ESI) 397 (M+H)$^+$, 395 (M−H)$^-$.

Example 7

2-(2-Fluorobenzyl)-3-(1'H,3H-spiro[2-benzofuran-1,4'-piperidin]-1'-yl)propanoic acid trifluoroacetate

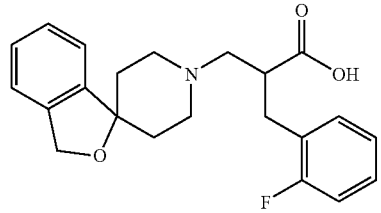

Step 1. tert-Butyl 2-(2-fluorobenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and 1-(bromomethyl)-2-fluorobenzene:

$^1$H-NMR (CDCl$_3$) δ 7.30-6.97 (8H, m), 5.06 (2H, s), 3.02-2.69 (6H, m), 2.53-2.33 (3H, m), 1.97-1.84 (2H, m), 1.80-1.66 (2H, m), 1.35 (9H, s); MS (ESI) 426 (M+H)$^+$.

Step 2. 2-(2-Fluorobenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(2-fluorobenzyl)-3-(1'H,3H-spiro[2-benzofuran-1,4'-piperidin]-1'-yl)propanoate (step 1):
$^1$H-NMR (CDCl$_3$) δ 7.88-7.02 (8H, m), 5.06 (2H, s), 3.86-2.89 (9H, m), 2.54-2.36 (2H, m), 1.96-1.81 (2H, m); MS (ESI) 370 (M+H)$^+$, 368 (M−H)$^−$.

Example 8

2-(2-Methylbenzyl)-3-(1'H,3H-spiro[2-benzofuran-1,4'-piperidin]-1'-yl)propanoic acid trifluoroacetate Step 1. tert-Butyl 2-(2-methylbenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro [2-benzofuran-1,4'-piperidin]-1'-yl)propanoate (WO 2003064425) and 1-(bromomethyl)-2-methylbenzene:
$^1$H-NMR (CDCl$_3$) δ 7.29-7.08 (8H, m), 5.05 (2H, s), 3.92-2.37 (9H, m), 2.33 (3H, s), 1.97-1.84 (2H, m), 1.80-1.68 (2H, m), 1.35 (9H, s); MS (ESI) 422 (M+H)$^+$.

Step 2. 2-(2-Methylbenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(2-methylbenzyl)-3-(1'H,3H-spiro[2-benzofuran-1,4'-piperidin]-1'-yl)propanoate (step 1):
$^1$H-NMR (CDCl$_3$) δ 7.38-6.92 (8H, m), 5.07 (2H, s), 3.84-2.16 (1H, m), 2.38 (3H, s), 1.93-1.85 (2H, m); MS (ESI) 366 (M+H)$^+$, 364 (M−H)$^−$.

Example 9

2-(5-{[tert-Butyl(dimethyl)silyl]oxy}-2-fluorobenzyl)-3-(1'H,3H-spiro[2-benzofuran-1,4'-piperidin]-1'-yl)propanoic acid trifluoroacetate

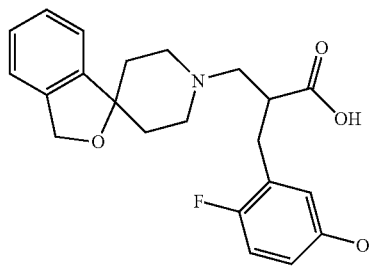

Step 1. tert-Butyl(4-fluoro-3-methylphenoxy)dimethylsilane

To a stirred solution of 4-fluoro-3-methylphenol (15 g, 0.12 mol) and imidazole (18 g, 0.26 mol) in N,N-dimethylformamide (100 mL) was added tert-butyl(chloro)dimethylsilane (20 g, 0.13 mol) at 0° C. The reaction mixture was stirred at room temperature for 20 h, and quenched by the addition of water. The aqueous layer was extracted with diethyl ether (400 mL). The combined organic layers were washed with water and brine, dried over magnesium sulfate, and evaporated to afford 30 g (quant.) of the title compound as a yellow oil:
$^1$H-NMR (CDCl$_3$) δ 6.84 (1H, t, J=8.7 Hz), 6.66-6.54 (2H, m), 2.21 (3H, H, d, J=2.1 Hz), 0.97 (9H, s), 0.17 (6H, s).

Step 2. [3-(Bromomethyl)-4-fluorophenoxy](tert-butyl)dimethylsilane

A mixture of tert-butyl(4-fluoro-3-methylphenoxy)dimethylsilane (step 1, 30 g, 0.12 mol), N-bromosuccinimide (24 g, 0.13 mol) and benzoylperoxide (1.5 g, 6.2 mmol) in carbon tetrachloride (75 mL) was reflux under nitrogen atmosphere for 4 h. The reaction mixture was cooled at 0° C., and the white precipitate was filtered. The filtrate was washed with sodium bicarbonate aqueous solution, dried over magnesium sulfate, and evaporated. The residue was purified by column chromatography on silica gel eluting with hexane to afford 25 g (65%) of the title compound as a colorless oil:
$^1$H-NMR (CDCl$_3$) δ 6.91 (1H, t, J=9.2 Hz), 6.84 (1H, dd, J=6.2, 2.9 Hz), 6.77-6.68 (1H, m), 4.44 (2H, s), 0.97 (9H, s), 0.18 (6H, s).

Step 3. tert-Butyl 2-(5-{[tert-butyl(dimethyl)silyl]oxy}-2-fluorobenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and [3-(bromomethyl)-4-fluorophenoxy](tert-butyl)dimethylsilane (step 2):
$^1$H-NMR (CDCl$_3$) δ 7.28-7.08 (4H, m), 6.85 (1H, t, J=9.2 Hz), 6.69-6.58 (2H, m), 5.06 (2H, s), 2.92-2.66 (6H, m), 2.53-2.33 (3H, m), 1.98-1.84 (2H, m), 1.77-1.68 (2H, m), 1.38 (9H, s), 0.97 (9H, s), 0.17 (6H, s); MS (ESI) 556 (M+H)$^+$.

Step 4. 2-(5-{[tert-Butyl(dimethyl)silyl]oxy}-2-fluorobenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(5-{[tert-butyl(dimethyl)silyl]oxy}-2-fluorobenzyl)-3-(1'H,3H-spiro[2-benzofuran-1,4'-piperidin]-1'-yl)propanoate (step 3):
$^1$H-NMR (CDCl$_3$) δ 7.34-6.66 (7H, m), 5.06 (2H, s), 3.78-2.32 (1H, m), 1.91-1.31 (2H, m), 0.97 (9H, s), 0.17 (6H, s); MS (ESI) 500 (M+H)$^+$, 498 (M−H)$^−$.

Example 10

2-Benzyl-3-(1-methyl-2-oxo-1,2-dihydro-1'H-spiro[indole-3,4'-piperidin]-1'-yl)propanoic acid

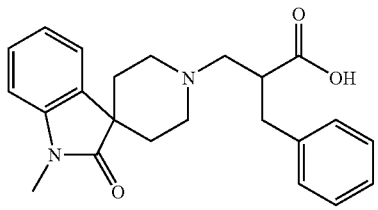

Step 1. tert-Butyl 2-oxo-1,2-dihydro-1'H-spiro[indole-3,4'-piperidine]-1'-carboxylate The title compound was prepared according to the procedure described in step 1 of example 6 from 1,3-dihydro-2H-indol-2-one:
$^1$H-NMR (CDCl$_3$) δ 7.92 (1H, br.s), 7.29-7.21 (2H, m), 7.07-7.02 (1H, m), 6.92-6.89 (1H, m), 3.90-3.75 (4H, m), 1.92-1.71 (4H, m), 1.50 (9H, s); MS (ESI) 301 (M−H)$^-$.

Step 2. tert-Butyl 1-methyl-2-oxo-1,2-dihydro-1'H-spiro[indole-3,4'-piperidine]-1'-carboxylate The title compound was prepared according to the procedure described in step 2 of example 6 from tert-butyl 2-oxo-1,2-dihydro-1'H-spiro[indole-3,4'-piperidine]-1'-carboxylate (step 1):
$^1$H-NMR (CDCl$_3$) δ 7.32-7.26 (2H, m), 7.09-7.04 (1H, m), 6.87-6.85 (1H, m), 3.91-3.74 (4H, m), 3.21 (3H, s), 1.87-1.71 (4H, m), 1.50 (9H, s).

Step 3. 1-Methylspiro[indole-3,4'-piperidin]-2(1H)-one

The title compound was prepared according to the procedure described in step 3 of example 6 from tert-butyl 1-methyl-2-oxo-1,2-dihydro-1'H-spiro[indole-3,4'-piperidine]-1'-carboxylate (step 2):
$^1$H-NMR (CDCl$_3$) δ 7.45-7.42 (1H, m), 7.32-7.25 (1H, m), 7.10-7.05 (1H, m), 6.87-6.84 (1H, m), 3.43-3.34 (2H, m), 3.12-3.03 (2H, m), 1.90-1.81 (2H, m), 1.76-1.68 (2H, m); MS (ESI) 217 (M+H)$^+$.

Step 4. Ethyl 2-benzyl-3-(1-methyl-2-oxo-1,2-dihydro-1'H-spiro[indole-3,4'-piperidin]-1'-yl)propanoate The title compound was prepared according to the procedure described in step 4 of example 4 from 1-methylspiro[indole-3,4'-piperidin]-2(1H)-one (step 3) and ethyl 2-benzylacrylate (*Tetrahedron Lett.* 1997, 19, 3753-3756.):
$^1$H-NMR (CDCl$_3$) δ 7.39 (1H, br.d, J=7.0 Hz), 7.30-7.18 (6H, m), 7.07-7.01 (1H, m), 6.84 (1H, br.d, J=7.7 Hz), 4.14-4.06 (2H, m), 3.19 (3H, s), 3.02-2.81 (6H, m), 2.77-2.69 (1H, m), 2.66-2.56 (2H, m), 1.98-1.90 (2H, m), 1.77-1.70 (2H, m), 1.17 (3H, t, J=7.0 Hz); MS (ESI) 407 (M+H)$^+$.

Step 5. 2-Benzyl-3-(1-methyl-2-oxo-1,2-dihydro-1'H-spiro[indole-3,4'-piperidin]-1'-yl)propanoic acid The title compound was prepared according to the procedure described in step 5 of example 4 from ethyl 2-benzyl-3-(1-methyl-2-oxo-1,2-dihydro-1'H-spiro[indole-3,4'-piperidin]-1'-yl)propanoate (step 4):
MS (ESI) 379 (M+H)$^+$, 377 (M−H)$^-$.

Example 11

2-(5-{[tert-Butyl(dimethyl)silyl]oxy}-2-chlorobenzyl)-3-(1'H,3H-spiro[2-benzofuran-1,4'-piperidin]-1'-yl)propanoic acid trifluoroacetate

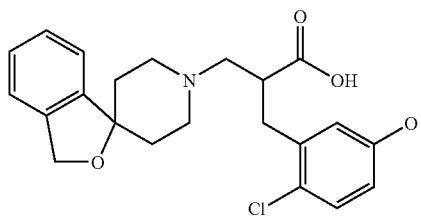

Step 1. tert-Butyl 2-(5-{[tert-butyl(dimethyl)silyl]oxy}-2-chlorobenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and [3-(bromomethyl)-4-chlorophenoxy](tert-butyl)dimethylsilane (*J. Org. Chem.* 1996, 61, 6974.):
$^1$H-NMR (CDCl$_3$) δ 7.28-7.09 (5H, m), 6.74 (1H, d, J=3.0 Hz), 6.62 (1H, dd, J=8.7, 3.0 Hz), 5.06 (2H, s), 3.49-2.69 (6H, m), 2.52-2.38 (3H, m), 1.93-1.70 (4H, m), 1.39 (9H, s), 0.96 (9H, s), 0.18 (6H, s); MS (ESI) 572 (M+H)$^+$.

Step 2. 2-(5-{[tert-Butyl(dimethyl)silyl]oxy}-2-chlorobenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(5-{[tert-butyl(dimethyl)silyl]oxy}-2-chlorobenzyl)-3-(1'H,3H-spiro[2-benzofuran-1,4'-piperidin]-1'-yl)propanoate (step 1):
$^1$H-NMR (CDCl$_3$) δ 7.85-7.01 (5H, m), 6.78-6.65 (2H, m), 5.06 (2H, s), 3.79-2.71 (9H, m), 2.61-2.28 (2H, m), 1.92-1.72 (2H, m), 0.96 (9H, s), 0.18 (6H, s); MS (ESI) 516 (M+H)$^+$.

Example 12

2-(2,6-Difluorobenzyl)-3-(1'H,3H-spiro[2-benzofuran-1,4'-piperidin]-1'-yl)propanoic acid trifluoroacetate

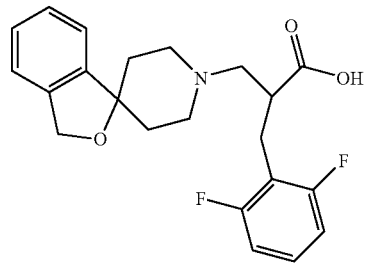

Step 1. tert-Butyl 2-(2,6-difluorobenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and 2-(bromomethyl)-1,3-difluorobenzene:
$^1$H-NMR (CDCl$_3$) δ 7.30-7.05 (5H, m), 6.90-6.80 (2H, m), 5.05 (2H, s), 2.96-2.70 (6H, m), 2.56-2.34 (3H, m), 1.96-1.68 (4H, m), 1.37 (9H, s); MS (ESI) 444 (M+H)$^+$.

Step 2. 2-(2,6-Difluorobenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(2,6-difluorobenzyl)-3-(1'H,3H-spiro[2-benzofuran-1,4'-piperidin]-1'-yl)propanoate (step 1):

¹H-NMR (CDCl₃) δ 7.45-6.86 (7H, m), 5.06 (2H, s), 3.76-2.90 (9H, m), 2.49-2.31 (2H, m), 1.98-1.81 (2H, m); MS (ESI) 388 (M+H)⁺, 386 (M−H)⁻.

Example 13

2-(4-{[tert-Butyl(dimethyl)silyl]oxy}-2-chlorobenzyl)-3-(1'H,3H-spiro[2-benzofuran-1,4'-piperidin]-1'-yl)propanoic acid trifluoroacetate

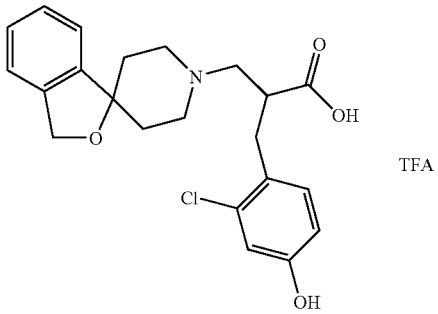

TFA

Step 1. (4-{[tert-Butyl(dimethyl)silyl]oxy}-2-chlorophenyl)methanol

To a stirred solution of 4-{[tert-butyl(dimethyl)silyl]oxy}-2-chlorobenzaldehyde (WO 2003051797, 1.58 g, 5.83 mmol) in methanol (5 mL) was added sodium borohydride (264 mg, 7.00 mmol) at 0° C. The mixture was stirred at room temperature for 3 h, and quenched by addition of aqueous ammonium chloride. The mixture was extracted with ethyl acetate (200 mL), and the organic layer was washed with brine, dried over sodium sulfate, and evapolated. The residue was purified by column chromatography on silica gel (100 g) eluting with hexane/ethyl acetate (20/1 to 10/1) to afford 1.51 g (95%) of the title compound as a colorless oil:
¹H-NMR (CDCl₃) δ 7.30 (1H, d, J=8.5 Hz), 6.87(1H, d, J=2.4 Hz), 6.74 (1H, dd, J=8.5, 2.4 Hz), 4.70 (2H, br.s), 0.98 (9H, s), 0.20 (6H, s); MS (ESI) 255 (M+H)⁺.

Step 2. tert-Butyl[3-chloro-4-(chloromethyl)phenoxy]dimethylsilane

To a stirred solution of tert-butyl[3-chloro-4-(chloromethyl)phenoxy]dimethylsilane (step 1, 500 mg, 1.83 mmol) in dichloromethane (5 mL) were added triethylamine (0.139 mL, 2.75 mmol) and methane sulfonylchloride (231 mg, 2.02 mmol) at room temperature. The mixture was stirred for 2 h at the same temperature. The mixture was diluted with ethyl acetate (100 mL), and the mixture was washed with water and brine, dried over sodium sulfate and evapolated. The residue was purified by silica gel (40 g) eluting with hexane/ethyl acetate (10/1) to afford 580 mg (quant.) of the title compound as a colorless oil:
¹H-NMR (CDCl₃) δ 7.87-7.26 (1H, m), 6.93-6.71 (2H, m), 4.66 (2H, s), 0.97 (9H, s), 0.21 (6H, s).

Step 3. tert-Butyl 2-(4-{[tert-butyl(dimethyl)silyl]oxy}-2-chlorobenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and tert-butyl[3-chloro-4-(chloromethyl)phenoxy]dimethylsilane (step 2):

¹H-NMR (CDCl₃) δ 7.38-6.61 (7H, m), 5.06 (2H, s), 3.00-2.33 (9H, m), 2.04-1.65 (4H, m), 1.86 (9H, s), 0.97 (9H, s), 0.18 (6H, s); MS (ESI) 572 (M+H)⁺.

Step 4. 2-(4-{[tert-Butyl(dimethyl)silyl]oxy}-2-chlorobenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(4-{[tert-butyl(dimethyl)silyl]oxy}-2-chlorobenzyl)-3-(1'H,3H-spiro[2-benzofuran-1,4'-piperidin]-1'-yl)propanoate (step 3):
¹H-NMR (CDCl₃) δ 7.83-6.69 (7H, m), 5.06 (2H, s), 3.78-2.78 (9H, m), 2.54-2.31 (2H, m), 2.00-1.80 (2H, m), 0.97 (9H, s), 0.20 (6H, s); MS (ESI) 516 (M+H)⁺, 514 (M−H)⁻.

Example 14

2-(2,6-Difluoro-3-hydroxybenzyl)-3-(1'H,3H-spiro[2-benzofuran-1,4'-piperidin]-1'-yl)propanoic acid trifluoroacetate

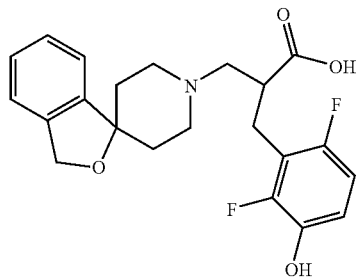

TFA

Step 1. 2,4-Difluoro-3-(hydroxymethyl)phenol

To a stirred solution of tert-butyl(2,4-difluorophenoxy)dimethylsilane (J. Med. Chem. 1993, 36, 3947., 1.50 g, 6.14 mmol) in tetrahydrofuran (30 mL) was added a 1.57 M solution of n-butyllithium in hexane (4.69 mL, 7.37 mmol) at −78° C. over 10 minutes, and the mixture was stirred at −78° C. for 2 h. To the mixture, N,N-dimethylformamide (0.950 mL, 2.28 mmol) was added at −78° C. The mixture was stirred at −78° C. for 1 h, allowed to warm to room temperature and stand at room temperature for 16 h. The mixture was diluted with methanol (20 mL), and to the mixture was added sodium borohydride (696 mg, 18.4 mmol) at 0° C. The mixture was stirred at room temperature for 1.5 h. The reaction was quenched by addition of aqueous ammonium chloride at 0° C. to be pH=7. The mixture was extracted with diethyl ether (200 mL) and the organic layer was washed with brine, dried over magnesium sulfate and evapolated. The residue was purified by column chromatography on silica gel (100 g) eluting with hexane/ethyl acetate (2/1) to afford 410 mg (42%) of the title as a colorless oil:
¹H-NMR (CDCl₃) δ 6.93 (1H, td, J=9.2, 5.3 Hz), 6.81(1H, td, J=9.2, 1.8 Hz), 4.80 (2H, s), 0.98 (9H, s), 0.20 (6H, s); MS (EI) 160 (M)⁺.

Step 2. 3-(Bromomethyl)-2,4-difluorophenol

To a stirred solution of 2,4-difluoro-3-(hydroxymethyl)phenol (step 1, 410 mg, 256 mmol) in diethyl ether (4 mL)

and dichloromethne (1 mL) was added phosphorus tribromide (0.257 mL, 2.71 mmol) at 0° C. The mixture was stirred for 30 min, and then the mixture was poured onto ice-aqueous sodium bicarbonate. The mixture was extracted with ethyl acetate (200 mL), and the organic layer was washed with water and brine, dried over magnesium sulfate and evapolated to afford 266 mg (47%) of the title compound as a colorless oil, which was used in the next step without purification:

$^1$H-NMR (CDCl$_3$) δ 6.95 (1H, td, J=9.0, 5.4 Hz), 6.81 (1H, td, J=9.0, 1.8 Hz), 4.52 (2H, s).

Step 3. tert-Butyl 2-(2,6-difluoro-3-hydroxybenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate and 3-(bromomethyl)-2,4-difluorophenol (step 2):

$^1$H-NMR (CDCl$_3$) δ 7.30-7.18 (3H, m), 7.12-7.06 (1H, m), 6.82 (1H, td, J=9.1, 5.3 Hz), 6.73 (1H, td, J=9.1, 1.5 Hz), 5.05 (2H, m), 2.96-2.38 (9H, m), 1.97-1.69 (4H, m), 1.87 (9H, s); MS (ESI) 460 (M+H)$^+$, 458 (M−H)$^-$.

Step 4. 2-(2,6-Difluoro-3-hydroxybenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(2,6-difluoro-3-hydroxybenzyl)-3-(1'H,3H-spiro[2-benzofuran-1,4'-piperidin]-1'-yl)propanoate (step 3):

$^1$H-NMR (CDCl$_3$) δ 7.84-7.10 (4H, m), 6.93-6.84 (1H, m), 6.78-6.70 (1H, m), 5.06 (2H, s), 3.71-3.58 (3H, m), 3.39-2.89 (6H, m), 2.47-2.29 (2H, m), 1.94-1.83 (2H, m); MS (ESI) 404 (M+H)$^+$.

Example 15

2-(2-Chloro-5-hydroxybenzyl)-3-(1'H,3H-spiro[2-benzofuran-1,4'-piperidin]-1'-yl)propanoic acid

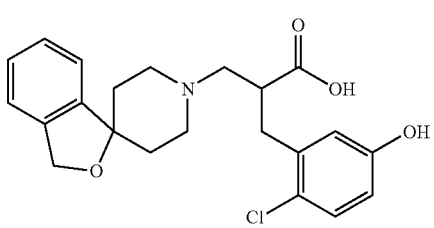

Step 1. tert-Butyl 2-(2-chloro-5-hydroxybenzyl)-3-(1'H,3H-spiro[2-benzofuran-1,4'-piperidin]-1'-yl)propanoate To a solution of tert-butyl 2-(5-{[tert-butyl(dimethyl)silyl]oxy}-2-chlorobenzyl)-3-(1'H,3H-spiro[2-benzofuran-1,4'-piperidin]-1'-yl)propanoate (step 1 of example 11, 2.5 g, 4.3 mmol) in tetrahydrofuran was added a solution of tetrabutylammonium fluoride (1.0 M in tetrahydrofuran, 4.3 mL, 4.3 mmol) and the mixture was stirred at room temperature for 3 h. Water (50 mL) was added to the mixture and the mixture was extracted with ethyl acetate (50 mL×3). The combined organic layers were washed with brine (50 mL), dried over magnesium sulfate and evaporated. The residue was purified by column chromatography on silica gel eluting with hexane/ethyl acetate (3/1) to afford 1.8 g (94%) of the title compound as a white powder:

$^1$H-NMR (CDCl$_3$) δ 7.32-7.04 (5H, m), 6.76 (1H, d, J=3.0 Hz,), 6.63 (1H, dd, J=8.6, 3.0 Hz), 5.06 (2H, s), 3.08-2.71 (6H, m), 2.60-2.37 (3H, m), 2.02-1.84 (2H, m), 1.80-1.67 (2H, m), 1.38 (9H, s).

Step 2. 2-(2-Chloro-5-hydroxybenzyl)-3-(1'H,3H-spiro[2-benzofuran-1,4'-piperidin]-1'-yl)propanoic acid To a solution of tert-butyl 2-(2-chloro-5-hydroxybenzyl)-3-(1'H,3H-spiro[2-benzofuran-1,4'-piperidin]-1'-yl)propanoate (step 1, 1.8 g, 4.0 mmol) in dichloromethane was added trifluoroacetic acid (4.0 mL) and the mixture was stirred at room temperature for 4 h. The volatile materials were removed to give a residue, which was dissolved into dichloromethane. An amine coated silica gel (30-50 μm, 20 g) was added to the solution and the resulting suspension was filtered. The amine coated silica gel was washed with dichloromethane/methanol (10/1). The combined organic layers were concentrated to give a white powder. The powder was washed with isopropyl alcohol to afford 0.92 g (57%) of the title compound:

$^1$H-NMR (DMSO-d$_6$) δ 9.50 (1H, br.s), 7.23-6.98 (5H, m), 6.66-6.48 (2H, m), 4.84 (2H, s), 2.86-2.53 (6H, m), 2.46-2.12 (3H, m), 1.84-1.63 (2H, m), 1.59-1.43 (2H, m).

Example 16

2-[2-(Methoxymethyl)benzyl]-3-(1'H,3H-spiro[2-benzofuran-1,4'-piperidin]-1'-yl)propanoic acid trifluoroacetate

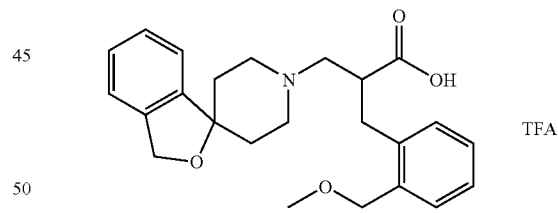

Step 1. tert-Butyl 2-[2-(methoxymethyl)benzyl]-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and 1-(bromomethyl)-2-(methoxymethyl)benzene (WO 2003106443):

$^1$H-NMR (CDCl$_3$) δ 7.35-7.07 (8H, m), 5.06 (2H, s), 4.56 (1H, d, J=11.5 Hz), 4.45 (1H, d, J=11.5 Hz), 3.41 (3H, s), 2.96-2.71 (6H, m), 2.54-2.33 (3H, m), 1.98-1.68 (4H, m), 1.35 (9H, s); MS (ESI) 452 (M+H)$^+$.

Step 2. 2-[2-(Methoxymethyl)benzyl]-3-(1'H,3H-spiro[2-benzofuran-1,4'-piperidin]-1'-yl)propanoic acid trifluoroacetate The title compound was prepared according to the procedure described in step 3 of example 1 from tert-butyl 2-[2-(methoxymethyl)benzyl]-3-(1'H,3H-spiro[2-benzofuran-1,4'-piperidin]-1'-yl)propanoate (step 1):

$^1$H-NMR (CDCl$_3$) δ 7.39-7.06 (8H, m), 5.04 (2H, s), 4.51 (1H, d, J=10.9 Hz), 4.46 (1H, d, J=10.9 Hz), 3.71-2.75 (9H, m), 3.45 (3H, s), 2.47-2.27 (2H, m), 1.92-1.77 (2H, m); MS (ESI) 396 (M+H)$^+$, 394 (M−H)$^−$.

Example 17

2-(2-Chlorobenzyl)-3-(1-methyl-2-oxo-1,2-dihydro-1'H-spiro[indole-3,4'-piperidin]-1'-yl)propanoic acid

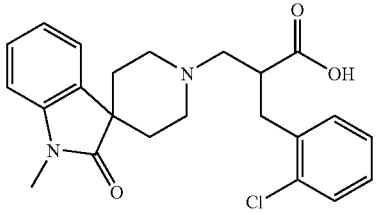

Step 1. Ethyl 3-(2-chlorophenyl)-2-(diethoxyphosphoryl)propanoate

To a stirred solution of ethyl (diethoxyphosphoryl)acetate (10.0 g, 44.6 mmol) in N,N-dimethylformamide (100 mL) was added 60% sodium hydride in mineral oil (1.96 g, 49.1 mmol) at 0° C. and the mixture was stirred for 1 h at the same temperature. To the mixture was added 1-(bromomethyl)-2-chlorobenzene (6.35 mL, 49.1 mmol) at 0° C. and the resulting mixture was stirred for 18 h at the room temperature. The reaction mixture was quenched by the addition of water, then extracted with diethyl ether (200 mL×2), and the combined organic layers were washed with water (100 mL) and brine (100 mL), dried over sodium sulfate, and evaporated. The residue was purified by column chromatography on silica gel (500 g) eluting with hexane/ethyl acetate (1/1) to afford 14.6 g (93%) of the title compound as a colorless oil:

$^1$H-NMR (CDCl$_3$) δ 7.36-7.09 (4H, m), 4.26-4.06 (6H, m), 3.52-3.27 (3H, m), 1.39-1.33 (6H, m), 1.15 (3H, t, J=7.0 Hz).

Step 2. Ethyl 2-(2-chlorobenzyl)acrylate

To a stirred mixture of ethyl 3-(2-chlorophenyl)-2-(diethoxyphosphoryl)propanoate (step 1, 14.6 g, 41.9 mmol) and 37% formaldehyde in water (20 mL) was added a solution of potassium carbonate (17.4 g) in water (80 mL) at the room temperature and the mixture was stirred for 6 h at 90° C. After cooling to room temperature, the mixture was extracted with diethyl ether (300 mL), and then the organic layer was washed with brine (100 mL), dried over magnesium sulfate, and evaporated. The residue was purified by column chromatography on silica gel (300 g) eluting with hexane/ethyl acetate (30/1) to afford 6.57 g (70%) of the title compound as a colorless oil:

$^1$H-NMR (CDCl$_3$) δ 7.39-7.36 (1H, m), 7.25-7.16 (3H, m), 6.27 (1H, q, J=1.3 Hz), 5.33 (1H, q, J=1.7 Hz), 4.22 (2H, q, J=7.2 Hz), 3.76 (2H, t, J=1.4 Hz), 1.29 (3H, t, J=6.0 Hz).

Step 3. Ethyl 2-(2-chlorobenzyl)-3-(1-methyl-2-oxo-1,2-dihydro-1'H-spiro[indole-3,4'-piperidin]-1'-yl)propanoate The title compound was prepared according to the procedure described in step 4 of example 4 from 1-methylspiro[indole-3,4'-piperidin]-2(1H)-one (step 3 of example 10) and ethyl 2-(2-chlorobenzyl)acrylate (step 2):

$^1$H-NMR (CDCl$_3$) δ 7.41-7.02 (7H, m), 6.85-6.80 (1H, m), 4.14-4.02 (2H, m), 3.19-2.59 (12H, m), 1.98-1.68 (4H, m), 1.18-1.12 (3H, m); MS (ESI) 441 (M+H)$^+$.

Step 4. 2-(2-Chlorobenzyl)-3-(1-methyl-2-oxo-1,2-dihydro-1'H-spiro[indole-3,4'-piperidin]-1'-yl)propanoic acid The title compound was prepared according to the procedure described in step 5 of example 4 from ethyl 2-(2-chlorobenzyl)-3-(1-methyl-2-oxo-1,2-dihydro-1'H-spiro[indole-3,4'-piperidin]-1'-yl)propanoate (step 3):

MS (ESI) 413 (M+H)$^+$, 411 (M−H)$^−$.

Example 18

2-(2-Chlorobenzyl)-3-(5-fluoro-1-methyl-1,2-dihydro-1'H-spiro[indole-3,4'-piperidin]-1'-yl)propanoic acid

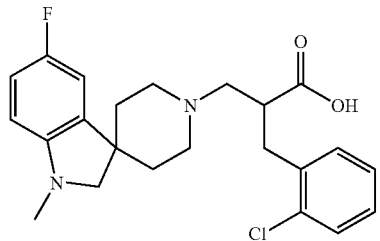

Step 1. Ethyl 2-(2-chlorobenzyl)-3-(5-fluoro-1-methyl-1,2-dihydro-1'H-spiro[indole-3,4'-piperidin]-1'-yl)propanoate The title compound was prepared according to the procedure described in step 4 of example 4 from ethyl 2-(2-chlorobenzyl)acrylate (step 2 of example 17):

$^1$H-NMR (CDCl$_3$) δ 7.36-7.33 (1H, m), 7.23-7.14 (3H, m), 6.80-6.82 (2H, m), 6.35 (1H, dd, J=8.4, 3.9 Hz), 4.14-4.03 (2H, m), 3.16 (2H, s), 3.13-3.05 (2H, m), 2.95-2.72 (4H, m), 2.71 (3H, s), 2.49 (1H, dd, J=12.3, 5.9 Hz), 2.12-2.06 (2H, m), 1.80 (2H, td, J=12.6, 4.2 Hz), 1.66 (2H, br.d, J=14.1 Hz), 1.15 (3H, t, J=7.1 Hz); MS (ESI) 445 (M+H)$^+$.

Step 2. 2-(2-Chlorobenzyl)-3-(5-fluoro-1-methyl-1,2-dihydro-1'H-spiro[indole-3,4'-piperidin]-1'-yl)propanoic acid The title compound was prepared according to the procedure described step 5 in of example 4 from ethyl 2-(2- chlorobenzyl)-3-(5-fluoro-1-methyl-1,2-dihydro-1'H-spiro [indole-3,4'-piperidin]-1'-yl)propanoate (step 1):
MS (ESI) 417 (M+H)⁺, 415 (M−H)⁻.

Example 19

2-(2-Fluoro-5-hydroxybenzyl)-3-(1-methyl-2-oxo-1, 2-dihydro-1'H-spiro[indole-3,4'-piperidin]-1'-yl) propanoic acid

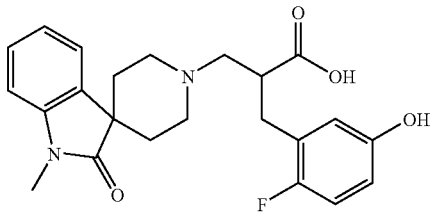

Step 1. Ethyl 3-(5-{[tert-butyl(dimethyl)silyl]oxy}-2-fluorophenyl)-2-(diethoxyphosphoryl)propanoate The title compound was prepared according to the procedure described in step 1 of example 17 from [3-(bromomethyl)-4-fluorophenoxy](tert-butyl)dimethylsilane (step 2 of example 9):
¹H-NMR (CDCl₃) δ 6.86 (1H, t, J=6.9 Hz), 6.68-6.81 (2H, m), 4.24-4.06 (6H, m), 3.37-3.12 (3H, m), 1.38-1.33 (6H, m), 1.18 (3H, t, J=7.2 Hz), 0.96 (9H, s), 0.15 (6H, s).

Step 2. Ethyl 2-(5-{[tert-butyl(dimethyl)silyl]oxy}-2-fluorobenzyl)acrylate The title compound was prepared according to the procedure described in step 2 of example 17 from ethyl 3-(5-{[tert-butyl(dimethyl)silyl]oxy}-2-fluorophenyl)-2-(diethoxyphosphoryl)propanoate (step 1):
¹H-NMR (CDCl₃) δ 6.91-6.85 (1H, m), 6.67-6.62 (2H, m), 6.25 (1H, d, J=1.1 Hz), 5.44-5.42 (1H, m), 4.21 (2H, q, J=7.2 Hz), 3.59 (2H, s), 1.28 (3H, t, J=7.2 Hz), 0.96 (9H, s), 0.16 (6H, s).

Step 3. Ethyl 2-(5-{[tert-butyl(dimethyl)silyl]oxy}-2-fluorobenzyl)-3-(1-methyl-2-oxo-1,2-dihydro-1'H-spiro[indole-3,4'-piperidin]-1'-yl)propanoate The title compound was prepared according to the procedure described in step 4 of example 4 from 1-methylspiro [indole-3,4'-piperidin]-2(1H)-one (step 3 of example 10) and ethyl 2-(5-{[tert-butyl(dimethyl)silyl]oxy}-2-fluorobenzyl)acrylate (step 2):
¹H-NMR (CDCl₃) δ 7.39 (1H, d, J=7.1 Hz), 7.31-7.25 (1H, m), 7.04 (1H, t, J=7.8 Hz), 6.89-6.82 (2H, m), 6.68-6.61 (2H, m), 4.13 (2H, q, J=7.1 Hz), 3.19 (3H, s), 3.03-2.57 (9H, m), 1.98-1.69 (4H, m), 1.21 (3H, t, J=7.4 Hz), 0.97 (9H, s), 0.17 (6H, s); MS (ESI) 555 (M+H)⁺.

Step 4. 2-(2-Fluoro-5-hydroxybenzyl)-3-(1-methyl-2-oxo-1,2-dihydro-1'H-spiro[indole-3,4'-piperidin]-1'-yl)propanoic acid The title compound was prepared according to the procedure described in step 5 of example 4 from ethyl 2-(5-{[tert-butyl(dimethyl)silyl]oxy}-2-fluorobenzyl)-3-(1-methyl-2-oxo-1,2-dihydro-1'H-spiro[indole-3,4'-piperidin]-1'-yl)propanoate (step 3):
MS (ESI) 413 (M+H)⁺, 411 (M−H)⁻.

Example 20

2-(6-Chloro-2-fluoro-3-hydroxybenzyl)-3-(1'H,3H-spiro[2-benzofuran-1,4'-piperidin]-1'-yl)propanoic acid trifluoroacetate

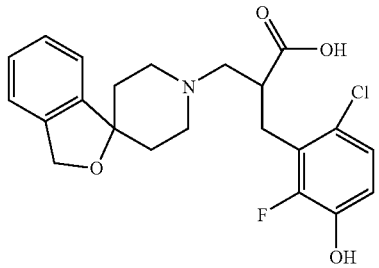

Step 1. tert-Butyl(4-chloro-2-fluorophenoxy)dimethylsilane

The title compound was prepared according to the procedure described in step 1 of example 9 from 4-chloro-2-fluorophenol:
¹H-NMR (CDCl₃) δ 7.08 (1H, dd, J=10.3, 2.4 Hz), 6.97 (1H, ddd, J=8.7, 2.4, 1.5 Hz), 6.83 (1H, t, J=8.7 Hz), 0.99 (9H, s), 0.18 (6H, s).

Step 2. tert-Butyl(4-chloro-2-fluorophenoxy)dimethylsilane

The title compound was prepared according to the procedure described in step 1 of example 14 from tert-butyl(4-chloro-2-fluorophenoxy)dimethylsilane (step 1):
¹H-NMR (CDCl₃) δ 7.05 (1H, dd, J=8.7, 1.8 Hz), 6.82 (1H, d, J=8.7 Hz), 4.83 (2H, dd, J=6.8, 2.3 Hz), 1.00 (9H, s), 0.19 (3H, s), 0.19 (3H, s); MS (EI) 233 (M−ᵗBu)⁺.

Step 3. [3-(Bromomethyl)-4-chloro-2-fluorophenoxy](tert-butyl)dimethylsilane The title compound was prepared according to the procedure described in step 2 of example 14 from tert-butyl(4-chloro-2-fluorophenoxy)dimethylsilane (step 2):
¹H-NMR (CDCl₃) δ 7.06 (1H, dd, J=8.7, 1.6 Hz), 6.83 (1H, t, J=8.7 Hz), 4.61 (2H, d, J=2.0 Hz), 1.00 (9H, s), 0.19 (6H, s).

Step 4. tert-Butyl 2-(6-chloro-2-fluoro-3-hydroxybenzyl)-3-(1'H,3H-spiro[2-benzoran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and [3-(bromomethyl)-4-chloro-2-fluorophenoxy](tert-butyl)dimethylsilane (step 3):
¹H-NMR (CDCl₃) δ 7.29-7.17 (3H, m), 7.11-7.06 (1H, m), 7.02 (1H, dd, J=8.8, 1.8 Hz), 6.80 (1H, t, J=8.8 Hz), 5.05 (2H, s), 3.07-2.73 (6H, m), 2.56-2.37 (3H, m), 1.95-1.65 (4H, m), 1.39 (9H, s); MS (ESI) 476 (M+H)⁺, 474 (M−H)⁻.

Step 5. 2-(6-Chloro-2-fluoro-3-hydroxybenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(6-chloro-2-fluoro-3-hydroxybenzyl)-3-(1'H,3H-spiro[2-benzofuran-1,4'-piperidin]-1'-yl)propanoate (step 4):

$^1$H-NMR (CDCl$_3$) δ 9.63 (1H, br.s), 7.45-6.84 (6H, m), 5.07 (2H, s), 3.79 -2.90 (9H, m), 2.58-1.78 (4H, m); MS (ESI) 420 (M+H)$^+$, 418 (M–H)$^-$.

Example 21

3-(2,3-Dihydro-1'H-spiro[indene-1,4'-piperidin]-1'-yl)-2-(pyridin-2-ylmethyl)propanoic acid trifluoroacetate

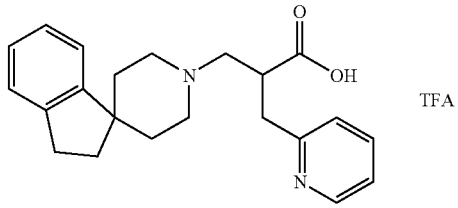

Step 1. tert-Butyl 3-(2,3-dihydro-1'H-spiro[indene-1,4'-piperidin]-1'-yl)-2-( pyridin-2-ylmethyl)propanoate The title compound was prepared according to the procedure described in step 2 of example 1 from tert-butyl 3-(2,3-dihydro-1'H-spiro[indene-1,4'-piperidin]-1'-yl)propanoate (WO 2003064425) and 2-(bromomethyl)pyridine:

$^1$H-NMR (CDCl$_3$) δ 8.58-8.51 (1H, m), 7.64-7.52 (1H, m), 7.29-7.06 (6H, m), 3.20-1.32 (17H, m), 1.38 (9H, m); MS (ESI) 407 (M+H)$^+$.

Step 2. 3-(2,3-Dihydro-1'H-spiro[indene-1,4'-piperidin]-1'-yl)-2-(pyridin-2-yl methyl) propanoic acid trifluoroacetate The title compound was prepared according to the procedure described in step 3 of example 1 from tert-butyl 3-(2,3-dihydro-1'H-spiro[indene-1,4'-piperidin]-1'-yl)-2-(pyridin-2-ylmethyl)propanoate(step 1).

$^1$H-NMR (CDCl$_3$) δ 8.74-7.83 (4H, m), 7.29-7.11 (4H, m), 3.92-2.03 (15H, m), 1.89-1.74 (2H, m); MS (ESI) 351 (M+H)$^+$, 349 (M–H)$^-$.

Example 22

2-(5-{[tert-Butyl(dimethyl)silyl]oxy}-2-methylbenzyl)-3-(1'H,3H-spiro[2-benzofuran-1,4'-piperidin]-1'-yl)propanoic acid trifluoroacetate

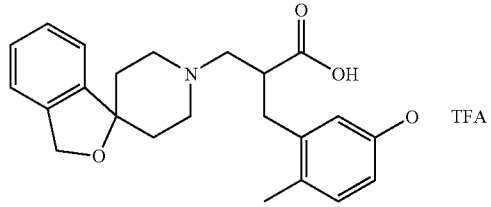

Step 1. Methyl 5-hydroxy-2-methylbenzoate

To a stirred solution of 5-hydroxy-2-methylbenzoic acid (WO 9619437, 1.11 g, 6.69 mmol), in dichloromethane (6 mL) and methanol (6 mL) was added a 2.0 M solution of (trimethylsilyl)diazomethane in diethyl ether (7.31 mL, 14.7 mmol) at 0° C. The mixture was stirred at room temperature for 3 days, and the mixture was diluted with dichloromethane (200 mL). The solution was washed with water and brine, dried over magnesium sulfate, and evapolated. The residue was purified by column chromatography on silica gel (40 g) eluting with hexane/ethyl acetate (10/1) to afford 545 mg (49%) of the title compound:

$^1$H-NMR (CDCl$_3$) δ 7.42 (1H, d, J=2.8 Hz), 7.12 (1H, d, J=8.4 Hz), 6.91 (1H, dd, J=8.4, 2.8 Hz), 3.89 (3H, s), 2.51 (3H, s); MS (EI) 166 (M)$^+$.

Step 2. Methyl 5-{[tert-butyl(dimethyl)silyl]oxy}-2-methylbenzoate

The title compound was prepared according to the procedure described in step 1 of example 9 from methyl 5-hydroxy-2-methylbenzoate (step 1):

$^1$H-NMR (CDCl$_3$) δ 7.87 (1H, d, J=2.6 Hz), 7.09 (1H, d, J=8.3 Hz), 6.89 (1H, dd, J=8.3, 2.6 Hz), 3.88 (3H, s), 2.51 (3H, s), 0.98 (9H, s), 0.19 (6H, s).

Step 3. (5-{[tert-Butyl(dimethyl)silyl]oxy}-2-methylphenyl)methanol

To a stirred solution of methyl 5-{[tert-butyl(dimethyl)silyl]oxy}-2-methylbenzoate (step 2, 810 mg, 2.89 mmol) in dichloromethane (15 mL) was added a 0.95 M solution of diisobutylaluminum hydride in hexane (6.69 mL, 6.35 mmol) at –78° C. The mixture was stirred at –78° C. for 2 h. The reaction was quenched by addition of water (6.7 mL) at –78° C. The mixture was diluted with dichloromethane (50 mL) and hexane (50 mL), and the mixture was stirred at room temperature for 16 h. The mixture was dried over magnesium sulfate, concentrated to afford 724 mg (99%) of the title compound as a colorless oil:

$^1$H-NMR (CDCl$_3$) δ 7.02 (1H, d, J=8.1 Hz), 6.88 (1H, d, J=2.6 Hz), 6.68 (1H, dd, J=8.1, 2.6 Hz), 4.64 (2H, d, J=5.6 Hz), 2.26 (3H, s), 1.48 (1H, t, J=5.6 Hz), 0.98 (9H, s), 0.19 (6H, s).

Step 4. [3-(Bromomethyl)-4-methylphenoxyl](tert-butyl)dimethylsilane

The title compound was prepared according to the procedure described in step 2 of example 14 from (5-{[tert-butyl(dimethyl)silyl]oxy}-2-methylphenyl)methanol (step 3).

$^1$H-NMR (CDCl$_3$) δ 7.02 (1H, d, J=8.3 Hz), 6.80 (1H, d, J=2.6 Hz), 6.70 (1H, dd, J=8.3, 2.6 Hz), 4.44 (2H, s), 2.32 (3H, s), 0.98 (9H, s), 0.18 (6H, s).

Step 5. tert-Butyl 2-(5-{[tert-butyl(dimethyl)silyl]oxy}-2-methylbenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate (WO 2003064425) and [3-(bromomethyl)-4-methylphenoxy](tert-butyl)dimethylsilane (step 4):

¹H-NMR (CDCl₃) δ 7.30-7.07 (4H, m), 6.96 (1H, d, J=8.2 Hz), 6.67 (1H, d, J=2.6 Hz), 6.58 (1H, dd, J=8.2, 2.6 Hz), 5.06 (2H, s), 2.92-2.70 (6H, m), 2.52-2.32 (3H, m), 2.24 (3H, s), 1.99-1.83 (2H, m), 1.78-1.68 (2H, m), 1.39 (9H, s), 0.97 (9H, s), 0.17 (6H, s); MS (ESI) 552 (M+H)⁺.

Step 6. 2-(5-{[tert-Butyl(dimethyl)silyl]oxy}-2-methylbenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(5-{[tert-butyl(dimethyl)silyl]oxy}-2-methylbenzyl)-3-(1'H,3H-spiro[2-benzofuran-1,4'-piperidin]-1'-yl)propanoate (step 5):
¹H-NMR (CDCl₃) δ 7.38-6.79 (5H, m), 6.67 (1H, dd, J=8.3, 2.6 Hz), 6.59 (1H, d, J=2.6 Hz), 5.04 (2H, s), 3.69-2.14 (1H, m), 2.26 (3H, s), 1.91-1.76 (2H, m), 0.98 (9H, s), 0.18 (6H, s); MS (ESI) 496 (M+H)⁺.

Example 23

2-(2-Chlorobenzyl)-3-(6-fluoro-1'H,3H-spiro[2-benzofuran-1,4'-piperidin]-1'-yl)propanoic acid

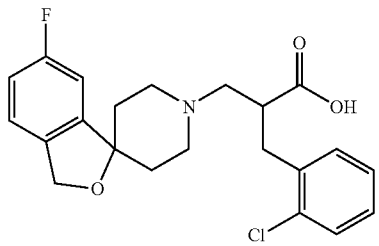

Step 1. Ethyl 2-(2-chlorobenzyl)-3-(6-fluoro-1'H, 3H-spiro[2-benzofuran-1,4'-piperidin]-1'-yl)propanoate The title compound was prepared according to the procedure described in step 4 of example 4 from 6-fluoro-3H-spiro[2-benzofuran-1,4'-piperidine] (*J. Med. Chem.* 1995, 38, 2009.) and ethyl 2-(2-chlorobenzyl)acrylate (step 2 of example 17):
¹H-NMR (CDCl₃) δ 7.36-7.32 (1H, m), 7.24-7.10 (4H, m), 6.95 (1H, dt, J=8.8, 2.2 Hz), 6.79 (1H, dd, J=8.4, 2.2 Hz), 5.00 (2H, s), 4.16-4.04 (2H, m), 3.15-3.05 (2H, m), 2.95-2.76 (4H, m), 2.56-2.33 (3H, m), 1.86 (2H, dt, J=12.5, 4.8 Hz), 1.75-1.69 (2H, m), 1.14 (3H, t, J=7.2 Hz); MS (ESI) 432 (M+H)⁺.

Step 2. 2-(2-Chlorobenzyl)-3-(6-fluoro-1'H,3H-spiro[2-benzofuran-1,4'-piperidin]-1'-yl)propanoic acid The title compound was prepared according to the procedure described in step 5 of example 4 from ethyl 2-(2-chlorobenzyl)-3-(6-fluoro-1'H,3H-spiro[2-benzofuran-1,4'-piperidin]-1'-yl)propanoate (step 1):
¹H-NMR (DMSO-d₆) δ 7.42-7.35 (2H, m), 7.30-7.04 (5H, m), 4.91 (2H, s), 3.65-3.27 (1H, m), 2.58-2.50 (5H, m), 2.39-2.14 (3H, m), 1.93-1.74 (2H, m), 1.61-1.53 (2H, m); MS (ESI) 404 (M+H)⁺, 402 (M−H)⁻.

Example 24

2-(2-Fluoro-5-hydroxybenzyl)-3-(6-fluoro-1'H,3H-spiro[2-benzofuran-1,4'-piperidin]-1'-yl)propanoic acid

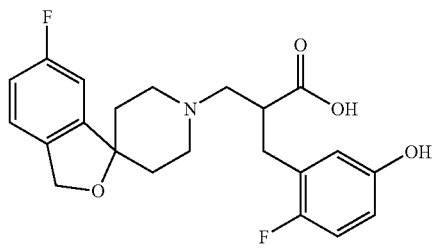

Step 1. Ethyl 2-(5-{[tert-butyl(dimethyl)silyl]oxy}-2-fluorobenzyl)-3-(6-fluoro-1'H,3H-spiro[2-benzofuran-1,4'-piperidin]-1'-yl)propanoate The title compound was prepared according to the procedure described in step 4 of example 4 from 6-fluoro-3H-spiro[2-benzofuran-1,4'-piperidine] (*J. Med. Chem.* 1995, 38, 2009.) and ethyl 2-(5-{[tert-butyl(dimethyl)silyl]oxy}-2-fluorobenzyl)acrylate (step 2 of example 19):
¹H-NMR (CDCl₃) δ 7.12 (1H, dd, J=8.3, 4.8 Hz), 6.98-6.77 (3H, m), 6.67-6.60 (2H, m), 5.00 (2H, s), 4.24-4.05 (2H, m), 2.98-2.72 (6H, m), 2.52-2.32 (3H, m), 1.91-1.82 (2H, m), 1.76-1.68 (2H, m), 1.19 (3H, t, J=7.2 Hz), 0.97 (9H, s), 0.17 (6H, s); MS (ESI) 546 (M+H)⁺.

Step 2. 2-(2-Fluoro-5-hydroxybenzyl)-3-(6-fluoro-1'H,3H-spiro[2-benzofuran-1,4'-piperidin]-1'-yl)propanoic acid The title compound was prepared according to the procedure described in step 5 of example 4 from ethyl 2-(5-{[tert-butyl(dimethyl)silyl]oxy}-2-fluorobenzyl)-3-(6-fluoro-1'H,3H-spiro[2-benzofuran-1,4'-piperidin]-1'-yl)propanoate (step 1):
¹H-NMR (DMSO-d₆) δ 9.28 (1H, s), 7.29 (1H, dd, J=8.3, 5.0 Hz), 7.18 (1H, dd, J=9.1, 2.1 Hz), 7.12-7.06 (1H, m), 6.93 (1H, dd, J=9.8, 8.9 Hz), 6.66-6.56 (2H, m), 4.93 (2H, s), 3.74-3.28 (1H, m), 2.93-2.64 (6H, m), 2.52-2.25 (3H, m), 1.96-1.82 (2H, m), 1.67-1.57 (2H, m); MS (ESI) 404 (M+H)⁺, 402 (M−H)⁻.

Example 25

2-Benzyl-3-(6-fluoro-1'H,3H-spiro[2-benzofuran-1,4'-piperidin]-1'-yl)propanoic acid trifluoroacetate

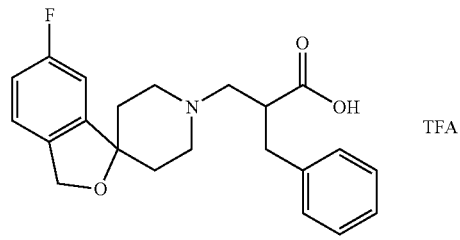

Step 1. tert-Butyl 2-benzyl-3-(6-fluoro-1'H,3H-spiro[2-benzofuran-1,4'-piperidin]-1'-yl)propanoate The title compound was prepared according to the procedure described in step 4 of example 4 from 6-fluoro-3H-spiro[2-benzofuran-1,4'-piperidine] (*J. Med. Chem.* 1995, 38, 2009.) and tert-butyl 2-benzylacrylate (*Tetrahedron Lett.* 1990, 31, 4413.):
¹H-NMR (CDCl₃) δ 7.30-7.11 (6H, m), 6.98-6.92 (1H, m), 6.78 (1H, dd, J=8.3, 2.3 Hz), 5.01 (2H, s), 2.89-2.69 (6H, m), 2.50-2.32 (3H, m), 1.92-1.71 (4H, m), 1.36 (9H, s); MS (ESI) 426 (M+H)⁺.

Step 2. 2-Benzyl-3-(6-fluoro-1'H,3H-spiro[2-benzofuran-1,4'-piperidin]-1'-yl)propanoic acid trifluoroacetate The title compound was prepared according to the procedure described in step 3 of example 1 from tert-butyl 2-benzyl-3-(6-fluoro-1'H,3H-spiro[2-benzofuran-1,4'-piperidin]-1'-yl)propanoate (step 1):
¹H-NMR (CDCl₃) δ 7.38-7.29 (3H, m), 7.21-7.14 (3H, m), 7.05-6.99 (1H, m), 6.79 (1H, dd, J=8.1, 2.2 Hz), 5.01 (2H, s), 3.70-3.53 (3H, m), 3.42-3.24 (3H, m), 3.03-2.70 (3H, m), 2.42-2.28 (2H, m), 1.94-1.84 (2H, m); MS (ESI) 370 (M+H)⁺, 368 (M−H)⁻.

Example 26

2-(2-Chloro-5-hydroxybenzyl)-3-(1-methyl-2-oxo-1,2-dihydro-1'H-spiro[indole-3,4'-piperidin]-1'-yl)propanoic acid

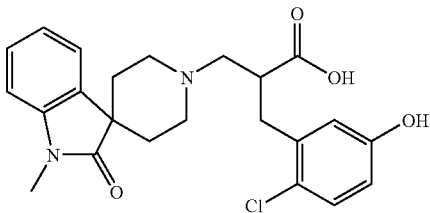

Step 1. Ethyl 2-(5-{[tert-butyl(dimethyl)silyl]oxy}-2-chlorobenzyl)-3-(1-methyl-2-oxo-1,2-dihydro-1'H-spiro[indole-3,4'-piperidin]-1'-yl)propanoate The title compound was prepared according to the procedure described in step 4 of example 4 from 1-methylspiro[indole-3,4'-piperidin]-2(1H)-one (step 3 of example 10) and ethyl 2-(5-{[tert-butyl(dimethyl)silyl]oxy}-2-chlorobenzyl)acrylate (step 2 of example 30):
¹H-NMR (CDCl₃) δ 7.39 (1H, d, J=6.6 Hz), 7.31-7.25 (1H, m), 7.18 (d, J=8.7 Hz), 7.04 (1H, dt, J=7.5, 1.0 Hz), 6.84 (1H, d, J=7.6 Hz), 6.73-6.70 (1H, m), 6.64 (1H, dd, J=8.6, 3.0 Hz), 4.26-4.04 (2H, m), 3.19 (3H, s), 3.12-2.58 (9H, m), 1.98-1.87 (2H, m), 1.79-1.69 (2H, m), 0.97 (9H, s), 0.18 (6H, s); MS (ESI) 571 (M+H)⁺.

Step 2. 2-(2-Chloro-5-hydroxybenzyl)-3-(1-methyl-2-oxo-1,2-dihydro-1'H-spiro[indole-3,4'-piperidin]-1'-yl)propanoic acid The title compound was prepared according to the procedure described in step 4 of example 30 from ethyl 2-(2-chlorobenzyl)-3-(1-methyl-2-oxo-1,2-dihydro-1'H-spiro[indole-3,4'-piperidin]-1'-yl)propanoate (step 1):
MS (ESI) 429 (M+H)⁺, 427 (M−H)⁻.

Example 27

2-(2-Chloro-5-fluorobenzyl)-3-(1'H,3H-spiro[2-benzofuran-1,4'-piperidin]-1'-yl)propanoic acid trifluoroacetate

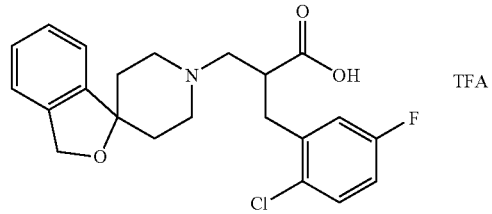

Step 1. tert-Butyl 2-(2-chloro-5-fluorobenzyl)-3-(1'H,3H-spiro[2-benzofuran-1,4'-piperidin]-1'-yl)propanoate The title compound was prepared according to the procedure described in step 2 of example 1 from tert-butyl 3-(1'H,3H-spiro[2-benzofuran-1,4'-piperidin]-1'-yl)propanoate and 2-(bromomethyl)-1-chloro-4-fluorobenzene (*J. Heterocyclic Chem.* 1997, 34, 27.):
¹H-NMR (CDCl₃) δ 7.36-7.09 (5H, m), 7.01 (1H, dd, J=9.2, 3.0 Hz), 6.88 (1H, td, J=8.3, 3.0 Hz), 5.06 (2H, s), 3.08-2.70 (6H, m), 2.55-2.37 (3H, m), 1.97-1.67 (4H, m), 1.38 (9H, s); MS (ESI) 460 (M+H)⁺.

Step 2. 2-(2-Chloro-5-fluorobenzyl)-3-(1'H,3H-spiro[2-benzofuran-1,4'-piperidin]-1'-yl)propanoic acid trifluoroacetate The title compound was prepared according to the procedure described in step 3 of example 1 from tert-butyl 2-(2-chloro-5-fluorobenzyl)-3-(1'H,3H-spiro[2-benzofuran-1,4'-piperidin]-1'-yl)propanoate (step 1):
¹H-NMR (CDCl₃) δ 7.37-7.10 (5H, m), 7.05-6.91 (2H, m), 5.07 (2H, s), 3.76-3.57 (3H, m), 3.48-3.09 (4H, m), 3.00-2.87 (2H, m), 2.54-2.27 (2H, m), 1.98-1.80 (2H, m); MS (ESI) 404 (M+H)⁺.

Example 28

2-(5-{[tert-Butyl(dimethyl)silyl]oxy}-2-fluorobenzyl)-3-(5-fluoro-1-methyl-1,2-dihydro-1'H-spiro[indole-3,4'-piperidin]-1'-yl)propanoic acid trifluoroacetate

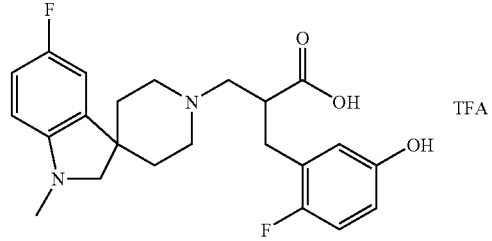

Step 1. tert-Butyl 3-(5-fluoro-1-methyl-1,2-dihydro-1'H-spiro[indole-3,4'-piperidin]-1'-yl)propanoate The title compound was prepared according to the procedure described in step 1 of example 1 from 5-fluoro-1-methyl-1,2-dihydrospiro[indole-3,4'-piperidine] (step 3 of example 4):

$^1$H-NMR (CDCl$_3$) δ 6.81-6.74 (2H, m), 6.36 (1H, dd, J=8.0, 4.2 Hz), 3.18 (2H, s), 2.89-2.82 (2H, m), 2.72 (3H, s), 2.68 (2H, d, J=7.8 Hz), 2.45 (2H, t, J=7.4 Hz), 2.14 (2H, dt, J=11.8, 2.7 Hz), 1.86 (2H, dt, J=12.7, 3.8 Hz), 1.71 (2H, br.d, J=12.0 Hz), 1.46 (9H, s); MS (ESI) 349 (M+H)$^+$.

Step 2. tert-Butyl 2-(5-{[tert-butyl(dimethyl)silyl]oxy}-2-fluorobenzyl)-3-(5-fluoro-1-methyl-1,2-dihydro-1'H-spiro[indole-3,4'-piperidin]-1'-yl)propanoate The title compound was prepared according to the procedure described in step 2 of example 1 from tert-butyl 3-(5-fluoro-1-methyl-1,2-dihydro-1'H-spiro[indole-3,4'-piperidin]-1'-yl)propanoate (step 1) and [3-(bromomethyl)-4-fluorophenoxy](tert-butyl)dimethylsilane (step 2 of example 9):

$^1$H-NMR (CDCl$_3$) δ 6.91-6.59 (5H, m), 6.35 (1H, dd, J=8.3, 4.1 Hz), 3.16 (2H, s), 2.93-2.64 (9H, m), 2.42 (1H, dd, J=12.1, 5.7 Hz), 2.20-2.04 (2H, m), 1.86-1.76 (2H, m), 1.69-1.63 (2H, m), 1.38 (9H, s), 0.97 (9H, s), 0.17 (6H, s); MS (ESI) 587 (M+H)$^+$.

Step 3. 2-(5-{[tert-Butyl(dimethyl)silyl]oxy}-2-fluorobenzyl)-3-(5-fluoro-1-methyl-1,2-dihydro-1'H-spiro[indole-3,4'-piperidin]-1'-yl)propanoic acid trifluoroacetate The title compound was prepared according to the procedure described in step 3 of example 1 from tert-butyl 2-(5-{[tert-butyl(dimethyl)silyl]oxy}-2-fluorobenzyl)-3-(5-fluoro-1-methyl-1,2-dihydro-1'H-spiro[indole-3,4'-piperidin]-1'-yl)propanoate (step 2):
MS (ESI) 531 (M+H)$^+$, 529 (M−H)$^−$.

Example 29

2-(5-{[tert-Butyl(dimethyl)silyl]oxy}-2-chlorobenzyl)-3-(5-fluoro-1-methyl-1,2-dihydro -1'H-spiro[indole-3,4'-piperidin]-1'-yl)propanoic acid trifluoroacetate

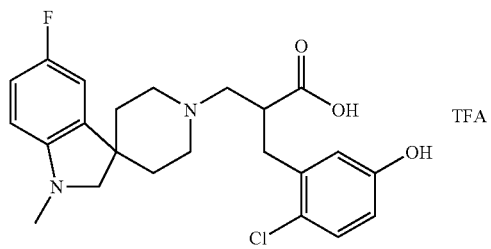

Step 1. tert-Butyl 2-(5-{[tert-butyl(dimethyl)silyl]oxy}-2-chlorobenzyl)-3-(5-fluoro-1-methyl-1,2-dihydro-1'H-spiro[indole-3,4'-piperidin]-1'-yl)propanoate The title compound was prepared according to the procedure described in step 2 of example 1 from tert-butyl 3-(5-fluoro-1-methyl-1,2-dihydro-1'H-spiro[indole-3,4'-piperidin]1'-yl)propanoate (step 1 of example 28) and [3-(bromomethyl)-4-chlorophenoxy](tert-butyl)dimethylsilane (J. Org. Chem. 1996, 61, 6974.):

$^1$H-NMR (CDCl$_3$) δ 7.17 (1H, d, J=8.6 Hz), 6.80-6.71 (3H, m), 6.63 (1H, dd, J=8.6, 2.9 Hz), 6.35 (1H, dd, J=8.3, 4.1 Hz), 3.16 (2H, s), 2.95-2.66 (9H, m), 2.43 (1H, dd, J=12.2, 5.6 Hz), 2.21-2.08 (2H, m), 1.86-1.75 (2H, m), 1.70-1.63 (2H, m), 1.39 (9H, s), 0.97 (9H, s), 0.18 (6H, s); MS (ESI) 603 (M+H)$^+$.

Step 2. 2-(5-{[tert-Butyl(dimethyl)silyl]oxy}-2-chlorobenzyl)-3-(5-fluoro-1-methyl-1,2-dihydro-1'H-spiro[indole-3,4'-piperidin]-1'-yl)propanoic acid trifluoroacetate The title compound was prepared according to the procedure described in step 3 of example 1 from tert-butyl 2-(5-{[tert-butyl(dimethyl)silyl]oxy}-2-chlorobenzyl)-3-(5-fluoro-1-methyl-1,2-dihydro-1'H-spiro[indole-3,4'-piperidin]-1'-yl)propanoate (step 1):
MS (ESI) 547 (M+H)$^+$, 545 (M−H)$^−$.

Example 30

2-(2-Chloro-5-hydroxybenzyl)-3-(5-fluoro-1-methyl-2-oxo-1,2-dihydro-1'H-spiro[indole-3,4'-piperidin]-1'-yl)propanoic acid

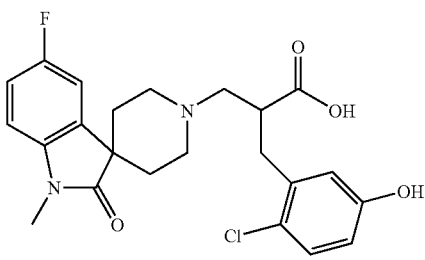

Step 1. Ethyl 3-(5-{[tert-butyl(dimethyl)silyl]oxy}-2-chlorophenyl)-2-(diethoxyphosphoryl)propanoate The title compound was prepared according to the procedure described in step 1 of example 17 from [3-(bromomethyl)-4-chlorophenoxy](tert-butyl)dimethylsilane (J. Org. Chem. 1996, 61, 6974.):

$^1$H-NMR (CDCl$_3$) δ 7.18 (1H, d, J=8.6 Hz), 6.75 (1H, d, J=2.8 Hz), 6.65 (1H, dd, J=8.6, 2.8 Hz), 4.30-4.02 (6H, m), 3.50-3.10 (3H, m), 1.37 (3H, t, J=7.1 Hz), 1.36 (3H, t, J=7.1 Hz), 1.19 (3H, t, J=7.1 Hz), 0.96 (9H, s), 0.17 (6H, s).

Step 2. Ethyl 2-(5-{[tert-butyl(dimethyl)silyl]oxy}-2-chlorobenzyl)acrylate

The title compound was prepared according to the procedure described in step 2 of example 17 from ethyl 3-(5-{[tert-butyl(dimethyl)silyl]oxy}-2-chlorophenyl)-2-(diethoxyphosphoryl)propanoate (step 1):

$^1$H-NMR (CDCl$_3$) δ 7.21 (1H, d, J=8.6 Hz), 6.72 (1H, d, J=2.8 Hz), 6.66 (1H, dd, J=8.6, 2.8 Hz), 6.28-6.25 (1H, m), 5.36-5.32 (1H, m), 4.22 (2H, q, J=7.1 Hz), 3.68 (2H, s), 1.29 (3H, t, J=7.1 Hz), 0.96 (9H, s), 0.17 (6H, s).

Step 3. Ethyl 2-(5-{[tert-butyl(dimethyl)silyl]oxy}-2-chlorobenzyl)-3-(5-fluoro-1-methyl-2-oxo-1,2-dihydro-1'H-spiro[indole-3,4'-piperidin]-1'-yl)propanoate The title compound was prepared according to the procedure described in step 4 of example 4 from 5-fluoro-1-methylspiro[indole-3,4'-piperidin]-2(1H)-one (step 3 of example 6) and ethyl 2-(5-{[tert-butyl(dimethyl)silyl]oxy}-2-chlorobenzyl)acrylate (step 2):

$^1$H-NMR (CDCl$_3$) δ 7.18 (1H, d, J=8.6 Hz), 7.14 (1H, dd, J=8.3, 2.4 Hz), 7.02-6.93 (1H, m), 6.77-6.70 (2H, m), 6.64 (1H, dd, J=8.6, 2.9 Hz), 4.20-4.00 (2H, m), 3.18 (3H, s), 3.15-2.80 (6H, m), 2.75-2.50 (3H, m), 2.00-1.85 (2H, m), 1.75-1.60 (2H, m), 1.20 (3H, t, J=7.2 Hz), 0.97 (9H, s), 0.18 (6H, s). MS (ESI) 589 (M+H)$^+$.

Step 4. 2-(2-Chloro-5-hydroxybenzyl)-3-(5-fluoro-1-methyl-2-oxo-1,2-dihydro-1'H-spiro[indole-3,4'-piperidin]-1'-yl)propanoic acid To a stirred solution of ethyl 2-(5-{[tert-butyl(dimethyl)silyl]oxy}-2-chlorobenzyl)-3-(5-fluoro-1-methyl-2-oxo-1,2-dihydro-1'H-spiro [indole-3,4'-piperidin]-1'-yl)propanoate (step 3, 0.79 g, 1.3 mmol) in tetrahydrofuran (5 mL) and methanol (3 mL) was added 2 N sodium hydroxide aqueous solution (3.5 mL) at room temperature. The reaction mixture was stirred at room temperature for 20 h, evaporated to remove methanol, and acidified with sodium hydrogenphosphate aqueous solution (pH=4-5). The aqueous layer was extracted with ethyl acetate. The organic layer was washed with brine, dried over magnesium sulfate, and evaporated to afford 0.65 g (quant.) of the title compound as a white solid:

$^1$H-NMR (DMSO-d$_6$) δ 9.62 (1H, s), 7.53-7.43 (1H, m), 7.20 (1H, d, J=7.9 Hz), 7.17-7.08 (1H, m), 7.07-6.98 (1H, m), 6.74 (1H, d, J=2.5 Hz), 6.65 (1H, dd, J=7.9, 2.5 Hz), 3.11 (3H, s), 3.10-2.60 (9H, m), 1.98-1.60 (4H, m); MS (ESI) 447 (M+H)$^+$, 445 (M-H)$^-$.

Example 31

2-(2-Fluoro-5-hydroxybenzyl)-3-(5-fluoro-1-methyl-2-oxo-1,2-dihydro-1'H-spiro[indole-3,4'-piperidin]-1'-yl)propanoic acid

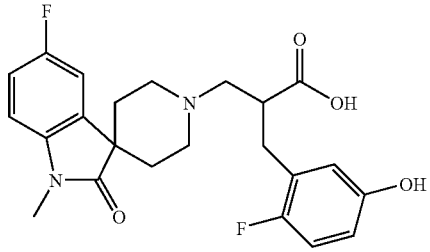

Step 1. Ethyl 2-(5-{[tert-butyl(dimethyl)silyl]oxy}-2-fluorobenzyl)-3-(5-fluoro-1-methyl-2-oxo-1,2-dihydro-1'H-spiro[indole-3,4'-piperidin]-1'-yl)propanoate The title compound was prepared according to the procedure described in step 4 of example 4 from 5-fluoro-1-methylspiro[indole-3,4'-piperidin]-2(1H)-one (step 3 of example 6) and ethyl 2-(5-{[tert-butyl(dimethyl)silyl]oxy}-2-fluorobenzyl)acrylate (step 2 of example 19):

$^1$H-NMR (CDCl$_3$) δ 7.14 (1H, dd, J=8.3, 2.4 Hz), 7.02-6.93 (1H, m), 6.90-6.82 (1H, m), 6.74 (1H, dd, J=8.5, 4.1 Hz), 6.68-6.59 (2H, m), 4.18-4.04 (2H, m), 3.18 (3H, s), 3.07-2.53 (9H, m), 2.00-1.85 (2H, m), 1.77-1.63 (2H, m), 1.20 (3H, t, J=7.2 Hz), 0.97 (9H, s), 0.17 (6H, s); MS (ESI) 573 (M+H)$^+$.

Step 2. 2-(2-Fluoro-5-hydroxybenzyl)-3-(5-fluoro-1-methyl-2-oxo-1,2-dihydro-1'H-spiro[indole-3,4'-piperidin]-1'-yl)propanoic acid The title compound was prepared according to the procedure described in step 5 of example 4 from ethyl 2-(5-{[tert-butyl(dimethyl)silyl]oxy}-2-fluorobenzyl)-3-(5-fluoro-1-methyl-2-oxo-1,2-dihydro-1'H-spiro[indole-3,4'-piperidin]-1'-yl)propanoate (step 1):

$^1$H-NMR (DMSO-d$_6$) δ 9.27 (1H, s), 7.52-7.43 (1H, m), 7.19-7.08 (1H, m), 7.02 (1H, dd, J=8.2, 4.2 Hz), 6.93 (1H, t, J=9.1 Hz), 6.69-6.55 (2H, m), 3.11 (3H, s), 3.05-2.45 (9H, m), 1.88-1.58 (4H, m); MS (ESI) 431 (M+H)$^+$, 429 (M-H)$^-$.

Example 32

3-(1'H,3H-Spiro[2-benzofuran-1,4'-piperidin]-1'-yl)-2-(1,3-thiazol-4-ylmethyl)propanoic acid trifluoroacetate

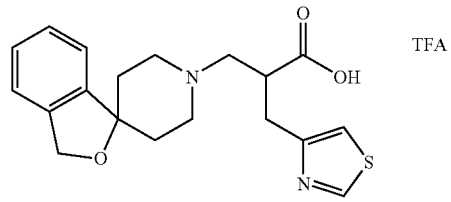

Step 1. tert-Butyl 3-(1'H,3H-spiro[2-benzofuran-1,4'-piperidin]-1'-yl)-2-(1,3-thiazol-4-ylmethyl)propanoate A mixture of 4-methyl-1,3-thiazole (505 mg, 5.09 mmol), N-bromosuccinimide (952 mg, 5.35 mmol) and 2,2'-azobisisobutyronitrile (83.5 mg, 0.509 mmol) in carbon tetrachloride (20 mL) was reflux under nitrogen atmosphere for 2 h. The reaction mixture was cooled to room temperature, and the resulting white precipitate was filtered. The filtrate was diluted with toluene and partially evaporated to afford crude 4-(bromomethyl)-1,3-thiazole as a toluene solution, which was used in the next step without purification.

To a stirred solution of tert-butyl 3-(1'H,3H-spiro[2-benzofuran-1,4'-piperidin]-1'-yl)propanoate (WO 2003064425, 450 mg, 1.42 mmol) in tetrahydrofuran (10 mL) was added dropwise a 1.0 M solution of lithium bis(trimethylsilyl)amide in tetrahydrofuran (1.84 mL, 1.84 mmol) at −78° C. and the mixture was stirred for 30 min at the same temperature. To the mixture was added 1,3-dimethyl-3,4,5,6-tetrahydro-2(1H)-pyrimidinone (0.223 mL, 1.84 mmol) at −78° C. and stirred for 30 min at the same temperature. To the resulting mixture was added a solution of crude 4-(bromomethyl)-1,3-thiazole in tetrahydrofuran (2 mL) and the reaction mixture was stirred at the same temperature for 30 min and then at −30° C. for 2 h. The reaction mixture was quenched by the addition of saturated ammonium chloride aqueous solution. The mixture was extracted with ethyl acetate (150 mL), and then the combined organic layers were washed with brine, dried over sodium sulfate, and evaporated. The residue was purified by column chromatography on silica gel (40 g) eluting with hexane/ethyl acetate (2/1) to afford 181 mg (31%) of the title compound as a yellow oil:

$^1$H-NMR (CDCl$_3$) δ 8.75 (1H, d, J=1.7 Hz), 7.33-7.07 (4H, m), 7.03 (1H, d, J=1.7 Hz), 5.06 (2H, m), 3.16-2.68

(6H, m), 2.57-2.32 (3H, m), 1.99-1.86 (2H, m), 1.82-1.67 (2H, m), 1.39 (9H, s); MS (ESI) 415 (M+H)+.

Step 2. 3-(1'H,3H-Spiro[2-benzofuran-1,4'-piperidin]-1'-yl)-2-(1,3-thiazol-4-ylmethyl)propanoic acid trifluoroacetate The title compound was prepared according to the procedure described in step 3 of example 1 from tert-butyl 3-(1'H,3H-spiro[2-benzofuran-1,4'-piperidin]-1'-yl)-2-(1,3-thiazol-4-ylmethyl)propanoate (step 1):

$^1$H-NMR (CDCl$_3$) δ 9.20 (1H, s), 7.54 (1H, s), 7.47-7.11 (4H, m), 5.09 (2H, s), 3.89-3.19 (9H, m), 2.48-2.27 (2H, m), 2.03-1.84 (2H, m); MS (ESI) 359 (M+H)+, 357 (M−H)−.

Example 33

3-(6-Fluoro-1'H,3H-spiro[2-benzofuran-1,4'-piperidin]-1'-yl)-2-(pyridin-2-ylmethyl)propanoic acid

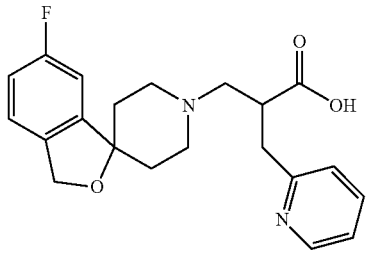

Step 1. Ethyl 3-(6-fluoro-1'H,3H-spiro[2-benzofuran-1,4'-piperidin]-1'-yl)-2-(pyridin-2-ylmethyl)propanoate The title compound was prepared according to the procedure described in step 4 of example 4 from 6-fluoro-3H-spiro[2-benzofuran-1,4'-piperidine] (*J. Med. Chem.* 1995, 38, 2009.) and ethyl 2-(pyridin-2-ylmethyl)acrylate (*Polym. J.* 2000, 32, 173.):

$^1$H-NMR (CDCl$_3$) δ 8.56-8.50 (1H, m), 7.63-7.53 (1H, m), 7.19-7.08 (3H, m), 6.99-6.90 (1H, m), 6.77 (1H, dd, J=8.6, 2.2 Hz), 5.00 (2H, s), 4.18-4.04 (2H, m), 3.33-3.20 (1H, m), 3.15-2.70 (5H, m), 2.57-2.28 (3H, m), 1.92-1.60 (4H, m), 1.17 (3H, t, J=7.2 Hz); MS (ESI) 399 (M+H)+.

Step 2. 3-(6-Fluoro-1'H,3H-spiro[2-benzofuran-1,4'-piperidin]-1'-yl)-2-(pyridin-2-ylmethyl)propanoic acid To a stirred solution of ethyl 3-(6-fluoro-1'H,3H-spiro[2-benzofuran-1,4'-piperidin]-1'-yl)-2-(pyridin-2-ylmethyl)propanoate (step 1, 2.0 g, 5.1 mmol) in tetrahydrofuran (10 mL) and ethanol (15 mL) was added 2 N sodium hydroxide (10 mL) at room temperature. The reaction mixture was stirred at room temperature for 16 h, evaporated to remove ethanol, and neutralized by the addition of 2 N hydrochloric acid aqueous splution (10 mL). The aqueous mixture was evaporated to remove water, then diluted with toluene (10 mL), and concentrated to dryness. The residue was dissolved with ethyl acetate (100 mL), and filtered. The filtrate was evaporated to afford 1.9 g (quant.) of the title compound as a colorless amorphous solid:

$^1$H-NMR (CDCl$_3$) δ 8.52-8.46 (1H, m), 7.62-7.54 (1H, m), 7.28-7.22 (1H, m), 7.17-7.06 (2H, m), 7.00-6.91 (1H, m), 6.82 (1H, dd, J=8.3, 2.2 Hz), 4.99 (2H, s), 3.47-3.36 (1H, m), 3.30-3.14 (2H, m), 3.02-2.40 (6H, m), 2.13-1.90 (2H, m), 1.84-1.70 (2H, m); MS (ESI) 371 (M+H)+.

Example 34

2-(2-Chloro-5-hydroxybenzyl)-3-(3,3-dimethyl-1'H,3H-spiro[2-benzofuran-1,4'-piperidin]-1'-yl)propanoic acid

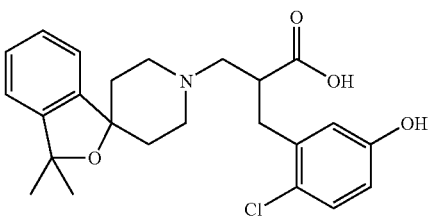

STEP 1. 2-(2-Bromophenyl)propan-2-ol

To a stirred solution of ethyl 2-bromobenzoate (10 g, 46.5 mmol) in tetrahydrofuran (80 mL) was added dropwise a 3.0 M solution of methylmagnesium chloride in tetrahydrofuran (39 mL, 0.116 mol) at room temperature and the mixture was stirred for 19 h at the same temperature. The reaction mixture was quenched by the addition of 2 N hydrochloric acid aqueous solution, and concentrated to give a colorless residue. The crude material was partitioned between diethyl ether and water, and then the organic layer was washed with brine, dried over sodium sulfate, and evaporated. The residue was purified by column chromatography on silica gel (150 g) eluting with hexane/ethyl acetate (15/1) to afford 6.91 g (69%) of the title compound as a colorless oil:

$^1$H-NMR (CDCl$_3$) δ 7.68-7.57 (2H, m), 7.33-7.25 (1H, m), 7.13-7.07 (1H, m), 1.75 (6H, s).

STEP 2. 4-[2-(1-Hydroxy-1-methylethyl)phenyl]-1-methylpiperidin-4-ol

To a stirred solution of 2-(2-bromophenyl)propan-2-ol (step 1, 6.91 g, 32.1 mmol) in tetrahydrofuran (32 mL) was added dropwise a 1.59 M solution of butyllithium in tetrahydrofuran (46.5 mL, 73.9 mmol) at −78° C. for 20 min and the mixture was stirred for 1 h at the same temperature. To the mixture was added dropwise a solution of 1-methylpiperidin-4-one (5.09 g, 45.0 mmol) in tetrahydrofuran (18 mL) at −78° C. for 10 min. This resulting mixture was slowly warmed up to room temperature and stirred for 18 h at the same temperature. The reaction mixture was quenched by the addition of water, and concentrated to give an orange residue. The crude material was partitioned between diethyl ether and water, and then the organic layer was washed with brine, dried over sodium sulfate, and evaporated. The residue was purified by column chromatography on silica gel (150 g) eluting with hexane/ethyl acetate (5/1), dichloromethane/methanol (10/1), then dichloromethane/methanol/triethylamine (10/1/1) to afford 4.62 g (58%) of the title compound as a slight yellow syrup:

MS (ESI) 250 (M+H)+.

STEP 3. 1',3,3-Trimethyl-3H-spiro[2-benzofuran-1,4'-piperidine]

To a stirred solution of 4-[2-(1-hydroxy-1-methylethyl)phenyl]-1-methylpiperidin-4-ol (step 2, 4.62 g, 18.5 mmol) in benzene (200 mL) was added dropwise boron trifluoride diethyl etherate (11.0 mL, 86.8 mmol) at room temperature and the mixture was stirred for 40 h at the same temperature. The reaction mixture was quenched by the addition of water (200 mL) and 2 N sodium hydroxide aqueous solution (200 mL), and the benzene layer was separated. The aqueous layer was extracted with diethyl ether, and then combined organic layer was washed with brine, dried over sodium sulfate, and evaporated. The residue was purified by column chromatography on an amine coated silica gel (100 g) eluting with dichloromethane to afford 2.39 g (56%) of the title compound as a colorless solid:

$^1$H-NMR (CDCl$_3$) δ 7.30-7.24 (2H, m), 7.12-7.07 (2H, m), 2.81-2.72 (2H, m), 2.51-2.42 (2H, m), 2.37 (3H, s), 2.07-1.97 (2H, m), 1.73-1.67 (2H, m), 1.50 (6H, s); MS (ESI) 233 (M+H)$^+$.

Step 4. 3,3-Dimethyl-3H-spiro[2-benzofuran-1,4'-piperidine]

To a stirred solution of 1',3,3-trimethyl-3H-spiro[2-benzofuran-1,4'-piperidine] (step 3, 2.39 g, 10.3 mmol) in 1,2-dichloroethane (50 mL) was added dropwise 1-chloroethyl chloroformate (2.68 mL, 24.8 mmol) at 0° C. and the mixture was stirred for 15 min at the same temperature. This resulting mixture was refluxed for 21 h. After cooling to room temperature, the mixture was concentrated to give a slight yellow solid.

This crude material was dissolved in methanol (30 mL), and refluxed for 19.5 h. After cooling to room temperature, the mixture was concentrated to give a slight yellow solid. The crude material was partitioned between diethyl ether and 1 N sodium hydroxide aqueous solution, and then the organic layer was washed with brine, dried over sodium sulfate, and evaporated. The residue was purified by column chromatography on an amine coated silica gel (50 g) eluting with dichloromethane to afford 1.02 g (45%) of the title compound as a slight yellow solid:

$^1$H-NMR (CDCl$_3$) δ 7.31-7.24 (2H, m), 7.13-7.09 (2H, m), 3.17-3.08 (2H, m), 3.03-2.97 (2H, m), 1.93-1.83 (2H, m), 1.70-1.65 (2H, m), 1.51 (6H, s); MS (ESI) 218 (M+H)$^+$.

Step 5. Ethyl 2-(2-chloro-5-hydroxybenzyl)-3-(3,3-dimethyl-1'H,3H-spiro[2-benzofuran-1,4'-piperidin]-1'-yl)propanoate and ethyl 2-(5-{[tert-butyl (dimethyl)silyl]oxy}-2-chlorobenzyl)-3-(3,3-dimethyl-1'H,3H-spiro[2-benzofuran-1,4'-piperidin]-1'-yl)propanoate The title compounds were prepared according to the procedure described in step 4 of example 4 from 3,3-dimethyl-3H-spiro[2-benzofuran-1,4'-piperidine] (step 4) and ethyl 2-(5-{[tert-butyl(dimethyl)silyl]oxy}-2-chlorobenzyl)acrylate (step 2 of example 30).

Ethyl 2-(2-chloro-5-hydroxybenzyl)-3-(3,3-dimethyl-1'H,3H-spiro[2-benzofuran-1,4'-piperidin]-1'-yl)propanoate $^1$H-NMR (CDCl$_3$) δ 7.29-7.21 (2H, m), 7.15 (1H, d, J=8.4 Hz), 7.09-7.03 (2H, m) 6.72 (1H, d, J=2.9 Hz), 6.65 (1H, dd, J=8.4, 2.9 Hz), 4.11-4.02 (2H, m), 3.19-3.09 (1H, m), 3.02-2.78 (5H, m), 2.62-2.46 (3H, m), 2.02-1.92 (2H, m), 1.67-1.62 (2H, m), 1.48 (6H, s), 1.14 (3H, t, J=7.2 Hz); MS (ESI) 458 (M+H)$^+$.

Ethyl 2-(5-{[tert-butyl(dimethyl)silyl]oxy}-2-chlorobenzyl)-3-(3,3-dimethyl-1'H,3H-spiro[2-benzofuran-1,4'-piperidin]-1'-yl)propanoate:

$^1$H-NMR (CDCl$_3$) δ 7.28-7.25 (2H, m), 7.18 (1H, d, J=8.4 Hz), 7.10-7.07 (2H, m), 6.72 (1H, d, J=2.9 Hz), 6.64 (1H, dd, J=8.4, 2.9 Hz), 4.17-4.04 (2H, m), 3.12-2.99 (2H, m), 2.89-2.75 (4H, m), 2.58-2.42 (3H, m), 1.98-1.88 (2H, m), 1.67-1.63 (2H, m), 1.49 (6H, s), 1.20 (3H, t, J=7.2 Hz), 0.97 (9H, s), 0.18 (6H, s); MS (ESI) 572 (M+H)$^+$.

Step 6. 2-(2-Chloro-5-hydroxybenzyl)-3-(3,3-dimethyl-1'H,3H-spiro[2-benzofuran-1,4'-piperidin]-1'-yl)propanoic acid The title compound was prepared according to the procedure described in step 5 of example 4 from ethyl 2-(2-chloro-5-hydroxybenzyl)-3-(3,3-dimethyl-1'H,3H-spiro[2-benzofuran-1,4'-piperidin]-1'-yl)propanoate (step 5) and ethyl 2-(5-{[tert-butyl (dimethyl)silyl]oxy}-2-chlorobenzyl)-3-(3,3-dimethyl-1'H,3H-spiro[2-benzofuran-1,4'-piperidin]-1'-yl)propanoate (step 5).

$^1$H-NMR (CDCl$_3$) δ 7.32-7.29 (2H, m), 7.13 (1H, d, J=8.6 Hz), 7.13-7.08 (2H, m), 6.81 (1H, d, J=2.9 Hz), 6.69 (1H, dd, J=8.6, 2.9 Hz), 3.48-3.42 (1H, m), 3.25-3.19 (1H, m), 3.04-2.92 (3H, m), 2.86-2.65 (4H, m), 2.19-2.01 (2H, m), 1.78-1.73 (2H, m), 1.46 (6H, s); MS (ESI) 430 (M+H)$^+$.

Example 35

2-(2-Chloro-5-hydroxybenzyl)-3-(2-hydroxy-2,3-dihydro-1'H-spiro[indene-1,4'-piperidin]-1'-yl)propanoic acid

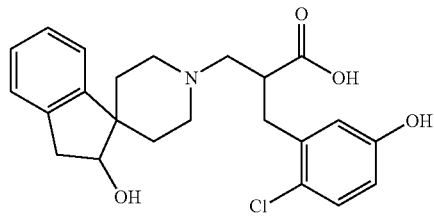

Step 1. Ethyl 2-(5-{[tert-butyl(dimethyl)silyl]oxy}-2-chlorobenzyl)-3-(2-hydroxy-2,3-dihydro-1'H-spiro[indene-1,4'-piperidin]-1'-yl)propanoate The title compound was prepared a diastereo mixture according to the procedure described in step 4 of example 4 from 2,3-dihydrospiro[indene-1,4'-piperidin]-2-ol (*Tetrahedron: Asymmetry* 1999, 10, 1787.) and ethyl 2-(5-{[tert-butyl(dimethyl)silyl]oxy}-2-chlorobenzyl)acrylate (step 2 of example 30):

$^1$H-NMR (CDCl$_3$) δ 7.23-7.16 (5H, m), 6.72-6.62 (2H, m), 4.46-4.44 (1H, m), 4.18-4.13 (2H, m), 3.33-3.25 (1H, m), 3.12-2.98 (2H, m), 2.91-2.71 (5H, m), 2.54-2.30 (2H, m), 2.02-1.93 (1H, m), 1.71-1.44 (4H, m), 1.22-1.15 (3H, m), 0.97 (9H, s), 0.18 (6H, s); MS (ESI) 558 (M+H)$^+$.

Step 2. 2-(2-Chloro-5-hydroxybenzyl)-3-(2-hydroxy-2,3-dihydro-1'H-spiro[indene-1,4'-piperidin]-1'-yl)propanoic acid The title compound was prepared a diastereo mixture according to the procedure described in step 4 of example 30 from ethyl 2-(5-{[tert-butyl(dimethyl)silyl]oxy}-2-chlorobenzyl)-3-(2-hydroxy-2,3-dihydro-1'H-spiro[indene-1,4'-piperidin]-1'-yl)propanoate (step 1): MS (ESI) 416 (M+H)⁺, 414 (M−H)⁻.

Example 36

2-(2-chloro-5-hydroxybenzyl)-3-(3-methyl-1'H,3H-spiro[2-benzofuran-1,4'-piperidin]-1'-yl)propanoic acid

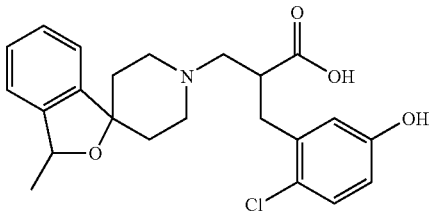

Step 1. 1-(2-Bromophenyl)ethanol

To a stirred solution of 1-(2-bromophenyl)ethanone (5 g, 25.1 mmol) in methanol (50 mL) was added sodium borohydride (1.43 g, 37.7 mmol) at room temperature and the mixture was stirred for 24 h at the same temperature. The reaction mixture was quenched by the addition of water, and concentrated to give a colorless residue. The crude material was partitioned between diethyl ether and water, and then the organic layer was washed with brine, dried over sodium sulfate, and evaporated. The residue was purified by column chromatography on silica gel (100 g) eluting with hexane/ethyl acetate (5/1) to afford 5.4 g (quant.) of the title compound as a colorless oil:
¹H-NMR (CDCl₃) δ 7.62-7.50 (2H, m), 7.37-7.32 (1H, m), 7.16-7.10 (1H, m), 5.28-5.21 (1H, dq, J=3.5, 6.4 Hz), 1.96 (1H, d, J=3.5 Hz), 1.49 (3H, d, J=6.4 Hz).

Step 2. Ethyl 4-hydroxy-4-[2-(1-hydroxyethyl)phenyl]piperidine-1-carboxylate

To a stirred solution of 1-(2-bromophenyl)ethanol (step 1, 5.4 g, 25.1 mmol) in tetrahydrofuran (25 mL) was added dropwise a 1.59 M solution of butyllithium in tetrahydrofuran (33 mL, 51.5 mmol) at −78° C. for 20 min and the mixture was stirred for 2 h at the same temperature. To the mixture was added dropwise a solution of ethyl 4-oxopiperidine-1-carboxylate (4.73 g, 27.6 mmol) in tetrahydrofuran (10 mL) at −78° C. for 15 min. This resulting mixture was slowly warmed up to room temperature and stirred for 19 h at the same temperature. The reaction mixture was quenched by the addition of saturated ammonium chloride aqueous solution, and then the organic layer was washed with brine, dried over sodium sulfate, and evaporated. The residue was purified by column chromatography on silica gel (150 g) eluting with hexane/ethyl acetate (2/1), then hexane/ethyl acetate (1/1) to afford 1.37 g (19%) of the title compound as a slight yellow syrup:
¹H-NMR (CDCl₃) δ 7.60-7.57 (1H, m), 7.33-7.23 (3H, m), 5.80-5.75 (1H, m), 4.17-4.05 (4H, m), 3.32 (2H, br.m), 3.08 (1H, br.s), 2.37 (1H, br.s), 1.99-1.87 (2H, m), 1.58 (3H, t, J=6.4 Hz), 1.29-1.23 (4H, m).

Step 3. Ethyl 3-methyl-1'H,3H-spiro[2-benzofuran-1,4'-piperidine]-1'-carboxylate To a stirred solution of ethyl 4-hydroxy-4-[2-(1-hydroxyethyl)phenyl]piperidine-1-carboxylate (step 2, 1.37 g, 4.67 mmol) in dichloromethane (30 mL), triethylamine (1 mL) and pyridine (3 mL) was added dropwise methanesulfonyl chloride (0.54 mL, 7.01 mmol) at 0° C. for 15 min. This resulting mixture was slowly warmed up to room temperature and stirred for 45 min at the same temperature, then refluxed for 3 h. The reaction mixture was washed with water, 2 N hydrochloric acid aqueous solution, dried over sodium sulfate, and evaporated. The residue was purified by column chromatography on silica gel (70 g) eluting with hexane/ethyl acetate (5/1) to afford the clude title compound as a slight yellow syrup. This material was dissolved in diethyl ether (20 mL) and ethyl acetate (20 mL), then washed with saturated sodium bicarbonate aqueous solution and brine, dried over sodium sulfate, and evaporated to afford 1.32 g (79%) of the title compound as a slight yellow syrup:
¹H-NMR (CDCl₃) δ 7.32-7.26 (2H, m), 7.16-7.03 (1H, m), 7.08-7.05 (1H, m), 5.30 (1H, q, J=6.2 Hz), 4.20-4.04 (4H, m), 3.31-3.19 (2H, m), 2.01-1.91 (2H, m), 1.75-1.58 (3H, m), 1.50 (3H, d, J=6.4 Hz), 1.28 (3H, t, J=7.2 Hz).

Step 4. 3-methyl-3H-spiro[2-benzofuran-1,4'-piperidine]

A solution of ethyl 3-methyl-1'H,3H-spiro[2-benzofuran-1,4'-piperidine]-1'-carboxylate (step 3, 1.02 g, 3.70 mmol) in 4 M sodium hydroxide aqueous solution (10 mL) and ethanol (20 mL) was refluxed for 2 days. The reaction mixture was concentrated to give a colorless residue. The crude material was partitioned between diethyl ether and water, and the organic layer was washed with brine, dried over sodium sulfate, and evaporated to afford 732 mg (97%) of the title compound as a slight yellow syrup:
¹H-NMR (CDCl₃) δ 7.29-7.26 (2H, m), 7.16-7.12 (2H, m), 5.29 (1H, q, J=6.4 Hz), 3.16-2.96 (4H, m), 2.02-1.92 (1H, m), 1.78-1.63 (3H, m), 1.50 (3H, d, J=6.4 Hz); MS (ESI) 204 (M+H)⁺.

Step 5. Ethyl 2-(2-chloro-5-hydroxybenzyl)-3-(3-methyl-1'H,3H-spiro[2-benzofuran-1,4'-piperidin]-1'-yl)propanoate and ethyl 2-(5-{[tert-butyl (dimethyl)silyl]oxy}-2-chlorobenzyl)-3-(3-methyl-1'H,3H-spiro[2-benzofuran-1,4'-piperidin]-1'-yl)propanoate The title compounds were prepared according to the procedure described in step 4 of example 4 from 3-methyl-3H-spiro[2-benzofuran-1,4'-piperidine] (step 4) and ethyl 2-(5-{[tert-butyl(dimethyl)silyl]oxy}-2-chlorobenzyl)acrylate (step 2 of example 30).

Ethyl 2-(2-chloro-5-hydroxybenzyl)-3-(3-methyl-1'H,3H-spiro[2-benzofuran-1,4'-piperidin]-1'-yl)propanoate

MS (ESI) 444 (M+H)⁺.

Ethyl 2-(5-{[tert-butyl(dimethyl)silyl]oxy}-2-chlorobenzyl)-3-(3-methyl-1'H,3H-spiro[2-benzofuran-1,4'-piperidin]-1'-yl)propanoate ¹H-NMR (CDCl₃) δ 7.28-7.25 (2H, m), 7.17 (1H, d, J=8.6 Hz), 7.13-7.09 (2H, m), 6.72 (1H, d, J=2.9 Hz), 6.63 (1H, dd, J=8.6, 2.9 Hz), 5.27 (1H, q, J=6.4 Hz), 3.07-2.99 (2H, m), 2.88-2.75 (4H, m), 2.55-2.36 (3H, m), 2.08-1.98 (1H, m), 1.86-1.76 (1H, m), 1.71-1.65 (2H, m), 1.48 (3H, d, J=6.4 Hz), 1.19 (3H, t, J=7.2 Hz), 0.97 (9H, s), 0.18 (6H, s); MS (ESI) 558 (M+H)$^+$.

Step 6. 2-(2-chloro-5-hydroxybenzyl)-3-(3-methyl-1'H,3H-spiro[2-benzofuran-1,4'-piperidin]-1'-yl)propanoic acid The title compound was prepared according to the procedure described in step 5 of example 4 from ethyl 2-(2-chloro-5-hydroxybenzyl)-3-(3-methyl-1'H,3H-spiro[2-benzofuran-1,4'-piperidin]-1'-yl)propanoate and ethyl 2-(5-{[tert-butyl (dimethyl)silyl]oxy}-2-chlorobenzyl)-3-(3-methyl-1'H,3H-spiro[2-benzofuran-1,4'-piperidin]-1'-yl)propanoate (step 5): MS (ESI) 416 (M+H)$^+$, 414 (M−H)$^−$.

Example 37

2-(2-Chloro-5-hydroxybenzyl)-3-(5,7-difluoro-1-methyl-1,2-dihydro-1'H-spiro[indole-3,4'-piperidin]-1'-yl)propanoic acid

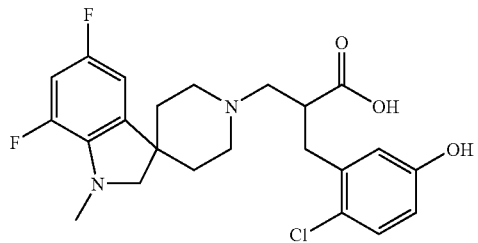

Step 1. Benzyl 5,7-difluoro-1,2-dihydro-1'H-spiro[indole-3,4'-piperidine]-1'-carboxylate The title compound was prepared according to the procedure described in step 1 of example 4 from (2,4-difluorophenyl)hydrazine hydrochloride:

$^1$H-NMR (CDCl$_3$) δ 7.39-7.32 (5H, m), 6.65-6.51 (2H, m), 5.16 (2H, s), 4.16 (2H, br.m), 3.25 (2H, s), 2.97 (2H, br.m), 1.72 (4H, br.m).

Step 2. Benzyl 5,7-difluoro-1-methyl-1,2-dihydro-1'H-spiro[indole-3,4'-piperidine]-1'-carboxylate The title compound was prepared according to the procedure described in step 2 of example 4 from benzyl 5,7-difluoro-1,2-dihydro-1'H-spiro[indole-3,4'-piperidine]-1'-carboxylate (step 1):

$^1$H-NMR (CDCl$_3$) δ 7.39-7.31 (5H, m), 6.65-6.51 (2H, m), 5.16 (2H, s), 4.16 (2H, br.m), 3.24 (2H, s), 2.95 (2H, br.m), 2.92 (3H, s), 1.72 (4H, br.m); MS (ESI) 373 (M+H)$^+$.

Step 3. 5,7-Difluoro-1-methyl-1,2-dihydrospiro[indole-3,4'-piperidine]

The title compound was prepared according to the procedure described in step 3 of example 4 from benzyl 5,7-difluoro-1-methyl-1,2-dihydro-1'H-spiro[indole-3,4'-piperidine]-1'-carboxylate (step 2):

MS (ESI) 234 (M+H)$^+$.

Step 4. Ethyl 2-(5-{[tert-butyl(dimethyl)silyl]oxy}-2-chlorobenzyl)-3-(5,7-difluoro-1-methyl-1,2-dihydro-1'H-spiro[indole-3,4'-piperidin]-1'-yl)propanoate The title compound was prepared according to the procedure described in step 4 of example 4 from 5,7-difluoro-1-methyl-1,2-dihydrospiro[indole-3,4'-piperidine] (step 3) and ethyl 2-(5-{[tert-butyl(dimethyl)silyl]oxy}-2-chlorobenzyl)acrylate (step 2 of example 30):

$^1$H-NMR (CDCl$_3$) δ 7.17 (1H, d, J=8.6 Hz), 6.70-6.58 (3H, m), 6.56 (1H, d, J=8.6 Hz), 4.15-4.03 (2H, m), 3.16 (2H, s), 3.06-2.69 (6H, m), 2.89 (3H, s), 2.48-2.43 (1H, m), 2.18-2.01 (2H, m), 1.82-1.63 (4H, m), 1.18 (3H, t, J=7.2 Hz), 0.96 (9H, s), 0.17 (6H, s); MS (ESI) 593 (M+H)$^+$.

Step 5. 2-(2-Chloro-5-hydroxybenzyl)-3-(5,7-difluoro-1-methyl-1,2-dihydro-1'H-spiro[indole-3,4'-piperidin]-1'-yl)propanoic acid The title compound was prepared according to the procedure described in step 4 of example 30 from ethyl 2-(5-{[tert-butyl(dimethyl)silyl]oxy}-2-chlorobenzyl)-3-(5,7-difluoro-1-methyl-1,2-dihydro-1'H-spiro[indole-3,4'-piperidin]-1'-yl)propanoate (step 4):

MS (ESI) 451 (M+H)$^+$, 449 (M−H)$^−$.

Example 38

2-(2-Chloro-5-hydroxybenzyl)-3-(1-methyl-2,2-dioxido-1H,1'H-spiro[2,1-benzisothiazole-3,4'-piperidin]-1'-yl)propanoic acid

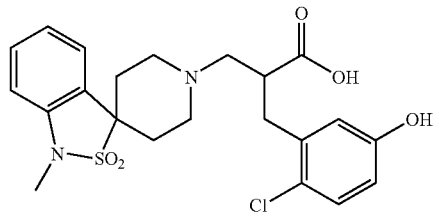

Step 1. 1-Methyl-1,3-dihydro-2,1-benzisothiazole 2,2-dioxide

A mixture of 1,3-dihydro-2,1-benzisothiazole 2,2-dioxide (*J. Heterocyclic Chem.* 1986, 23, 1645., 401 mg, 2.37 mmol), methyl iodide (0.6 mL, 9.48 mmol) and potassium carbonate (328 mg, 2.37 mmol) in N,N-dimethylformamide (7 mL) was stirred for 4 h at room temperature. The reaction mixture was diluted with toluene/ethyl acetate (1/3), then washed with water for two times, and then the organic layer was washed with brine, dried over sodium sulfate, and evaporated. The residue was purified by preparative thin layer chromatography on silica gel developing with hexane/ethyl acetate (2/1) to afford 272 mg (63%) of the title compound as a slight brown syrup:

$^1$H-NMR (CDCl$_3$) δ 7.33-7.17 (2H, m), 7.03-6.95 (1H, m), 6.70 (1H, d, J=7.9 Hz), 4.80 (2H, s), 3.09 (3H, s).

Step 2. Benzyl 1-methyl-1H,1'H-spiro[2,1-benzisothiazole-3,4'-piperidine]-1'-carboxylate 2,2-dioxide To a stirred solution of 1-methyl-1,3-dihydro-2,1-benzisothiazole 2,2-dioxide (step 1, 272 mg, 1.48 mmol) and benzyl bis(2-bromoethyl)carbamate (*Bioorg. Med. Chem. Let.* 1997, 7, 1311., 595 mg, 1.63 mmol) in N,N-dimethylformamide (5 mL) was added 70% sodium hydride in mineral oil (112 mg, 3.27 mmol) at 0° C. and the mixture was stirred for 1 h at the same temperature, then slowly warmed up to room temperature and stirred for 1.5 h at the same temperature. The reaction mixture was diluted with toluene/ethyl acetate (1/3), then washed with water for three times, and then the organic layer was washed with brine, dried over sodium sulfate, and evaporated. The residue was purified by preparative thin layer chromatography on silica gel developing with hexane/ethyl acetate (2/1) to afford 288 mg (50%) of the title compound as a brown syrup:

$^1$H-NMR (CDCl$_3$) δ 7.39-7.29 (7H, m), 7.12-7.01 (2H, m), 6.72 (1H, d, J=7.9 Hz), 5.18 (2H, s), 4.23 (2H, br.m), 3.48 (2H, br.m), 3.13 (3H, s), 2.40-2.35 (2H, m), 2.01 (2H, br.m).

Step 3. 1-Methyl-1H-spiro[2,1-benzisothiazole-3,4'-piperidine] 2,2-dioxide

A mixture of benzyl 1-methyl-1H,1'H-spiro[2,1-benzisothiazole-3,4'-piperidine]-1'-carboxylate 2,2-dioxide (step 2, 288 mg, 0.745 mmol) and 10% palladium on carbon (50 mg) in methanol (10 mL) was stirred under hydrogen atmosphere at room temperature for 8 h. The catalyst was filtered off, and then the filtrate was concentrated to give 201 mg (quant.) of the title compound as a yellow solid:

$^1$H-NMR (CDCl$_3$) δ 7.33-7.23 (2H, m), 7.06-7.02 (1H, m), 6.70 (1H, d, J=7.9 Hz) 3.36-3.20 (4H, m), 3.13 (3H, s), 2.42-2.37 (2H, m), 2.24-2.17 (2H, m); MS (ESI) 253 (M+H)$^+$.

Step 4. Ethyl 2-(5-{[tert-butyl(dimethyl)silyl]oxy}-2-chlorobenzyl)-3-(1-methyl-2,2-dioxido-1H,1'H-spiro[2,1-benzisothiazole-3,4'-piperidin]-1'-yl)propanoate The title compound was prepared according to the procedure described in step 4 of example 4 from 1-methyl-1H-spiro[2,1-benzisothiazole-3,4'-piperidine]2,2-dioxide (step 3) and ethyl 2-(5-{[tert-butyl(dimethyl)silyl]oxy}-2-chlorobenzyl)acrylate (step 2 of example 30):

$^1$H-NMR (CDCl$_3$) δ 7.32-7.27 (1H, m), 7.20-7.16 (2H, m), 7.04-6.99 (1H, m), 6.71-6.62 (3H, m), 4.17-4.05 (2H, m), 3.12 (3H, s), 3.08-2.52 (9H, m), 2.89-2.83 (2H, m), 2.11-2.00 (2H, m), 1.20 (3H, t, J=7.2 Hz), 0.97 (9H, s), 0.18 (6H, s); MS (ESI) 607 (M+H)$^+$.

Step 5. 2-(2-Chloro-5-hydroxybenzyl)-3-(1-methyl-2,2-dioxido-1H,1'H-spiro[2,1-benzisothiazole-3,4'-piperidin]-1'-yl)propanoic acid The title compound was prepared according to the procedure described in step 4 of example 30 from ethyl 2-(5-{[tert-butyl(dimethyl)silyl]oxy}-2-chlorobenzyl)-3-(1-methyl-2,2-dioxido-1H,1'H-spiro[2,1-benzisothiazole-3,4'-piperidin]-1'-yl)propanoate (step 4):

MS (ESI) 465 (M+H)$^+$, 463 (M–H)$^-$.

Example 39

3-(6-Fluoro-1'H,3H-spiro[2-benzofuran-1,4'-piperidin]-1'-yl)-2-[3-(hydroxymethyl)benzyl]propanoic acid trifluoroacetate

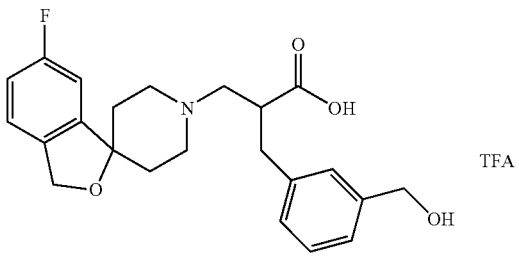

Step 1. {[3-(Bromomethyl)benzyl]oxy}(tert-butyl)dimethylsilane

To a mixture of [3-({[tert-butyl(dimethyl)silyl]oxy}methyl)phenyl]methanol (*J. Med. Chem.* 1996, 25, 4871., 4.39 g, 17 mmol) and carbon tetrabromide (8.95 g, 27 mmol) in tetrahydrofuran (60 mL) was added triphenylphosphine (6.82 g, 26 mmol) in two portions at 0° C. and the mixture was stirred for 3 h at room temperature. The mixture was neutralized with aqueous sodium hydrogen carbonate and extracted with dichloromethane. The organic layer was concentrated. The residue was taken up in hexane and the resulting mixture was filtered, and concentrated. The residue was purified by column chromatography on silica gel eluting with hexane/dichloromethane (10/1) to afford 760 mg (14%) of the title compound as a colorless oil:

$^1$H-NMR (CDCl$_3$) δ 7.40-7.20 (4H, m), 4.72 (2H, s), 4.49 (2H, s), 0.93 (9H, s), 0.09 (6H, s).

Step 2. tert-Butyl 3-(6-fluoro-1'H,3H-spiro[2-benzofuran-1,4'-piperidin]-1'-yl)propanoate The title compound was prepared according to the procedure described in step 1 of example 1 from 6-fluoro-3H-spiro[2-benzofuran-1,4'-piperidine] (*J. Med. Chem.* 1995, 38, 2009.):

$^1$H-NMR (CDCl$_3$) δ 7.14 (1H, dd, J=8.3, 5.0 Hz), 6.96 (1H, dt, J=8.3, 2.4 Hz), 6.80 (1H, dd, J=8.4, 2.2 Hz), 5.02 (2H, s), 2.90-2.70 (4H, m), 2.55-2.35 (4H, m), 2.00-1.70 (4H, m), 1.47 (9H, s).

Step 3. tert-Butyl 2-[3-{[tert-butyl(dimethyl)silyl]oxy}methyl)benzyl]-3-(6-fluoro-1'H,3H-spiro[2-benzofuran-1,4'-piperidin]-1'-yl)propanoate The title compound was prepared according to the procedure described in step 2 of example 1 from {[3-(bromomethyl)benzyl]oxy}(tert-butyl)dimethylsilane (step 1) and tert-butyl 3-(6-fluoro-1'H,3H-spiro[2-benzofuran-1,4'-piperidin]-1'-yl)propanoate (step 2):

$^1$H-NMR (CDCl$_3$) δ 7.30-7.02 (5H, m), 6.98-6.88 (1H, m), 6.80-6.72 (1H, m), 4.99 (2H, s), 4.69 (2H, s), 2.95-2.60 (6H, m), 2.55-2.25 (3H, m), 1.95-1.65 (4H, m), 1.34 (9H, s), 0.92 (9H, s), 0.08 (6H, s); MS (ESI) 570 (M+H)$^+$.

Step 4. 3-(6-Fluoro-1'H,3H-spiro[2-benzofuran-1,4'-piperidin]-1'-yl)-2-[3-(hydroxymethyl)benzyl]propanoic acid trifluoroacetate The title compound was prepared according to the procedure described in step 3 of example 1 from tert-butyl 2-[3-({[tert-butyl(dimethyl)silyl]oxy}methyl)benzyl]-3-(6-fluoro-1'H,3H-spiro[2-benzofuran-1,4'-piperidin]-1'-yl)propanoate (step 3):
MS (ESI) 400 (M+H)$^+$.

Example 40

2-(2-Chloro-4-hydroxybenzyl)-3-(1'H,3H-spiro[2-benzofuran-1,4'-piperidin]-1'-yl)propanoic acid

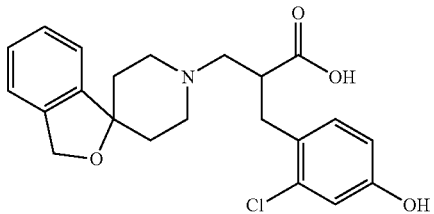

Step 1. tert-Butyl 2-(2-chloro-4-hydroxybenzyl)-3-(1'H,3H-spiro[2-benzofuran-1,4'-piperidin]-1'-yl)propanoate The title compound was prepared according to the procedure described in step 1 of example 15 from tert-butyl 2-(4-{[tert-butyl(dimethyl)silyl]oxy}-2-chlorobenzyl)-3-(1'H,3H-spiro[2-benzofuran-1,4'-piperidin]-1'-yl)propanoate (step 3 of example 13):
$^1$H-NMR (CDCl$_3$) δ 7.32-7.16 (3H, m), 7.12-6.98 (2H, m), 6.64 (1H, d, J=2.6 Hz), 6.47 (1H, dd, J=8.4, 2.6 Hz), 5.06 (2H, s), 3.10-2.75 (6H, m), 2.63-2.42 (3H, m), 2.10-1.82 (2H, m), 1.80-1.67 (2H, m), 1.43 (9H, s); MS (ESI) 458, 460 (M+H)$^+$, 456, 458 (M−H)$^−$.

Step 2. 2-(2-Chloro-4-hydroxybenzyl)-3-(1'H,3H-spiro[2-benzofuran-1,4'-piperidin]-1'-yl)propanoic acid The title compound was prepared according to the procedure described in step 2 of example 15 from tert-butyl 2-(2-chloro-4-hydroxybenzyl)-3-(1'H,3H-spiro[2-benzofuran-1,4'-piperidin]-1'-yl)propanoate (step 1):
$^1$H-NMR (DMSO-d$_6$) δ 9.71 (1H, br.s), 7.33-7.18 (4H, m), 7.11 (1H, d, J=8.1 Hz), 6.83-6.76 (1H, m), 6.70-6.62 (1H, m), 4.95 (2H, s), 2.93-2.62 (6H, m), 2.55-2.20 (3H, m), 1.90-1.73 (2H, m), 1.67-1.52 (2H, m).

Example 41

2-(2-Chloro-5-hydroxybenzyl)-3-[3-(hydroxymethyl)-2,3-dihydro-1'H-spiro[indene-1,4'-piperidin]-1'-yl]propanoic acid and 2-(2-chloro-5-hydroxybenzyl)-3-(3-hydroxy-2,3-dihydro-1'H-spiro[indene-1,4'-piperidin]-1'-yl)propanoic acid

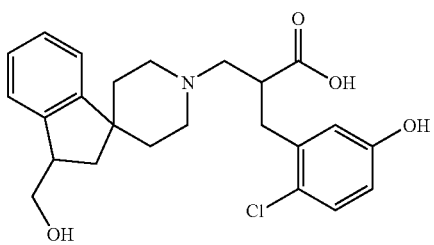

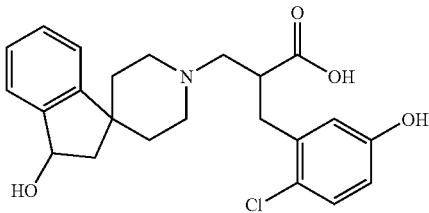

Step 1. Ethyl 3-oxo-2,3-dihydro-1'H-spiro[indene-1,4'-piperidine]-1'-carboxylate To a stirred suspension of spiro[indene-1,4'-piperidin]-3(2H)-one hydrochloride (WO9937642, 592 mg, 2.5 mmol) in dichloromethane (20 mL) were added triethylamine (1.04 mL, 7.5 mmol) and ethyl chloroformate (0.29 mL, 3.0 mmol) at 0° C. and the mixture was stirred for 6 h at the room temperature. The reaction was quenched by the addition of 10% citric acid aqueous solution (50 mL). The aqueous layer was extracted with ethyl acetate (200 mL), and the combined organic layers were washed with saturated sodium bicarbonate aqueous solution (50 mL) and brine (100 mL), dried over sodium sulfate, and evaporated to afford 672 mg (99%) of the title compounds as a colorless oil:
$^1$H-NMR (CDCl$_3$) δ 7.77-7.74 (1H, m), 7.68-7.63 (1H, m), 7.51-7.48 (1H, m), 7.45-7.40 (1H, m), 4.34-4.23 (2H, m), 4.19 (2H, q, J=7.1 Hz), 2.91 (2H, br.t, J=12.9 Hz), 2.65 (2H, s), 2.00 (2H, dt, J=12.8, 4.2 Hz), 1.53 (2H, br.d, J=12.7 Hz), 1.30 (3H, t, J=7.2 Hz); MS (ESI) 274 (M+H)$^+$.

Step 2. 2,3-Dihydrospiro[indene-1,4'-piperidin]-3-ylmethanol and 2,3-dihydrospiro[indene-1,4'-piperidin]-3-ol To a stirred mixture of (methoxymethyl)triphenylphosphonium chloride (2.1 g, 6.1 mmol) and potassium tert-butoxide (689 mg, 6.1 mmol) in 1,4-dioxane (50 mL) was added a solution of ethyl 3-oxo-2,3-dihydro-1'H-spiro[indene-1,4'-piperidine]-1'-carboxylate (670 mg, 2.5 mmol) in 1,4-diaxane (50 mL) at room temperature and the mixture was stirred for 36 h at the same temperature. The mixture was quenched by the addition of water (100 mL). 1,4-Dioxane was removed under reduced pressure. The aqueous layer was extracted with ethyl acetate (200 mL), and the organic layer was washed with brine (50 mL), dried over sodium sulfate, and evaporated. The residue was purified by column chromatography on silica gel (200 g) eluting with hexane/ethyl acetate (10/1 to 2/1) to afford a colorless oil (680 mg).

This oil was dissolved in acetone (25 mL). To the solution was added concentrated hydrochloric acid (0.5 mL) and the mixture was refluxed for 3 h. After cooling to the room temperature, the mixture was basified by addition of saturated sodium bicarbonate aqueous solution. The mixture was extracted with ethyl acetate (250 mL). The organic layer was washed with brine (50 mL), dried over sodium sulfate, and evaporated to afford a yellow oil (682 mg).

This oil was dissolved in methanol (10 mL). To the solution was added sodium borohydride (103 mg, 2.7 mmol) at 0° C. and the mixture was stirred for 3 h at the room temperature. The reaction was quenched by the addition of water (30 mL). The mixture was extracted with ethyl acetate (200 mL), and the organic layer was washed with 10% citric acid aqueous solution (20 mL) and saturated sodium bicarbonate aqueous solution (20 mL), dried over sodium sulfate, and evaporated. The residue was purified by column chromatography on silica gel (40 g) eluting with hexane/ethyl acetate (1/1) to afford a colorless oil (257 mg).

This oil was dissolved in ethanol. To the solution was added 5 N sodium hydroxide aqueous solution (1.8 mL) at the room temperature and the reaction mixture was refluxed for 20 h. After cooling to the room temperature, ethanol was removed under reduced pressure. The aqueous layer was extracted with dichloromethane (100 mL×2). The combined organic layers were dried over sodium sulfate, and evaporated to afford 205 mg of mixture of title compounds as a colorless oil:

MS (ESI) 218 and 204 (M+H)$^+$.

Step 3. Ethyl 2-(5-{[tert-butyl(dimethyl)silyl]oxy}-2-chlorobenzyl)-3-[3-(hydroxymethyl)-2,3-dihydro-1'H-spiro[indene-1,4'-piperidin]-1'-yl]propanoate and ethyl 2-(5-{[tert-butyl(dimethyl)silyl]oxy}-2-chlorobenzyl)-3-(3-hydroxy-2,3-dihydro-1'H-spiro[indene-1,4'-piperidin]-1'-yl)propanoate The mixture of title compounds were prepared according to the procedure described in step 4 of example 4 from 2,3-dihydrospiro[indene-1,4'-piperidin]-3-ylmethanol and 2,3-dihydrospiro[indene-1,4'-piperidin]-3-ol (step 2) and ethyl 2-(5-{[tert-butyl(dimethyl)silyl]oxy}-2-chlorobenzyl)acrylate (step 2 of example 30):

MS (ESI) 572 and 558 (M+H)$^+$.

Step 4. 2-(2-Chloro-5-hydroxybenzyl)-3-[3-(hydroxymethyl)-2,3-dihydro-1'H-spiro[indene-1,4'-piperidin]-1'-yl]propanoic acid and 2-(2-chloro-5-hydroxybenzyl)-3-(3-hydroxy-2,3-dihydro-1'H-spiro[indene-1,4'-piperidin]-1'-yl)propanoic acid The mixture of title compounds were prepared according to the procedure described in step 4 of example 30 from ethyl 2-(5-{[tert-butyl(dimethyl)silyl]oxy}-2-chlorobenzyl)-3-[3-(hydroxymethyl)-2,3-dihydro-1'H-spiro[indene-1,4'-piperidin]-1'-yl]propanoate and ethyl 2-(5-{[tert-butyl(dimethyl)silyl]oxy}-2-chlorobenzyl)-3-(3-hydroxy-2,3-dihydro-1'H-spiro[indene-1,4'-piperidin]-1'-yl)propanoate (step 3):

MS (ESI) 430 and 416 (M+H)$^+$, 428 and 414 (M−H)$^−$.

Example 42

2-(2-Chloro-5-hydroxybenzyl)-3-(5-fluoro-1'H,3H-spiro[2-benzofuran-1,4'-piperidin]-1'-yl)propanoic acid

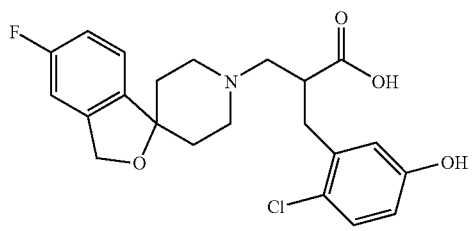

Step 1. Ethyl 2-(5-{[tert-butyl(dimethyl)silyl]oxy}-2-chlorobenzyl)-3-(5-fluoro-1'H,3H-spiro[2-benzofuran-1,4'-piperidin]-1'-yl)propanoate The title compound was prepared according to the procedure described in step 4 of example 4 from 5-fluoro-3H-spiro[2-benzofuran-1,4'-piperidine] (WO 2002088089) and ethyl 2-(5-{[tert-butyl(dimethyl)silyl]oxy}-2-chlorobenzyl)acrylate (step 2 of example 30):

$^1$H-NMR (CDCl$_3$) δ 7.18 (1H, d, J=8.6 Hz), 7.08-6.83 (3H, m), 6.72 (1H, d, J=2.8 Hz), 6.64 (1H, dd, J=8.6, 2.8 Hz), 5.01 (2H, s), 4.18-4.00 (2H, m), 3.15-2.97 (2H, m), 2.93-2.70 (4H, m), 2.58-2.30 (3H, m), 1.95-1.78 (2H, m), 1.77-1.63 (2H, m), 1.19 (3H, t, J=7.1 Hz), 0.97 (9H, s), 0.18 (6H, s); MS (ESI) 562 (M+H)$^+$.

Step 2. 2-(2-Chloro-5-hydroxybenzyl)-3-(5-fluoro-1'H,3H-spiro[2-benzofuran-1,4'-piperidin]-1'-yl)propanoic acid The title compound was prepared according to the procedure described in step 4 of example 30 from ethyl 2-(5-{[tert-butyl(dimethyl)silyl]oxy}-2-chlorobenzyl)-3-(5-fluoro-1'H,3H-spiro[2-benzofuran-1,4'-piperidin]-1'-yl)propanoate (step 1):

MS (ESI) 420 (M+H)$^+$, 418 (M−H)$^−$.

Example 43

2-[2-(Ethoxycarbonyl)benzyl]-3-(1'H,3H-spiro[2-benzofuran-1,4'-piperidin]-1'-yl)propanoic acid trifluoroacetate

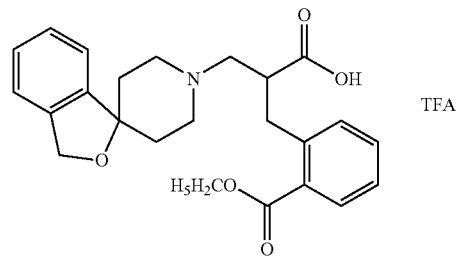

Step 1. Ethyl 2-[3-tert-butoxy-3-oxo-2-(1'H,3H-spiro[2-benzofuran-1,4'-piperidin]-1'-ylmethyl)propyl]benzoate The title compound was prepared according to the procedure described in step 2 of example 1 from tert-butyl 3-(1'H,3H-spiro[2-benzofuran-1,4'-piperidin]-1'-yl)propanoate (WO 2003064425) and ethyl 2-(bromomethyl)benzoate (J. Org. Chem. 1985, 50, 2128.):

$^1$H-NMR (CDCl$_3$) δ 7.93-7.89 (1H, m), 7.41-7.36 (1H, m), 7.29-7.18 (5H, m), 7.11-7.08 (1H, m), 5.05 (2H, s), 4.37 (2H, q, J=7.2 Hz), 3.36-3.32 (1H, m), 3.03-2.87 (3H, m), 2.79-2.72 (2H, m), 2.54-2.45 (2H, m), 2.40-2.31 (1H, m), 1.95-1.82 (2H, m), 1.75-1.68 (2H, m), 1.41 (3H, t, J=7.2 Hz), 1.34 (9H, s); MS (ESI) 480 (M+H)$^+$.

Step 2. 2-[2-(Ethoxycarbonyl)benzyl]-3-(1'H,3H-spiro[2-benzofuran-1,4'-piperidin]-1'-yl)propanoic acid trifluoroacetate The title compound was prepared according to the procedure described in step 3 of example 1 from ethyl 2-[3-tert-butoxy-3-oxo-2-(1'H,3H-spiro[2-benzofuran-1,4'-piperidin]-1'-ylmethyl)propyl]benzoate (step 1):
$^1$H-NMR (CDCl$_3$) δ 8.04 (1H, d, J=7.7 Hz), 7.51 (1H, t, J=7.5 Hz), 7.41-7.21 (5H, m), 7.11-7.09 (1H, m), 5.08 (2H, s), 4.37 (2H, q, J=7.2 Hz), 3.79-3.65 (3H, m), 3.53-3.16 (5H, m), 2.43-2.25 (2H, m), 1.96-1.88 (2H, m), 1.41 (3H, t, J=7.1 Hz); MS (ESI) 424 (M+H)$^+$, 422 (M−H)$^−$.

Example 44

3-(6-Fluoro-1'H,3H-spiro[2-benzofuran-1,4'-piperidin]-1'-yl)-2-(1,3-thiazol-4-ylmethyl)propanoic acid trifluoroacetate

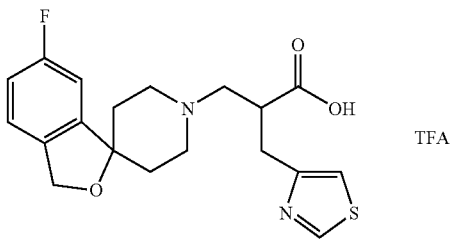

Step 1. tert-Butyl 2-(diethoxyphosphoryl)-3-(1,3-thiazol-4-yl)propanoate

A mixture of 4-methylthiazol (5.85 g, 59 mmol), N-bromosccinimide (11 g, 62 mmol) and 2,2'-azobisisobutyronitrile (968 mg, 5.9 mmol) in carbontetrachloride (200 mL) was refluxed for 5 h. After cooling, the mixture was filtered. To the filtrate was added toluene (100 mL) and the mixture was concentrated to afford a toluene solution of 4-(bromomethyl)-1,3-thiazole (27 g).
To a solution of tert-butyl diethylphosphonoacetate (15.6 g, 62 mmol) in dimethylformamide (50 mL) was added sodiumhydride (60% dispersion in mineral oil, 2.48 g, 62 mmol) at 0° C. under nitrogen atmosphere. After 45 min, to the mixture was added a solution of 4-(bromomethyl)-1,3-thiazole in toluene (27 g). The mixture was stirred at room temperature overnight. The mixture was quenched with water and extracted with toluene/ethyl acetate (1/3). The combined organic layer was washed with brine, dried over sodium sulfate, and evaporated. The residue was purified by column chromatography on silica gel eluting with hexane/ethyl acetate (1/2 to 100% ethyl acetate) to afford 7.17 g (35%) of the title compound as a colorless oil:
$^1$H-NMR (CDCl$_3$) δ 8.74 (1H, d, J=2.0 Hz), 7.06 (1H, d, J=1.8 Hz), 4.24-4.08 (4H, m), 3.55-3.24 (3H, m), 1.45-1.30 (15H, m).

Step 2. tert-Butyl 2-(1,3-thiazol-4-ylmethyl)acrylate

To a stirred solution of tert-butyl 2-(diethoxyphosphoryl)-3-(1,3-thiazol-4-yl)propanoate (step 1, 7.17 g, 20.5 mmol) in tetrahydrofran (100 mL) was added sodiumhydride (60% dispersion in mineral oil, 820 mg, 20.5 mmol) at 0° C. under nitrogen. After 10 min, to the mixture was added paraformaldehyde (1.85 g, 61.5 mmol) and the mixture was stirred at room temperature for 45 min. The mixture was quenched with aqueous sodium hydrogen carbonate and extracted with ethyl acetate. The combined organic layer was washed with brine, dried over sodium sulfate, and evaporated. The residue was purified by column chromatography on silica gel eluting with hexane/ethyl acetate (3/1) to afford 4.25 g (92%) of the title compound as a colorless oil:
$^1$H-NMR (CDCl$_3$) δ 8.77 (1H, d, J=2.0 Hz), 7.04 (1H, d, J=2.0 Hz), 6.23-6.20 (1H, m), 5.52 (1H, q, J=1.3 Hz), 3.83 (2H, s), 1.44 (9H, s); MS (ESI) 226 (M+H)$^+$.

Step 3. tert-Butyl 3-(6-fluoro-1'H,3H-spiro[2-benzofuran-1,4'-piperidin]-1'-yl)-2-(1,3-thiazol-4-ylmethyl)propanoate The title compound was prepared according to the procedure described in step 4 of example 4 from 6-fluoro-3H-spiro[2-benzofuran-1,4'-piperidine] (J. Med. Chem. 1995, 38, 2009.) and tert-butyl 2-(1,3-thiazol-4-ylmethyl)acrylate (step 2):
$^1$H-NMR (CDCl$_3$) δ 8.75 (1H, d, J=2.0 Hz), 7.13 (1H, dd, J=8.3, 4.8 Hz), 7.03 (1H, d, J=2.0 Hz), 6.95 (1H, dt, J=9.0, 2.4 Hz), 6.77 (1H, dd, J=8.3, 2.2 Hz), 5.01 (2H, br.s), 3.14-2.99 (3H, m), 2.90-2.84 (1H, m), 2.84-2.65 (2H, m), 2.56-2.28 (3H, m), 1.95-1.66 (4H, m), 1.39 (9H, s); MS (ESI) 433 (M+H)$^+$.

Step 4. 3-(6-Fluoro-1'H,3H-spiro[2-benzofuran-1,4'-piperidin]-1'-yl)-2-(1,3-thiazol-4-ylmethyl)propanoic acid trifluoroacetate The title compound was prepared according to the procedure described in step 3 of example 1 from tert-Butyl 3-(6-fluoro-1'H,3H-spiro[2-benzofuran-1,4'-piperidin]-1'-yl)-2-(1,3-thiazol-4-ylmethyl)propanoate (step 3):
$^1$H-NMR (DMSO-d$_6$) δ 9.09 (1H, s), 7.48 (1H, s), 7.38-7.30 (1H, m), 7.22-7.10 (1H, m), 7.05-6.95 (1H, m), 4.99 (2H, br.s), 3.95-3.10 (9H, m), 2.28-2.10 (2H, m), 1.93-1.78 (2H, m); MS (ESI) 377 (M+H)$^+$, 375 (M−H)$^−$.

Example 45

2-(2-Chloro-5-hydroxybenzyl)-3-[3-(hydroxymethyl)-1'H,3H-spiro[2-benzofuran-1,4'-piperidin]-1'-yl]propanoic acid

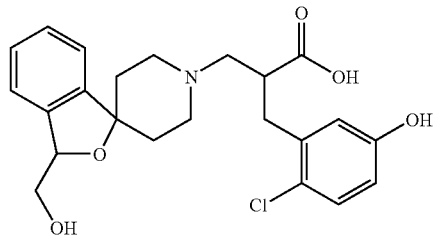

Step 1. 1-(2-Bromophenyl)ethane-1,2-diol

To a stirred solution of 1-bromo-2-vinylbenzene (4.14 g, 22.6 mmol) and 4-methylmorpholine N-oxide in acetonitrile (20 mL) and water (10 mL) was added a 2.5% solution of osmium tetroxide in 2-methyl-2-propanol (2 mL) at room temperature and the mixture was stirred for 24 h at the same temperature. The reaction mixture was quenched by the addition of sodium hydrosulfate, and diluted with water, then extracted with ethyl acetate. The organic layer was washed with diluted hydrochloric acid aqueous solution and brine, dried over sodium sulfate, and evaporated to afford 5.01 g (quant.) of the title compound as a brown solid:
$^1$H-NMR (CDCl$_3$) δ 7.53 (1H, d, J=7.7 Hz), 7.41 (1H, d, J=8.1 Hz), 7.26-7.21 (1H, m), 7.06-7.00 (1H, m), 5.02 (1H, m), 3.76-3.72 (1H, m), 3.40-3.33 (1H, m).

Step 2. 1-(2-Bromophenyl)-2-1{[tert-butyl(diphenyl)silyl]oxy}ethanol

To a stirred solution of 1-(2-bromophenyl)ethane-1,2-diol (step 1, 5.01 g, 22.6 mmol) and in dichloromethane (20 mL) and imidazole (2.31 g, 33.9 mmol) in N,N-dimethylformamide (20 mL) was added tert-butyldiphenylsilyl chloride (6.53 g, 23.8 mmol) at 0° C. and the mixture was stirred for 19 h at the same temperature. The reaction mixture was diluted with toluene/ethyl acetate (1/3), then washed with water for three times and brine, dried over sodium sulfate, and evaporated. The residue was purified by column chromatography on silica gel (100 g) eluting with hexane/ethyl acetate (10/1) to afford 7.05 g (68%) of the title compound as a colorless syrup:
$^1$H-NMR (CDCl$_3$) δ 7.70-7.67 (2H, m), 7.61-7.57 (3H, m), 7.47-7.28 (8H, m), 7.14-7.08 (1H, m), 5.21-5.26 (1H, m), 3.98-3.94 (1H, m), 3.57-3.51 (1H, m), 3.17 (1H, d, J=2.9 Hz), 1.03 (9H, s).

Step 3. Ethyl 4-[2-(2-{[tert-butyl(diphenyl)silyl]oxy}-1-hydroxyethyl)phenyl]-4-hydroxypiperidine-1-carboxylate To a stirred solution of 1-(2-bromophenyl)-2-{[tert-butyl(diphenyl)silyl]oxy}ethanol (step 2, 5.63 g, 12.4 mmol) in tetrahydrofuran (36 mL) was added dropwise a 1.59 M solution of butyllithium in tetrahydrofuran (15.9 mL, 25.3 mmol) at −78° C. for 5 min and the mixture was stirred for 5 h at the same temperature. To the mixture was added dropwise a solution of ethyl 4-oxopiperidine-1-carboxylate (2.33 g, 13.6 mmol) in tetrahydrofuran (10 mL) at −78° C. and the mixture was stirred for 2 h at the same temperature. This resulting mixture was slowly warmed up to room temperature and stirred for 16 h at the same temperature. The reaction mixture was quenched by the addition of saturated ammonium chloride aqueous solution, and concentrated to give a yellow residue. The crude material was partitioned between ethyl acetate and water, and then the organic layer was washed with brine, dried over sodium sulfate, and evaporated. The residue was purified by column chromatography on silica gel (150 g) eluting with hexane/ethyl acetate (2/1) to afford 1.76 g (26%) of the title compound as a colorless solid:
$^1$H-NMR (CDCl$_3$) δ 7.57-7.25 (14H, m), 5.72 (1H, m), 4.19-4.08 (2H, m), 3.96-3.75 (2H, m), 3.34-3.14 (1H, m), 1.89-1.72 (2H, m), 1.53-1.43 (3H, m), 1.34-1.23 (2H, m), 1.28 (3H, t, J=6.9 Hz), 1.03 (9H, s).

Step 4. Ethyl 3-{[tert-butyl(diphenyl)silyl]oxy}methyl)-1'H,3H-spiro[2-benzofuran-1,4'-piperidine]-1'-carboxylate To a stirred solution of ethyl 4-[2-(2-{[tert-butyl(diphenyl)silyl]oxy}-1-hydroxyethyl)phenyl]-4-hydroxypiperidine-1-carboxylate (step 3, 1.76 g, 3.21 mmol) and triethylamine (1.34 mL, 9.64 mmol) in dichloromethane (15 mL) was added dropwise methanesulfonyl chloride (552 mg, 4.82 mmol) at 0° C. for 5 min. This resulting mixture was slowly warmed up to room temperature and stirred for 18 h at the same temperature, then 50° C. for 2 h. The reaction mixture was washed with water, dried over sodium sulfate, and evaporated. The residue was purified by column chromatography on silica gel (100 g) eluting with hexane/ethyl acetate (5/1) to afford 1.39 g (79%) of the title compound as a colorless syrup:
$^1$H-NMR (CDCl$_3$) δ 7.65-7.61 (4H, m), 7.45-7.23 (9H, m), 7.10-7.05 (1H, m), 5.32 (1H, t, J=4.6 Hz), 4.20-4.04 (4H, m), 3.94-3.84 (2H, m), 3.23 (2H, br.m), 2.04-1.66 (4H, m), 1.28 (3H, t, J=6.4 Hz), 0.99 (9H, s).

Step 5. 3H-Spiro[2-benzofuran-1,4'-piperidin]-3-ylmethanol

A solution of ethyl 3-({[tert-butyl(diphenyl)silyl]oxy}methyl)-1'H,3H-spiro[2-benzofuran-1,4'-piperidine]-1'-carboxylate (step 4, 1.39 g, 2.63 mmol) in 5 M sodium hydroxide aqueous solution (10 mL) and ethanol (10 mL) was refluxed for 40 h. The reaction mixture was concentrated to give a brown residue. The crude material was partitioned between diethyl ether and water, and the organic layer was washed with brine, dried over sodium sulfate, and evaporated to afford 100 mg (17%) of the title compound as a colorless solid:
MS (ESI) 220 (M+H)$^+$.

Step 6. Ethyl 2-(5-{[tert-butyl(dimethyl)silyl]oxy}-2-ch-3-[3-(hydroxymethyl)-1'H,3H-spiro[2-benzofuran-1,4'-piperidin]-1'-yl]propanoate lorobenzyl)

The title compounds were prepared according to the procedure described in step 4 of example 4 from 3H-spiro[2-benzofuran-1,4'-piperidin]-3-ylmethanol (step 5) and ethyl 2-(5-{[tert-butyl(dimethyl)silyl]oxy}-2-chlorobenzyl)acrylate (step 2 of example 30):
$^1$H-NMR (CDCl$_3$) δ 7.31-7.10 (5H, m), 6.71 (1H, d, J=2.8 Hz), 6.64 (1H, dd, J=8.6, 2.8 Hz), 5.27 (1H, m), 4.19-4.00 (2H, m), 3.95-3.90 (1H, m), 3.76-3.63 (1H, m), 3.12-2.99 (2H, m), 2.88-2.76 (4H, m), 2.55-2.39 (3H, m), 2.09-1.80 (2H, m), 1.71-1.66 (2H, m), 1.18 (3H, t, J=7.2 Hz), 0.96 (9H, s), 0.17 (6H, s); MS (ESI) 574 (M+H)$^+$.

Step 7. 2-(2-Chloro-5-hydroxybenzyl)-3-[3-(hydroxymethyl)-1'H,3H-spiro[2-benzofuran-1,4'-piperidin]-1'-yl]propanoic acid The title compound was prepared according to the procedure described in step 4 of example 30 from ethyl 2-(5-{[tert-butyl(dimethyl)silyl]oxy}-2-chlorobenzyl)-3-[3-(hydroxymethyl)-1'H,3H-spiro[2-benzofuran-1,4'-piperidin]-1'-yl]propanoate (step 6):
MS. (ESI) 432 (M+H)$^+$, 430 (M−H)$^−$.

Example 46

3-(5-Fluoro-1-methyl-2-oxo-1,2-dihydro-1'H-spiro[indole-3,4'-piperidin]-1'-yl)-2-(pyridin-2-ylmethyl)propanoic acid

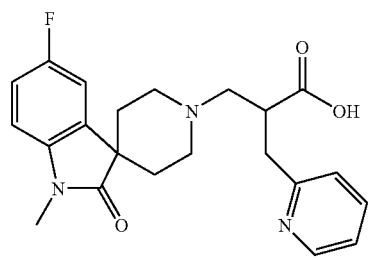

Step 1. Ethyl 3-(5-fluoro-1-methyl-2-oxo-1,2-dihydro-1'H-spiro[indole-3,4'-piperidin]-1'-yl)-2-(pyridin-2-ylmethyl)propanoate The title compound was prepared according to the procedure described in step 4 of example 4 from 5-fluoro-1- methylspiro[indole-3,4'-piperidin]-2(1H)-one (step 3 of example 6) and ethyl 2-(pyridin-2-ylmethyl)acrylate (*Polym. J.* 2000, 32, 173.):

$^1$H-NMR (CDCl$_3$) δ 8.57-8.51 (1H, m), 7.64-7.54 (1H, m), 7.22-7.08 (3H, m), 7.02-6.92 (1H, m), 6.74 (1H, dd, J=8.4, 4.3 Hz), 4.18-4.06 (2H, m), 3.38-3.23 (1H, m), 3.17 (3H, s), 3.13-2.82 (5H, m), 2.77-2.54 (3H, m), 1.98-1.85 (2H, m), 1.75-1.60 (2H, m), 1.19 (3H, t, J=7.1 Hz); MS (ESI) 426 (M+H)$^+$.

Step 2. 3-(5-Fluoro-1-methyl-2-oxo-1,2-dihydro-1'H-spiro[indole-3,4'-piperidin]-1'-yl)-2-(pyridin-2-ylmethyl)propanoic acid The title compound was prepared according to the procedure described in step 4 of example 30 from ethyl 3-(5-fluoro-1-methyl-2-oxo-1,2-dihydro-1'H-spiro[indole-3,4'-piperidin]-1'-yl)-2-(pyridin-2-ylmethyl)propanoate (step 1):

$^1$H-NMR (CDCl$_3$) δ 8.57-8.49 (1H, m), 7.65-7.56 (1H, m), 7.34-7.26 (1H, m), 7.19-7.10 (1H, m), 7.04-6.92 (2H, m), 6.80-6.72 (1H, m), 3.62-3.13 (7H, m), 3.17 (3H, s), 2.98-2.82 (2H, m), 2.45-2.25 (2H, m), 1.95-1.75 (2H, m); MS (ESI) 398 (M+H)$^+$.

Example 47

3-(3,3-Dimethyl-1'H,3H-spiro[2-benzofuran-1,4'-piperidin]-1'-yl)-2-(pyridin-2-ylmethyl)propanoic acid

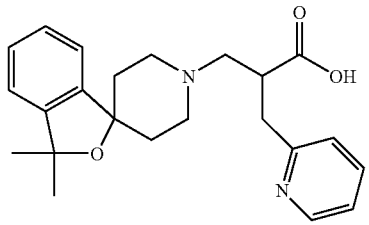

Step 1. Ethyl 3-(3,3-dimethyl-1'H,3H-spiro[2-benzofuran-1,4'-piperidin]-1'-yl)-2-(pyridin-2-ylmethyl)propanoate The title compound was prepared according to the procedure described in step 4 of example 4 from 3,3-dimethyl-3H-spiro[2-benzofuran-1,4'-piperidine] (step 4 of example 34) and ethyl 2-(pyridin-2-ylmethyl)acrylate (*Polym. J.* 2000, 32, 173):

$^1$H-NMR (CDCl$_3$) δ 8.57-8.50 (1H, m), 7.63-7.53 (1H, m), 7.33-7.02 (6H, m), 4.19-4.04 (2H, m), 3.33-3.20 (1H, m), 3.16-2.97 (2H, m), 2.94-2.68 (3H, m), 2.62-2.36 (3H, m), 1.98-1.82 (2H, m), 1.78-1.57 (2H, m), 1.48 (6H, s), 1.18 (3H, t, J=7.1 Hz); MS (ESI) 409 (M+H)$^+$.

Step 2. 3-(3,3-Dimethyl-1'H,3H-spiro[2-benzofuran-1,4'-piperidin]-1'-yl)-2-(pyridin-2-ylmethyl)propanoic acid The title compound was prepared according to the procedure described in step 2 of example 33 from ethyl 3-(3,3-dimethyl-1'H,3H-spiro[2-benzofuran-1,4'-piperidin]-1'-yl)-2-(pyridin-2-ylmethyl)propanoate (step 1):

$^1$H-NMR (CDCl$_3$) δ 8.56-8.48 (1H, m), 7.70-7.59 (1H, m), 7.40-7.23 (3H, m), 7.21-7.02 (3H, m), 3.58-3.44 (2H, m), 3.43-2.83 (7H, m), 2.48-2.28 (2H, m), 1.83-1.68 (2H, m), 1.17 (6H, s); MS (ESI) 381 (M+H)$^+$.

Example 48

3-(3-Methyl-1'H,3H-spiro[2-benzofuran-1,4'-piperidin]-1'-yl)-2-(pyridin-2-ylmethyl)propanoic acid

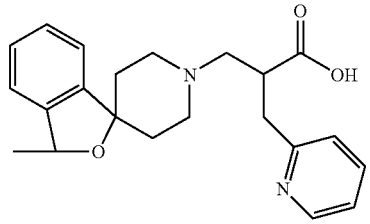

Step 1. Ethyl 3-(3-methyl-1'H,3H-spiro[2-benzofuran-1,4'-piperidin]-1'-yl)-2-(pyridin-2-ylmethyl)propanoate The title compound was prepared as a diastereo mixture according to the procedure described in step 4 of example 4 from 3-methyl-3H-spiro[2-benzofuran-1,4'-piperidine] (step 4 of example 36) and ethyl 2-(pyridin-2-ylmethyl)acrylate (*Polym. J.* 2000, 32, 173.):

$^1$H-NMR (CDCl$_3$) δ 8.57-8.50 (1H, m), 7.63-7.53 (1H, m), 7.33-7.03 (6H, m), 5.27 (1H, q, J=6.4 Hz), 4.21-4.01 (2H, m), 3.35-3.20 (1H, m), 3.16-2.97 (2H, m), 2.95-2.68 (3H, m), 2.62-2.32 (3H, m), 2.08-1.93 (1H, m), 1.88-1.60 (3H, m), 1.48 (3H, d, J=6.4 Hz), 1.27-1.07 (3H, m); MS (ESI) 395 (M+H)$^+$.

Step 2. 3-(3-Methyl-1'H,3H-spiro[2-benzofuran-1,4'-piperidin]-1'-yl)-2-(pyridin-2-ylmethyl)propanoic acid The title compound was prepared as a diastereo mixture according to the procedure described in step 2 of example 33 from ethyl 3-(3-methyl-1'H,3H-spiro[2-benzofuran-1,4'-piperidin]-1'-yl)-2-(pyridin-2-ylmethyl)propanoate (step 1):

MS (ESI) 367 (M+H)$^+$.

Example 49

3-(3-Methyl-1'H,3H-spiro[2-benzofuran-1,4'-piperidin]-1'-yl)-2-(1,3-thiazol-4-ylmethyl)propanoic acid trifluoroacetate

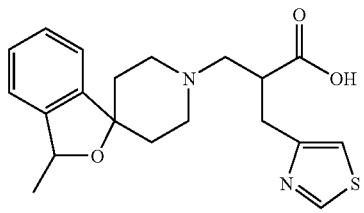

Step 1. tert-Butyl 3-(3-Methyl-1'H,3H-spiro[2-benzofuran-1,4'-piperidin]-1'-yl)-2-(1,3-thiazol-4-ylmethyl)propanoate The title compound was prepared according to the procedure described in step 4 of example 4 from 3-methyl-3H-spiro[2-benzofuran-1,4'-piperidine] (step 4 of example 36) and tert-butyl 2-(1,3-thiazol-4-ylmethyl)acrylate (step 2 of example 44):
$^1$H-NMR (CDCl$_3$) δ 8.75 (1H, d, J=2.0 Hz), 7.31-7.05 (4H, m), 7.03 (1H, d, J=2.0 Hz), 5.28 (1H, q, J=6.4 Hz), 3.16-2.65 (6H, m), 2.62-2.30 (3H, m), 2.12-1.62 (4H, m), 1.49 (3H, d, J=6.4 Hz), 1.39 (9H, s); MS (ESI) 429 (M+H)$^+$.

Step 2. 3-(3-Methyl-1'H,3H-spiro[2-benzofuran-1,4'-piperidin]-1'-yl)-2-(1,3-thiazol-4-ylmethyl)propanoic acid trifluoroacetate The titled compound was prepared according to the procedure described in step 3 of example 1 from tert-butyl 3-(3-methyl-1'H,3H-spiro[2-benzofuran-1,4'-piperidin]-1'-yl)-2-(1,3-thiazol-4-ylmethyl)propanoate (step 1):
MS (ESI) 373 (M+H)$^+$.

Example 50

3-(3,4-Dihydro-1'H-spiro[isochromene-1,4'-piperidin]-1'-yl)-2-(1,3-thiazol-4-ylmethyl)propanoic acid trifluoroacetate

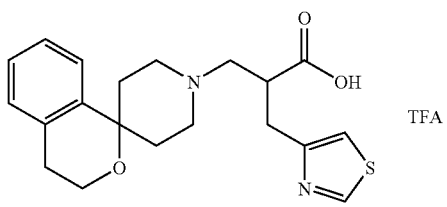

Step 1. tert-Butyl 3-(3,4-dihydro-1'H-spiro[isochromene-1,4'-piperidin]-1'-yl)-2-(1,3-thiazol-4-ylmethyl)propanoate The title compound was prepared according to the procedure described in step 4 of example 4 from 3,4-dihydrospiro[isochromene-1,4'-piperidine] (WO 9528389) and tert-butyl 2-(1,3-thiazol-4-ylmethyl)acrylate (step 2 of example 44):
$^1$H-NMR (CDCl$_3$) δ 8.75 (1H, d, J=2.0 Hz), 7.25-7.05 (4H, m), 7.03 (1H, d, J=2.0 Hz), 3.89 (2H, t, J=5.5 Hz), 3.17-3.03 (3H, m), 2.90-2.62 (3H, m), 2.82 (2H, t, J=5.5 Hz), 2.57-2.30 (3H, m), 2.05-1.75 (4H, m), 1.40 (9H, s); MS (ESI) 429 (M+H)$^+$.

Step 2. 3-(3,4-Dihydro-1'H-spiro[isochromene-1,4'-piperidin]-1'-yl)-2-(1,3-thiazol-4-ylmethyl)propanoic acid trifluoroacetate The title compound was prepared according to the procedure described in step 3 of example 1 from tert-butyl 3-(3,4-dihydro-1'H-spiro[isochromene-1,4'-piperidin]-1'-yl)-2-(1,3-thiazol-4-ylmethyl)propanoate (step 1):

Example 51

3-(5-Fluoro-1'H,3H-spiro[2-benzofuran-1,4'-piperidin]-1'-yl)-2-(1,3-thiazol-4-ylmethyl)propanoic acid trifluoroacetate

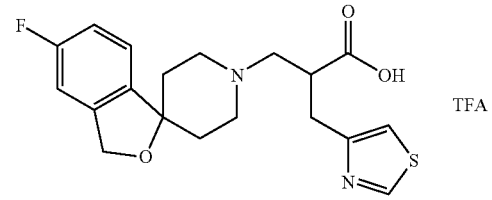

Step 1. tert-Butyl 3-(5-fluoro-1'H,3H-spiro[2-benzofuran-1,4'-piperidin]-1'-yl)-2-(1,3-thiazol-4-ylmethyl)propanoate The title compound was prepared according to the procedure described in step 4 of example 4 from 5-fluoro-3H-spiro[2-benzofuran-1,4'-piperidine] and tert-butyl 2-(1,3-thiazol-4-ylmethyl)acrylate (step 2 of example 44):
$^1$H-NMR (CDCl$_3$) δ 8.75 (1H, d, J=2.0 Hz), 7.07-6.85 (4H, m), 5.02 (2H, s), 3.17-3.02 (3H, m), 2.97-2.85 (1H, m), 2.83-2.67 (2H, m), 2.56-2.30 (3H, m), 1.95-1.80 (2H, m), 1.78-1.65 (2H, m), 1.38 (9H, s); MS (ESI) 433 (M+H)$^+$.

Step 2. 3-(5-Fluoro-1'H,3H-spiro[2-benzofuran-1,4'-piperidin]1'-yl)-2-(1,3-thiazol-4-ylmethyl)propanoic acid trifluoroacetate The title compound was prepared according to the procedure described in step 3 of example 1 from tert-butyl 3-(5-fluoro-1'H,3H-spiro[2-benzofuran-1,4'-piperidin]-1'-yl)-2-(1,3-thiazol-4-ylmethyl)propanoate (step 1):
MS (ESI) 377 (M+H)$^+$.

Example 52

3-(7-Fluoro-1'H,3H-spiro[2-benzofuran-1,4'-piperidin]-1'-yl)-2-(1,3-thiazol-4-ylmethyl)propanoic acid trifluoroacetate

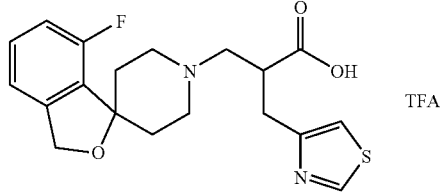

Step 1. tert-Butyl 3-(7-fluoro-1'H,3H-spiro[2-benzofuran-1,4'-piperidin]-1'-yl)-2-(1,3-thiazol-4-ylmethyl)propanoate The title compound was prepared according to the procedure described in step 4 of example 4 from 7-fluoro-3H-spiro[2-benzofuran-1,4'-piperidine] (J. Med. Chem. 1995, 38, 2009.) and tert-butyl 2-(1,3-thiazol-4-ylmethyl)acrylate (step 2 of example 44):
$^1$H-NMR (CDCl$_3$) δ 8.75 (1H, d, J=2.0 Hz), 7.26-7.17 (1H, m), 7.03 (1H, d, J=2.0 Hz), 6.99-6.85 (2H, m), 5.07 (2H, s), 3.17-2.90 (4H, m), 2.82-2.66 (2H, m), 2.55-2.15 (5H, m), 1.80-1.66 (2H, m), 1.39 (9H, s); MS (ESI) 433 (M+H)$^+$.

Step 2. 3-(7-Fluoro-1'H,3H-spiro[2-benzofuran-1,4'-piperidin]-1'-yl)-2-(1,3-thiazol-4-ylmethyl)propanoic acid trifluoroacetate The title compound was prepared according to the procedure described in step 3 of example 1 from tert-butyl 3-(7-fluoro-1'H,3H-spiro[2-benzofuran-1,4'-piperidin]-1'-yl)-2-(1,3-thiazol-4-ylmethyl)propanoate (step 1):
MS (ESI) 377 (M+H)+.

Example 53

3-(5-Fluoro-1-methyl-2-oxo-1,2-dihydro-1'H-spiro[indole-3,4'-piperidin]-1'-yl)-2-(1,3-thiazol-4-ylmethyl)propanoic acid trifluoroacetate

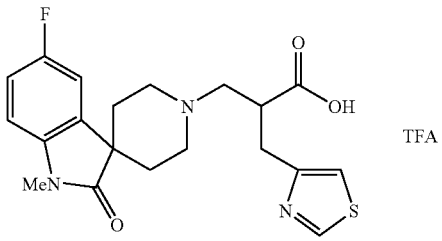

Step 1. tert-Butyl 3-(5-fluoro-1-methyl-2-oxo-1,2-dihydro-1'H-spiro[indole-3,4'-piperidin]-1'-yl)-2-(1,3-thiazol-4-ylmethyl)propanoate The title compound was prepared according to the procedure described in step 4 of example 4 from 5-fluoro-1-methylspiro[indole-3,4'-piperidin]-2(1H)-one (step 3 of example 6) and tert-butyl 2-(1,3-thiazol-4-ylmethyl)acrylate (step 2 of example 44):
$^1$H-NMR (CDCl$_3$) δ 8.76 (1H, d, J=2.0 Hz), 7.14 (1H, dd, J=8.4, 2.4 Hz), 7.04 (1H, d, J=2.0 Hz), 7.02-6.93 (1H, m), 6.75 (1H, dd, J=8.4, 4.4 Hz), 3.25-2.50 (12H, m), 2.00-1.85 (2H, m), 1.84-1.64 (2H, m), 1.40 (9H, s); MS (ESI) 460 (M+H)+.

Step 2. 3-(5-Fluoro-1-methyl-2-oxo-1,2-dihydro-1'H-spiro[indole-3,4'-piperidin]-1'-yl)-2-(1,3-thiazol-4-ylmethyl)propanoic acid trifluoroacetate The title compound was prepared according to the procedure described in step 3 of example 1 from tert-butyl 3-(5-fluoro-1-methyl-2-oxo-1,2-dihydro-1'H-spiro[indole-3,4'-piperidin]-1'-yl)-2-(1,3-thiazol-4-ylmethyl)propanoate (step 1):
MS (ESI) 404 (M+H)+.

Example 54

3-(2,3-Dihydro-1'H-spiro[indene-1,4'-piperidin]-1'-yl)-2-(1,3-thiazol-4-ylmethyl)propanoic acid trifluoroacetate

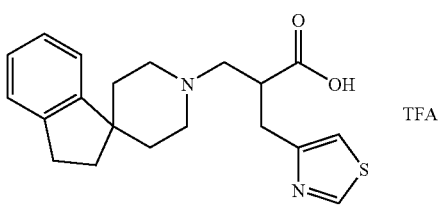

Step 1. tert-Butyl 3-(2,3-dihydro-1'H-spiro[indene-1,4'-piperidin]-1'-yl)-2-(1,3-thiazol-4-ylmethyl)propanoate The title compound was prepared according to the procedure described in step 4 of example 4 from 2,3-dihydrospiro[indene-1,4'-piperidine] and tert-butyl 2-(1,3-thiazol-4-ylmethyl)acrylate (step 2 of example 44):
$^1$H-NMR (CDCl$_3$) δ 8.75 (1H, d, J=2.0 Hz), 7.16-7.11 (2H, m), 7.02 (1H, d, J=2.0 Hz), 6.88-6.82 (2H, m), 3.13-2.95 (5H, m), 2.75-2.31 (4H, m), 2.19-2.01 (2H, m), 1.71-1.60 (6H, m), 1.38 (9H, s); MS (ESI) 419 (M+H)+.

Step 2. 3-(2,3-Dihydro-1'H-spiro[indene-1,4'-piperidin]-1'-yl)-2-(1,3-thiazol-4-ylmethyl)propanoic acid trifluoroacetate The title compound was prepared according to the procedure described in step 3 of example 1 from tert-butyl 3-(2,3-dihydro-1'H-spiro[indene-1,4'-piperidin]-1'-yl)-2-(1,3-thiazol-4-ylmethyl)propanoate (step 1):
$^1$H-NMR (CDCl$_3$) δ 9.67 (1H, d, J=2.2 Hz), 7.90 (1H, d, J=2.4 Hz), 7.26-7.20 (3H, m), 7.11-7.08 (1H, m), 3.85-3.05 (9H, m), 2.97 (2H, t, J=7.3 Hz), 2.33-2.16 (2H, m), 2.08 (2H, t, J=7.2 Hz), 1.80 (2H, br.d, J=14.9 Hz); MS (ESI) 357 (M+H)+.

Example 55

3-(6-Fluoro-1'H,3H-spiro[2-benzofuran-1,4'-piperidin]-1'-yl)-2-(1H-pyrazol-1-ylmethyl)propanoic acid

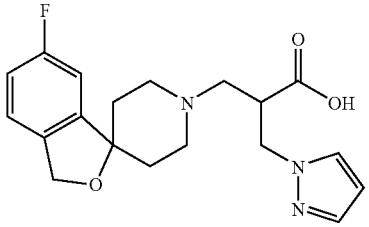

Step 1. Ethyl 3-(6-fluoro-1'H,3H-spiro[2-benzofuran-1,4'-piperidin]-1'-yl)-2-(hydroxymethyl)propanoate The title compound was prepared according to the procedure described in step 4 of example 4 from 6-fluoro-3H-spiro[2-benzofuran-1,4'-piperidine] (J. Med. Chem. 1995, 38, 2009.) and ethyl 2-(hydroxymethyl)acrylate:
$^1$H-NMR (CDCl$_3$) δ 7.14 (1H, dd, J=8.2, 5.0 Hz), 7.03-6.93 (1H, m), 6.79 (1H, dd, J=8.2, 2.2 Hz), 5.01 (2H, s), 4.15 (2H, q, J=7.1 Hz), 4.05-3.88 (2H, m), 3.12-2.80 (5H, m), 2.70-2.55 (1H, m), 2.47-2.31 (1H, m), 2.00-1.70 (4H, m), 1.27 (3H, t, J=7.1 Hz); MS (ESI) 338 (M+H)+.

Step 2. Ethyl 3-(6-fluoro-1'H,3H-spiro[2-benzofuran-1,4'-piperidin]-1'-yl)-2-(1H-pyrazol-1-ylmethyl)propanoate To a stirred solution of ethyl 3-(6-fluoro-1'H,3H-spiro[2-benzofuran-1,4'-piperidin]-1'-yl)-2-(hydroxymethyl)propanoate (step 1) and triethylamine in dichloromethane was added methanesulfonyl chloride at 0° C. The reaction mixture was stirred at the same temperature for 1 h, and quenched by the addition of sodium bicarbonate aqueous solution. The mixture was extracted with dichloromethane. The combined organic layers were dried over magnesium sulfate, and evaporated. The residue was dissolved with acetonitrile, and potassium carbonate and pyrazole were added to the solution. The mixture was stirred at 80° C. for 16 h, quenched by the addition of water, and extracted with ethyl acetate. The combined organic layers were washed with brine, dried over magnesium sulfate, and evaporated. The residue was purified by column chromatography on silica gel eluting with ethyl acetate/methanol (10/1) to afford the title compound as a colorless oil:

$^1$H-NMR (CDCl$_3$) δ 7.54-7.49 (1H, m), 7.45-7.40 (1H, m), 7.17-7.10 (1H, m), 7.00-6.90 (1H, m), 6.83-6.75 (1H, m), 6.25-6.20 (1H, m), 5.01 (2H, s), 4.48-4.35 (2H, m), 4.20-4.06 (2H, m), 3.37-3.23 (1H, m), 2.90-2.30 (6H, m), 1.98-1.65 (4H, m), 1.27-1.15 (3H, m); MS (ESI) 388 (M+H)$^+$.

Step 3. 3-(6-Fluoro-1'H,3H-spiro[2-benzofuran-1,4'-piperidin]-1'-yl)-2-(1H-pyrazol-1-ylmethyl)propanoic acid The title compound was prepared according to the procedure described in step 2 of example 33 from ethyl 3-(6-fluoro-1'H,3H-spiro[2-benzofuran-1,4'-piperidin]-1'-yl)-2-(1H-pyrazol-1-ylmethyl)propanoate (step 1):

MS (ESI) 360 (M+H)$^+$, 358 (M−H)$^−$.

Example 56

3-(1'H,3H-Spiro[2-benzofuran-1,4'-piperidin]-1'-yl)-2-(1,3-thiazol-4-ylmethyl)propanoic acid trifluoroacetate

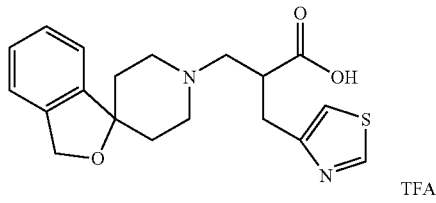

TFA

Step 1. tert-Butyl 3-(1'H,3H-spiro[2-benzofuran-1,4'-piperidin]-1'-yl)-2-(1,3-thiazol-4-ylmethyl)propanoate The title compound was prepared according to the procedure described in step 4 of example 4 from 3H-spiro[2-benzofuran-1,4'-piperidine] and tert-butyl 2-(1,3-thiazol-4-ylmethyl)acrylate (step 2 of example 44):

$^1$H-NMR (CDCl$_3$) δ 8.79-8.72 (1H, m), 7.32-7.15 (3H, m), 7.14-7.06 (1H, m), 7.05-6.99 (1H, m), 5.06 (2H, s), 3.15-3.00 (3H, m), 2.99-2.87 (1H, m), 2.84-2.67 (2H, m), 2.58-2.30 (3H, m), 1.99-1.83 (2H, m), 1.81-1.67 (2H, m), 1.39 (9H, s); MS (ESI) 415 (M+H)$^+$.

Step 2. 3-(1'H,3H-Spiro[2-benzofuran-1,4'-piperidin]-1'-yl)-2-(1,3-thiazol-4-ylmethyl)propanoic acid trifluoroacetate The title compound was prepared according to the procedure described in step 4 of example 44 from tert-butyl 3-(1'H,3H-spiro[2-benzofuran-1,4'-piperidin]-1'-yl)-2-(1,3-thiazol-4-ylmethyl)propanoate (step 1) and trifluoroacetic acid:

$^1$H-NMR (CDCl$_3$) δ 11.99 (1H, br.s), 9.63-9.54 (1H, m), 8.86-8.55 (1H, br.m), 7.90-7.80 (1H, m), 7.40-7.21 (3H, m), 7.17-7.07 (1H, m), 5.11 (2H, s), 3.90-3.18 (9H, m), 2.50-2.20 (2H, m), 2.07-1.90 (2H, m).

Example 57

3-(2,3-Dihydro-1'H-spiro[indene-1,4'-piperidin]-1'-yl)-2-(1H-pyrazol-1-ylmethyl)propanoic acid

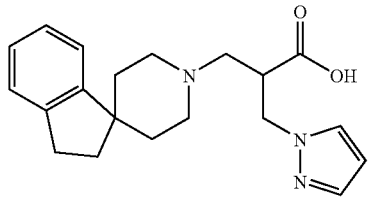

Step 1. Ethyl 2-(1H-pyrazol-1-ylmethyl)acrylate

A mixture of ethyl 2-(hydroxymethyl)acrylate (4.1 g, 32 mmol), pyrazole (2.6 g, 38 mmol) and potassium carbonate (11 g, 79 mmol) in acetonitrile (30 mL) was refluxed for 20 h, quenched by the addition of water (100 mL), and extracted with ethyl acetate (40 mL×2). The combined organic layers were washed with brine, dried over magnesium sulfate, and evaporated. The residue was purified by column chromatography on silica gel eluting with hexane/ethyl acetate (7/1) to afford 1.0 g (18%) of the title compound as a colorless oil:

$^1$H-NMR (CDCl$_3$) δ 7.57-7.53 (1H, m), 7.48-7.45 (1H, m), 6.36-6.32 (1H, m), 6.28 (1H, t, J=2.0 Hz), 5.48-5.44 (1H, m), 5.01 (2H, s), 4.24 (2H, q, J=7.1 Hz), 1.30 (3H, t, J=7.1 Hz).

Step 2. Ethyl 3-(2,3-dihydro-1'H-spiro[indene-1,4'-piperidin]-1'-yl)-2-(1H-pyrazol-1-ylmethyl)propanoate The title compound was prepared according to the procedure described in step 4 of example 4 from 2,3-dihydrospiro[indene-1,4'-piperidine] and ethyl 2-(1H-pyrazol-1-ylmethyl)acrylate (step 1):

$^1$H-NMR (CDCl$_3$) δ 7.55-7.48 (1H, m), 7.44-7.38 (1H, m), 7.25-7.10 (4H, m), 6.25-6.18 (1H, m), 4.48-4.38 (2H, m), 4.23-4.05 (2H, m), 3.38-3.22 (1H, m), 2.95-2.77 (2H, m), 2.88 (2H, t, J=7.3 Hz), 2.73-2.61 (1H, m), 2.58-2.46 (1H, m), 2.30-2.15 (2H, m), 1.98 (2H, t, J=7.3 Hz), 1.96-1.80 (2H, m), 1.58-1.45 (2H, m), 1.25 (3H, t, J=7.3 Hz); MS (ESI) 368 (M+H)$^+$.

Step 3. 3-(2,3-Dihydro-1'H-spiro[indene-1,4'-piperidin]-1'-yl)-2-(1H-pyrazol-1-ylmethyl)propanoic acid The title compound was prepared according to the procedure described in step 4 of example 30 from ethyl 3-(2,3-dihydro-1'H-spiro[indene-1,4'-piperidin]-1'-yl)-2-(1H-pyrazol-1-ylmethyl)propanoate (step 2):

MS (ESI) 340 (M+H)$^+$, 338 (M−H)$^−$.

Example 58

3-(3,4-Dihydro-1'H-spiro[isochromene-1,4'-piperidin]-1'-yl)-2-(1H-pyrazol-1-ylmethyl)propanoic acid

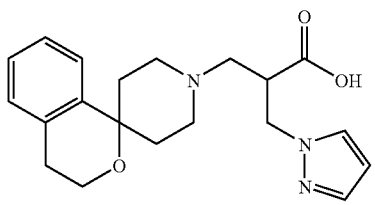

Step 1. Ethyl 3-(3,4-dihydro-1'H-spiro[isochromene-1,4'-piperidin]-1'-yl)-2-(1H-pyrazol-1-ylmethyl)propanoate The title compound was prepared according to the procedure described in step 4 of example 4 from 3,4-dihydrospiro[isochromene-1,4'-piperidine] and ethyl 2-(1H-pyrazol-1-ylmethyl)acrylate (step 1 of example 57):
$^1$H-NMR (CDCl$_3$) δ 7.51 (1H, d, J=2.0 Hz), 7.40 (1H, d, J=2.0 Hz), 7.25-7.05 (4H, m), 6.21 (1H, t, J=2.0 Hz), 4.48-4.36 (2H, m), 4.24-4.05 (2H, m), 3.88 (2H, t, J=5.5 Hz), 3.36-3.23 (1H, m), 2.82 (2H, t, J=5.5 Hz), 2.78-2.62 (3H, m), 2.58-2.38 (3H, m), 2.05-1.85 (4H, m), 1.22 (3H, t, J=7.2 Hz); MS (ESI) 384 (M+H)$^+$.

Step 2. 3-(3,4-Dihydro-1'H-spiro[isochromene-1,4'-piperidin]-1'-yl)-2-(1H-pyrazol-1-ylmethyl)propanoic acid The title compound was prepared according to the procedure described in step 4 of example 30 from ethyl 3-(3,4-dihydro-1'H-spiro[isochromene-1,4'-piperidin]-1'-yl)-2-(1H-pyrazol-1-ylmethyl)propanoate (step 1):
MS (ESI) 356 (M+H)$^+$, 354 (M–H)$^-$.

Example 59

3-(7-Fluoro-3,4-dihydro-1'H-spiro[isochromene-1,4'-piperidin]-1'-yl)-2-(1,3-thiazol-4-ylmethyl)propanoic acid trifluoroacetate

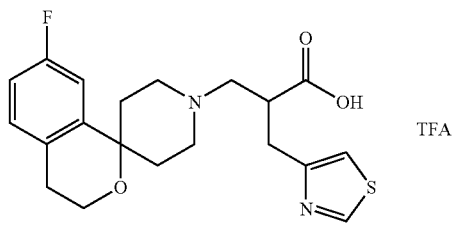

Step 1. 2-(2-Bromo-4-fluorophenyl)ethanol

To a solution of (2-bromo-4-fluorophenyl)acetic acid (1.5 g, 6.44 mmol) in tetrahydrofuran (10 mL) was added 1M solution of borane-tetrahydrofuran complex in tetrahydrofuran (9.66 mL, 9.66 mmol) at 0° C. The mixture was warmed to room temperature and stirred for 3 h. The reaction mixture was quenched by the addition of 2N hydrochloric acid (50 mL), extracted with ethyl acetate (200 mL). The organic layer was washed with brine (50 mL) dried over sodium sulfate, and evaporated. The residue was purified by column chromatography on silica gel (100 g) eluting with hexane/ethyl acetate (5/1) to afford 1.30 g (92%) of the title compound as colorless oil:
$^1$H-NMR (CDCl$_3$) δ 7.33-7.23 (2H, m), 6.99 (1H, dt, J=8.3, 2.6 Hz), 3.87 (2H, t, J=6.6 Hz), 3.00 (2H, t, J=6.7 Hz).

Step 2. Ethyl 4-[5-fluoro-2-(2-hydroxyethyl)phenyl]-4-hydroxypiperidine-1-carboxylate The title compound was prepared according to the procedure described in step 2 of example 36 from 2-(2-bromo-4-fluorophenyl):
$^1$H-NMR (CDCl$_3$) δ 7.18 (1H, dd, J=8.4, 6.2 Hz), 7.01 (1H, dd, J=11.4, 2.6 Hz), 6.95 (1H, dt, J=8.0, 2.7 Hz), 4.18-4.02 (4H, m), 3.94 (2H, t, J=5.8 Hz), 3.40-3.28 (4H, m), 2.01-1.83 (4H, m), 1.28 (3H, t, J=7.2 Hz); MS (ESI) 310 (M–H)$^-$.

Step 3. Ethyl 7-fluoro-3,4-dihydro-1'H-spiro[isochromene-1,4'-piperidine]-1'-carboxylate The title compound was prepared according to the procedure described in step 3 of example 36 from ethyl 7-fluoro-3,4-dihydro-1'H-spiro[isochromene-1,4'-piperidine]-1'-carboxylate (step 2):
$^1$H-NMR (CDCl$_3$) δ 7.07 (1H, dd, J=8.4, 5.9 Hz), 6.87 (1H, dt, J=8.4, 2.6 Hz), 6.78 (1H, dd, J=10.1, 2.6 Hz), 4.17 (2H, q, J=7.2 Hz), 4.07 (2H, br s), 3.90 (2H, t, J=5.5 Hz), 3.25-3.14 (2H, m), 2.79 (2H, t, J=5.4 Hz), 1.92-1.77 (4H, m), 1.29 (3H, t, J=7.1 Hz); MS (ESI) 294 (M+H)$^+$.

Step 4. 7-Fluoro-3,4-dihydrospiro[isochromene-1,4'-piperidine]

The title compound was prepared according to the procedure described in step 4 of example 36 from ethyl 7-fluoro-3,4-dihydro-1'H-spiro[isochromene-1,4'-piperidine]-1'-carboxylate (step 3):
$^1$H-NMR (CDCl$_3$) δ 7.05 (1H, dd, J=8.3, 5.9 Hz), 6.91-6.82 (2H, m), 3.89 (2H, t, J=5.5 Hz), 3.12-3.03 (2H, m), 2.95-2.89 (2H, m), 2.78 (2H, t, J=5.5 Hz), 1.91-1.83 (4H, m); MS (ESI) 222 (M+H)$^+$.

Step 5. tert-Butyl 3-(7-fluoro-3,4-dihydro-1'H-spiro[isochromene-1,4'-piperidin]-1'-yl)-2-(1,3-thiazol-4-ylmethyl)propanoate The title compound was prepared according to the procedure described in step 4 of example 4 from 7-fluoro-3,4-dihydrospiro[isochromene-1,4'-piperidine] (step 4) and tert-butyl 2-(1,3-thiazol-4-ylmethyl)acrylate (step 2 of example 44):
$^1$H-NMR (CDCl$_3$) δ 6 8.75 (1H, d, J=2.0 Hz), 7.06-7.01 (2H, m), 6.88-6.78 (2H, m), 3.86 (2H, t, J=5.5 Hz), 3.11-3.03 (3H, m), 2.85-2.64 (5H, m), 2.52-2.33 (3H, m), 1.95-1.82 (4H, m), 1.40 (9H, s); MS (ESI) 447 (M+H)$^+$.

Step 6. 3-(7-Fluoro-3,4-dihydro-1'H-spiro[isochromene-1,4'-piperidin]-1'-yl)-2-(1,3-thiazol-4-ylmethyl)propanoic acid trifluoroacetate The title compound was prepared according to the procedure described in step 3 of example 1 from tert-butyl 3-(7-fluoro-3,4-dihydro-1'H-spiro[isochromene-1,4'-piperidin]-1'-yl)-2-(1,3-thiazol-4-ylmethyl)propanoate (step 5):
MS (ESI) 391 (M+H)$^+$.

Example 60

3-(7-Fluoro-3,4-dihydro-1'H-spiro[isochromene-1,4'-piperidin]-1'-yl)-2-(1H-pyrazol-1-ylmethyl)propanoic acid

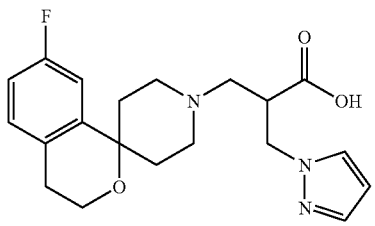

Step 1. Ethyl 3-(7-fluoro-3,4-dihydro-1'H-spiro[isochromene-1,4'-piperidin]-1'-yl)-2-(1H-pyrazol-1-ylmethyl)propanoate The title compound was prepared according to the procedure described in step 4 of example 4 from 7-fluoro-3,4-dihydrospiro[isochromene-1,4'-piperidine] (step 4 of example 60) and ethyl 2-(1H-pyrazol-1-ylmethyl)acrylate (step 1 of example 58):
$^1$H-NMR (CDCl$_3$) δ 7.51 (1H, d, J=1.8 Hz), 7.40 (1H, d, J=2.4 Hz), 7.07-7.02 (1H, m), 6.88-6.82 (2H, m), 6.21 (1H, t, J=1.8 Hz), 4.43-4.41 (2H, m), 4.18-4.09 (2H, m), 3.86 (2H, t, J=5.4 Hz), 3.34-3.25 (1H, m), 2.78-2.65 (5H, m), 2.55-2.38 (3H, m), 1.97-1.81 (4H, m), 1.22 (3H, t, J=7.0 Hz); MS (ESI) 402 (M+H)$^+$.

Step 2. 3-(7-Fluoro-3,4-dihydro-1'H-spiro[isochromene-1,4'-piperidin]-1'-yl)-2-(1H-pyrazol-1-ylmethyl)propanoic acid The title compound was prepared according to the procedure described in step 4 of example 30 from ethyl 3-(7-fluoro-3,4-dihydro-1'H-spiro[isochromene-1,4'-piperidin]-1'-yl)-2-(1H-pyrazol-1-ylmethyl)propanoate (step 1): MS (ESI) 374 (M+H)$^+$, 372 (M−H)$^-$.

Example 61

3-(6-Fluoro-3,4-dihydro-1'H-spiro[isochromene-1,4'-piperidin]-1'-yl)-2-(1H-pyrazol-1-ylmethyl)propanoic acid

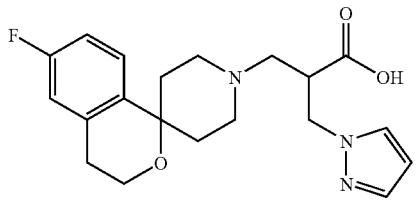

Step 1. 2-(2-Bromo-5-fluorophenyl)ethanol

To a solution of (2-bromo-5-fluorophenyl)acetic acid (1.29 g, 5.54 mmol) in tetrahydrofuran (15 mL) was added lithium aluminum hydride (210 mg, 5.54 mmol) at 0° C. The mixture was warmed to room temperature and stirred for 3 h. After cooling to 0° C., the reaction mixture was quenched by the addition of 2N hydrochloric acid (30 mL), extracted with diethyl ether (200 mL). The organic layer was washed with water (50 mL) and brine (50 mL) dried over magnesium sulfate, and evaporated. The residue was purified by column chromatography on silica gel (40 g) eluting with hexane/ethyl acetate (5/1) to afford 247 mg (20%) of the title compound as colorless oil:
$^1$H-NMR (CDCl$_3$) δ 7.51 (1H, dd, J=8.8, 5.4 Hz), 7.04 (1H, dd, J=9.2, 3.1 Hz), 6.84 (1H, dt, J=8.4, 3.1 Hz), 3.93-3.87 (2H, m), 3.01 (2H, t, J=6.6 Hz), 1.44 (1H, J=5.7 Hz).

Step 2. Ethyl 4-[4-fluoro-2-(2-hydroxyethyl)phenyl]-4-hydroxypiperidine-1-carboxylate The title compound was prepared according to the procedure described in step 2 of example 36 from 2-(2-bromo-5-fluorophenyl)ethanol (step 1):
$^1$H-NMR (CDCl$_3$) δ 7.30-7.25 (1H, m), 6.95-6.86 (2H, m), 4.18-3.96 (6H, m), 3.83 (1H, br.s), 3.40-3.30 (2H, m), 2.01-1.82 (4H, m), 1.27 (3H, t, J=7.2 Hz); MS (ESI) 310 (M−H)$^-$.

Step 3. Ethyl 6-fluoro-3,4-dihydro-1'H-spiro[isochromene-1,4'-piperidine]-1'-carboxylate The title compound was prepared according to the procedure described in step 3 of example 36 from ethyl 4-[4-fluoro-2-(2-hydroxyethyl)phenyl]-4-hydroxypiperidine-1-carboxylate (step 2):
$^1$H-NMR (CDCl$_3$) δ 7.06-7.01 (1H, m), 6.89 (1H, dt, J=8.5, 2.6 Hz), 6.80 (1H, dd, J=9.3, 2.7 Hz), 4.17 (2H, q, J=7.0 Hz), 4.05 (2H, br.s), 3.90 (2H, t, J=5.5 Hz), 3.19 (2H, br.s), 2.82 (2H, t, J=5.5 Hz), 1.87-1.82 (4H, m), 1.29 (3H, t, J=7.2 Hz); MS (ESI) 294 (M+H)$^+$.

Step 4. 6-Fluoro-3,4-dihydrospiro[isochromene-1,4'-piperidine]

The title compound was prepared according to the procedure described in step 4 of example 36 from ethyl 6-fluoro-3,4-dihydro-1'H-spiro[isochromene-1,4'-piperidine]-1'-carboxylate (step 3):
$^1$H-NMR (CDCl$_3$) δ 7.14 (1H, dd, J=8.7, 5.6 Hz), 6.89 (1H, dt, J=8.7, 2.5 Hz), 6.79 (1H, dd, J=9.4, 2.8 Hz), 3.90 (2H, t, J=5.6 Hz), 3.12-3.02 (2H, m), 2.93-2.87 (2H, m), 2.81 (2H, t, J=5.4 Hz), 1.87-1.83 (4H, m);
MS (ESI) 222 (M+H)$^+$.

Step 5. Ethyl 3-(6-fluoro-3,4-dihydro-1'H-spiro[isochromene-1,4'-piperidin]-1'-yl)-2-(1H-pyrazol-1-ylmethyl)propanoate)propanoate The title compound was prepared according to the procedure described in step 4 of example 4 from 6-fluoro-3,4-dihydrospiro[isochromene-1,4'-piperidine] (step 4) and ethyl 2-(1H-pyrazol-1-ylmethyl)acrylate (step 1 of example 57):
$^1$H-NMR (CDCl$_3$) δ 7.51 (1H, d, J=1.8 Hz), 7.40 (1H, d, J=2.4 Hz), 7.09 (1H, dd, J=8.7, 5.6 Hz), 6.88 (1H, dt, J=8.5, 2.8 Hz), 6.78 (1H, dd, J=9.4, 2.6 Hz), 6.21 (1H, t, J=2.1 Hz), 4.44-4.40 (2H, m), 4.19-4.09 (2H, m), 3.87 (2H, t, J=5.6 Hz), 3.34-3.24 (1H, m), 2.80 (2H, t, J=5.5 Hz), 2.72-2.65 (3H, m), 2.55-2.38 (3H, m), 2.00-1.81 (4H, m), 1.21 (3H, t, J=7.2 Hz); MS (ESI) 402 (M+H)$^+$.

Step 6. 3-(6-Fluoro-3,4-dihydro-1'H-spiro[isochromene-1,4'-piperidin]-1'-yl)-2-(1H-pyrazol-1-ylmethyl)propanoic acid The title compound was prepared according to the procedure described in step 4 of example 30 from ethyl 3-(6-fluoro-3,4-dihydro-1'H-spiro[isochromene-1,4'-piperidin]-1'-yl)-2-(1H-pyrazol-1-ylmethyl)propanoate)propanoate (step 5):
MS (ESI) 374 (M+H)$^+$, 372 (M−H)$^-$.

Example 62

3-(4,5-Dihydro-1'H,3H-spiro[2-benzoxepine-1,4'-piperidin]-1'-yl)-2-(1,3-thiazol-4-ylmethyl)propanoic acid trifluoroacetate

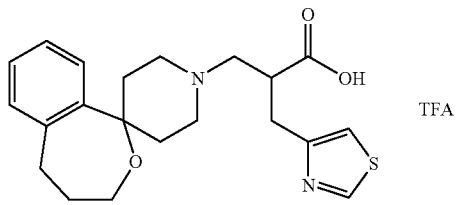

Step 1. Ethyl 4-hydroxy-4-[2-(3-hydroxypropyl)phenyl]piperidine-1-carboxylate The title compound was prepared according to the procedure described in step 2 of example 36 from 3-(2-bromophenyl)propan-1-ol (*J. Am. Chem. Soc.* 2003, 125, 3509.) and ethyl 4-oxopiperidine-1-carboxylate:
$^1$H-NMR (CDCl$_3$) δ 7.34-7.10 (4H, m), 4.20-3.90 (2H, m), 4.14 (2H, q, J=7.1 Hz), 3.63 (2H, t, J=5.9 Hz), 3.45-3.25 (2H, m), 3.12 (2H, t, J=7.6 Hz), 2.10-1.85 (6H, m), 1.26 (3H, t, J=7.1 Hz).

Step 2. Ethyl 4,5-dihydro-1'H,3H-spiro[2-benzoxepine-1,4'-piperidine]-1'-carboxylate The title compound was prepared according to the procedure described in step 3 of example 36 from ethyl 4-hydroxy-4-[2-(3-hydroxypropyl)phenyl]piperidine-1-carboxylate (step 1):
$^1$H-NMR (CDCl$_3$) δ 7.37-7.14 (4H, m), 4.22-3.95 (2H, m), 4.15 (2H, q, J=7.1 Hz), 3.64 (2H, t, J=6.4 Hz), 3.45-3.25 (2H, m), 3.20-3.08 (2H, m), 2.18-1.90 (6H, m), 1.27 (3H, t, J=7.1 Hz).

Step 3. 4,5-Dihydro-3H-spiro[2-benzoxepine-1,4'-piperidine]

The title compound was prepared according to the procedure described in step 4 of example 36 from ethyl 4,5-dihydro-1'H,3H-spiro[2-benzoxepine-1,4'-piperidine]-1'-carboxylate (step 2):
MS (ESI) 218 (M+H)$^+$.

Step 4. tert-Butyl 3-(4,5-dihydro-1'H,3H-spiro[2-benzoxepine-1,4'-piperidin]-1'-yl)-2-(1,3-thiazol-4-ylmethyl)propanoate The title compound was prepared according to the procedure described in step 4 of example 4 from 4,5-dihydro-3H-spiro[2-benzoxepine-1,4'-piperidine] (step 3) and tert-butyl 2-(1,3-thiazol-4-ylmethyl)acrylate (step 2 of example 44):
$^1$H-NMR (CDCl$_3$) δ 8.75 (1H, d, J=2.0 Hz), 7.25-7.03 (4H, m), 7.02 (1H, d, J=2.0 Hz), 3.66 (2H, t, J=6.6 Hz), 3.16-2.90 (5H, m), 2.88-2.63 (3H, m), 2.58-2.35 (3H, m), 2.05-1.80 (6H, m), 1.38 (9H, s); MS (ESI) 443 (M+H)$^+$.

Step 5. 3-(4,5-Dihydro-1'H,3H-spiro[2-benzoxepine-1,4'-piperidin]-1'-yl)-2-(1,3-thiazol-4-ylmethyl)propanoic acid trifluoroacetate The title compound was prepared according to the procedure described in step 3 of example 1 from tert-butyl 3-(4,5-dihydro-1'H,3H-spiro[2-benzoxepine-1,4'-piperidin]-1'-yl)-2-(1,3-thiazol-4-ylmethyl)propanoate (step 4):
MS (ESI) 387 (M+H)$^+$.

Example 63

3-(6-Fluoro-3,4-dihydro-1'H-spiro[isochromene-1,4'-piperidin]-1'-yl)-2-(1,3-thiazol-4-ylmethyl)propanoic acid trifluoroacetate

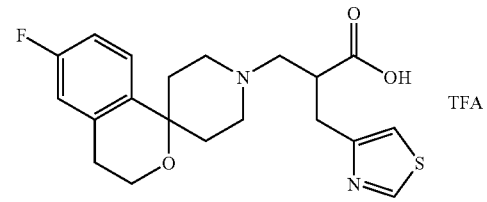

Step 1. tert-Butyl 3-(6-fluoro-3,4-dihydro-1'H-spiro[isochromene-1,4'-piperidin]-1'-yl)-2-(1,3-thiazol-4-ylmethyl)propanoate The title compound was prepared according to the procedure described in step 4 of example 4 from 6-fluoro-3,4-dihydrospiro[isochromene-1,4'-piperidine] (step 4 of example 61) and tert-butyl 2-(1,3-thiazol4-ylmethyl)acrylate (step 2 of example 44):
$^1$H-NMR (CDCl$_3$) δ 8.75 (1H, d, J=2.0 Hz), 7.06 (1H, dd, J=8.7, 5.6 Hz), 7.02 (1H, d, J=1.8 Hz), 6.88 (1H, dt, J=8.6, 2.7 Hz), 6.78 (1H, dd, J=9.3, 2.7 Hz), 3.87 (2H, t, J=5.5 Hz), 3.11-3.02 (3H, m), 2.84-2.65 (5H, m), 2.52-2.33 (3H, m), 1.97-1.80 (4H, m), 1.39 (9H, s); MS (ESI) 402 (M+H)$^+$.

Step 2. 3-(6-Fluoro-3,4-dihydro-1'H-spiro[isochromene-1,4'-piperidin]-1'-yl)-2-(1,3-thiazol-4-ylmethyl)propanoic acid trifluoroacetate The title compound was prepared according to the procedure described in step 3 of example 1 from tert-butyl 3-(6-fluoro-3,4-dihydro-1'H-spiro[isochromene-1,4'-piperidin]-1'-yl)-2-(1,3-thiazol-4-ylmethyl)propanoate (step 1):
MS (ESI) 374 (M+H)$^+$, 372 (M−H)$^-$.

Example 64

3-(5-Fluoro-1-methyl-1,2-dihydro-1'H-spiro[indole-3,4'-piperidin]-1'-yl)-2-(1,3-thiazol-4-ylmethyl)propanoic acid trifluoroacetate

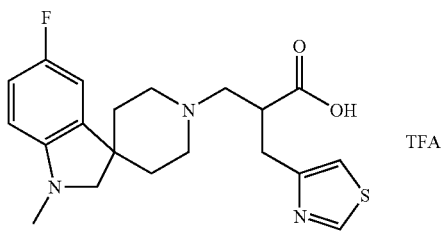

Step 1. tert-Butyl 3-(5-fluoro-1-methyl-1,2-dihydro-1'H-spiro[indole-3,4'-piperidin]-1'-yl)-2-(1,3-thiazol-4-ylmethyl)propanoate The title compound was prepared according to the procedure described in step 1 of example 32 from tert-butyl 3-(5-fluoro-1-methyl-1,2-dihydro-1'H-spiro[indole-3,4'-piperidin]-1'-yl)propanoate (step 1 of example 28):

$^1$H-NMR (CDCl$_3$) δ 8.75 (1H, d, J=2.0 Hz), 7.02 (1H, d, J=2.0 Hz), 6.81-6.70 (2H, m), 6.37-6.33 (1H, m), 3.18-2.67 (7H, m), 2.49-2.43 (2H, m), 2.22-2.01 (2H, m), 1.87-1.61 (4H, m), 1.49-1.22 (12H, m).

Step 2. 3-(5-Fluoro-1-methyl-1,2-dihydro-1'H-spiro[indole-3,4'-piperidin]-1'-yl)-2-(1,3-thiazol-4-ylmethyl)propanoic acid trifluoroacetate The title compound was prepared according to the procedure described in step 3 of example 1 from tert-butyl 3-(5-fluoro-1-methyl-1,2-dihydro-1'H-spiro[indole-3,4'-piperidin]-1'-yl)-2-(1,3-thiazol-4-ylmethyl)propanoate (step 1):

MS (ESI) 390 (M+H)$^+$, 388 (M–H)$^-$.

Example 65

2-(2-CHLOROBENZYL)-3-(2,3-DIHYDRO-1'H-SPIRO[INDENE-1,4'-PIPERIDIN]-1'-YL)PROPANOIC ACID

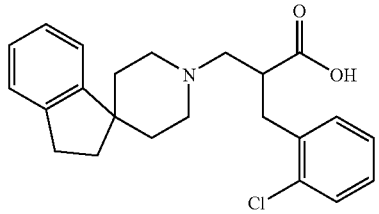

Step 1. Ethyl 2-(2-chlorobenzyl)-3-(2,3-dihydro-1'H-spiro[indene-1,4'-piperidin]-1'-yl)propanoate The title compound was prepared according to the procedure described in step 4 of example 4 from 2,3-dihydrospiro[indene-1,4'-piperidine] and ethyl 2-(2-chlorobenzyl)acrylate (step 2 of example 17):

$^1$H-NMR (CDCl$_3$) δ 7.36-7.30 (1H, m), 7.24-7.10 (7H, m), 4.15-3.98 (2H, m), 3.15-3.05 (2H, m), 2.95-2.74 (6H, m), 2.55-2.48 (1H, m), 2.27-2.12 (2H, m), 2.03-1.81 (4H, m), 1.51-1.45 (2H, m), 1.14 (3H, t, J=7.3 Hz); MS (ESI) 412 (M+H)$^+$.

Step 2. 2-(2-chlorobenzyl)-3-(2,3-dihydro-1'H-spiro[indene-1,4'-piperidin]-1'-yl)propanoic acid The title compound was prepared according to the procedure described in step 4 of example 30 from ethyl 2-(2-chlorobenzyl)-3-(2,3-dihydro-1'H-spiro[indene-1,4'-piperidin]-1'-yl)propanoate (step 1):

IR (KBr)ν 3400, 1709 cm$^{-1}$; $^1$H-NMR (CDCl$_3$) δ 7.38-7.33 (2H, m), 7.23-7.14 (6H, m), 3.57 (1H, dd, J=14.1, 5.1 Hz), 3.22 (1H, br d, J=12.6 Hz), 3.06-2.53 (8H, m), 2.35-2.23 (1H, m), 2.09-1.91 (4H, m), 1.68-1.61 (2H, m); MS (ESI) 384 (M+H)$^+$, 382 (M–H)$^-$; Anal. calcd. for C$_{23}$H$_{26}$ClNO$_2$: C, 71.96; H, 6.83; N, 3.65. Found: C, 71.56; H, 6.86; N, 3.45.

The invention claimed is:

1. A compound of the following formula (I)

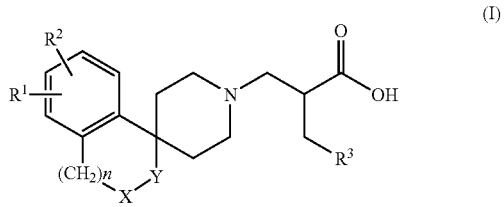

or a pharmaceutically acceptable salt thereof, wherein
R$^1$ and R$^2$ independently represent a hydrogen atom, a halogen atom or an alkyl group having from 1 to 3 carbon atoms;
R$^3$ represents an aryl group having from 6 to 10 ring atoms or a heteroaryl group and said heteroaryl group is a 5- to 10-membered heteroaromatic group containing from 1 to 3 heteroatoms selected from an oxygen atom, a sulfur atom and a nitrogen atom;
said aryl group and heteroaryl group are optionally substituted by 1 to 3 groups selected from a halogen atom, a hydroxy group, an alkyl group having from 1 to 3 carbon atoms, an alkoxy group having from 1 to 3 carbon atoms, an alkyl group having from 1 to 6 carbon atoms interrupted by an oxygen atom, a hydroxyalkyl group having from 1 to 3 carbon atoms, an amino group, a mono-or di-alkylamino group having from 1 to 3 carbon atoms, an aminocarbonyl group, a mono- or di-alkylaminocarbonyl group having from 1 to 3 carbon atoms in each alkyl group, an alkanoylamino group having from 1 to 3 carbon atoms and an alkylsulfonylamino group having from 1 to 3 carbon atoms;
—X—Y— represents a group of the formula —N(R$^4$)C(=O)—, —C(=O)N(R$^4$)—, —N(R$^4$)CH$_2$—, —CH$_2$N(R$^4$)—, —N(R$^4$)SO$_2$—, —SO$_2$N(R$^4$)—, —CH$_2$CH$_2$—, —CH=CH—, —CH(CH$_2$OH)CH$_2$—, —CH$_2$CH(CH$_2$OH)—, —CH$_2$CH(OH)—, —CH(OH)CH$_2$—, —C(R$^4$)(R$^5$)—O— or —O—C(R$^4$)(R$^5$)—;
R$^4$ represents a hydrogen atom or an alkyl group having from 1 to 3 carbon atoms;
R$^5$ represents a hydrogen atom, an alkyl group having from 1 to 3 carbon atoms or a hydroxyalkyl group having from 1 to 3 carbon atoms; and n represents an integer 0, 1 or 2.

2. The compound according to claim 1, wherein R$^1$ and R$^2$ independently represent a hydrogen atom or a fluorine atom.

3. The compound according to claim 1, wherein
R$^3$ represents a phenyl group or a heteroaryl group and said heteroaryl group is a 5- to 6-membered heteroaromatic group containing from 1 to 2 nitrogen heteroatoms or 1 or 2 nitrogen heteroatoms and 1 oxygen or 1 sulfur atom;
said phenyl group and heteroaryl group are optionally substituted by 1 to 3 groups selected from a halogen atom, a hydroxyl group, an alkyl group having from 1 to 3 carbon atoms, an alkyl group having from 1 to 6 carbon atoms interrupted by an oxygen atom, a hydroxyalkyl group having from 1 to 3 carbon atoms, an amino group and an alkylsulfonylamino group having from 1 to 3 carbon atoms.

4. The compound according to claim 1, wherein
R³ represents a phenyl group or a heteroaryl group selected from a pyridyl group, a thialzolyl group, a pyrazolyl group and an oxazolyl group;
said phenyl group is optionally substituted by 1 to 3 groups selected from a fluorine atom, a chlorine atom, a hydroxy group, a methyl group, a methoxymethyl group, a hydroxymethyl group, an amino group and methanesulfonylamino.

5. The compound according to claim 1, wherein —X—Y— represents a group of the formula —N(CH₃)C(=O)—, —N(CH₃)CH₂—, —N(CH₃)SO₂—, —CH₂O—, —CH(CH₃)O—, —C(CH₃)₂O—, —CH(CH₂OH)O—, —CH₂CH₂—, —CH(CH₂OH)CH₂—, —CH(OH)CH₂—, —CH=CH—, or —CH₂CH(OH)—.

6. The compound according to claim 1, wherein —X—Y— represents a group of the formula —N(CH₃)C(=O)—, —CH₂O—, —CH(CH₃)O—, —C(CH₃)₂O— or —CH₂CH₂—.

7. The compound according to claim 1, wherein n represents an integer 0.

8. A compound according to claim 1 selected from:
2-Benzyl-3-(2,3-dihydro-1'H-spiro[indene-1,4'-piperidin]-1'-yl)propanoic acid trifluoroacetate;
2-(2-Chlorobenzyl)-3-(1'H,3H-spiro[2-benzofuran-1,4'-piperidin]-1'-yl)propanoic acid trifluoroacetate;
2-(5-{[tert-Butyl(dimethyl)silyl]oxy}-2-fluorobenzyl)-3-(1'H,3H-spiro[2-benzofuran-1,4'piperidin]-1'-yl)propanoic acid trifluoroacetate;
2-(2-Chloro-5-hydroxybenzyl)-3-(1'H,3H-spiro[2-benzofuran-1,4'-piperidin]-1'-yl)propanoic acid;
2-(2-Chlorobenzyl)-3-(1-methyl-2-oxo-1,2-dihydro-1'H-spiro[indole-3,4'-piperidin]-1'-yl)propanoic acid;
2-(2-Chlorobenzyl)-3-(5-fluoro-1-methyl-1,2-dihydro-1'H-spiro[indole-3,4'-piperidin]-1'-yl)propanoic acid;
2-(2-Fluoro-5-hydroxybenzyl)-3-(1-methyl-2-oxo-1,2-dihydro-1'H-spiro[indole-3,4'-piperidin]-1'-yl)propanoic acid;
2-(2-Chlorobenzyl)-3-(6-fluoro-1'H,3H-spiro[2-benzofuran-1,4'-piperidin]-1'-yl)propanoic acid;
2-(2-Chloro-5-hydroxybenzyl)-3-(1-methyl-2-oxo-1,2-dihydro-1'H-spiro[indole-3,4'-piperidin]-1'-yl)propanoic acid;
2-(5-{[tert-Butyl(dimethyl)silyl]oxy}-2-fluorobenzyl)-3-(5-fluoro-1-methyl-1,2-dihydro-1'H-spiro[indole-3,4'-piperidin]-1'-yl)propanoic acid trifluoroacetate;
2-(5-{[tert-Butyl(dimethyl)silyl]oxy}-2-chlorobenzyl)-3-(5-fluoro-1-methyl-1,2-dihydro-1'H-spiro[indole-3,4'-piperidin]-1'-yl)propanoic acid trifluoroacetate;
2-(2-Chloro-5-hydroxybenzyl)-3-(5-fluoro-1-methyl-2-oxo-1,2-dihydro-1'H-spiro[indole-3,4'-piperidin]-1'-yl)propanoic acid;
2-(2-Fluoro-5-hydroxybenzyl)-3-(5-fluoro-1-methyl-2-oxo-1,2-dihydro-1'H-spiro[indole-3,4'-piperidin]-1'-yl)propanoic acid;
2-(2-Chloro-5-hydroxybenzyl)-3-(2-hydroxy-2,3-dihydro-1'H-spiro[indene-1,4'-piperidin]-yl)propanoic acid;
2-(2-chloro-5-hydroxybenzyl)-3-(3-methyl-1'H,3H-spiro[2-benzofuran-1,4'-piperidin]-1'-yl)propanoic acid;
2-(2-Chloro-5-hydroxybenzyl)-3-[3-(hydroxymethyl)-2,3-dihydro-1'H-spiro[indene-1,4'-piperidin]-1'-yl]propanoic acid; 2-(2-chloro-5-hydroxybenzyl)-3-(3-hydroxy-2,3-dihydro-1'H-spiro[indene-1,4'-piperidin]-1'-yl)propanoic acid;
2-(2-Chloro-5-hydroxybenzyl)-3-(5-fluoro-1'H,3H-spiro[2-benzofuran-1,4'-piperidin]-1'-yl)propanoic acid;
3-(3-Methyl-1'H,3H-spiro[2-benzofuran-1,4'-piperidin]-1'-yl)-2-(pyridin-2-ylmethyl)propanoic acid;
3-(3-Methyl-1'H,3H-spiro[2-benzofuran-1,4'-piperidin]-1'-yl)-2-(1,3-thiazol-4-ylmethyl)propanoic acid trifluoroacetate;
3-(3,4-Dihydro-1'H-spiro[isochromene-1,4'-piperidin]-1'-yl)-2-(1,3-thiazol-4-ylmethyl)propanoic acid trifluoroacetate;
3-(5-Fluoro-1-methyl-2-oxo-1,2-dihydro-1'H-spiro[indole-3,4'-piperidin]-1'-yl)-2-(1,3-thiazol-4-ylmethyl)propanoic acid trifluoroacetate;
3-(2,3-Dihydro-1'H-spiro[indene-1,4'-piperidin]-1'-yl)-2-(1,3-thiazol-4-ylmethyl)propanoic acid trifluoroacetate;
3-(2,3-Dihydro-1'H-spiro[indene-1,4'-piperidin]-1'-yl)-2-(1H-pyrazol-1-ylmethyl)propanoic acid;
3-(6-Fluoro-3,4-dihydro-1'H-spiro[isochromene-1,4'-piperidin]-1'-yl)-2-(1H-pyrazol-1-ylmethyl)propanoic acid; and
3-(6-Fluoro-3,4-dihydro-1'H-spiro[isochromene-1,4'-piperidin]-1'-yl)-2-(1,3-thiazol-4-ylmethyl)propanoic acid trifluoroacetate;
or a pharmaceutically acceptable salt thereof.

9. A pharmaceutical composition comprising a compound of the formula (I) or a pharmaceutically acceptable salt thereof, as defined in claim 1 together with a pharmaceutically acceptable excipient.

* * * * *